US012679886B2

(12) United States Patent
Shi et al.

(10) Patent No.: US 12,679,886 B2
(45) Date of Patent: Jul. 14, 2026

(54) SERUM ALBUMIN BINDING NANOBODY COMPOSITIONS AND METHODS FOR USING THE SAME

(71) Applicant: UNIVERSITY OF PITTSBURGH-OF THE COMMONWEALTH SYSTEM OF HIGHER EDUCATION, Pittsburgh, PA (US)

(72) Inventors: Yi Shi, Wexford, PA (US); Zhuolun Shen, Pittsburgh, PA (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 894 days.

(21) Appl. No.: 17/909,578

(22) PCT Filed: Mar. 5, 2021

(86) PCT No.: PCT/US2021/021094
§ 371 (c)(1),
(2) Date: Sep. 6, 2022

(87) PCT Pub. No.: WO2021/178804
PCT Pub. Date: Sep. 10, 2021

(65) Prior Publication Data
US 2023/0212270 A1      Jul. 6, 2023

Related U.S. Application Data

(60) Provisional application No. 62/986,180, filed on Mar. 6, 2020.

(51) Int. Cl.
| | |
|---|---|
| C07K 16/28 | (2006.01) |
| A61P 35/00 | (2006.01) |
| C07K 14/55 | (2006.01) |
| C07K 16/18 | (2006.01) |
| A61K 38/00 | (2006.01) |
| A61K 39/00 | (2006.01) |

(52) U.S. Cl.
CPC .............. *C07K 16/18* (2013.01); *A61P 35/00* (2018.01); *C07K 14/55* (2013.01); *A61K 38/00* (2013.01); *A61K 2039/505* (2013.01); *C07K 2317/34* (2013.01); *C07K 2317/565* (2013.01); *C07K 2317/569* (2013.01); *C07K 2317/92* (2013.01); *C07K 2319/30* (2013.01)

(58) Field of Classification Search
CPC .... C07K 16/18; C07K 14/55; C07K 2317/34; C07K 2317/565; C07K 2317/569; C07K 2317/92; C07K 2319/30; C07K 2319/00; C07K 2317/22; C07K 2317/31; C07K 2319/74; C07K 16/246; A61P 35/00; A61K 38/00; A61K 2039/505
See application file for complete search history.

(56) References Cited

U.S. PATENT DOCUMENTS

| | | | |
|---|---|---|---|
| 2014/0186365 A1 | 7/2014 | Robinson et al. | |
| 2017/0128499 A1 | 5/2017 | Falb et al. | |
| 2019/0169581 A1 | 6/2019 | Buller et al. | |
| 2020/0040052 A1 | 2/2020 | Winston et al. | |

FOREIGN PATENT DOCUMENTS

| | | |
|---|---|---|
| JP | 2016-508143 A | 3/2016 |
| WO | 1994/004678 | 3/1994 |
| WO | 2001/25397 A2 | 4/2001 |
| WO | 2006/122787 A1 | 11/2006 |
| WO | 2008043821 A1 | 4/2008 |
| WO | 2014/106583 A1 | 7/2014 |
| WO | 2016/022671 | 2/2016 |
| WO | 2018176030 A2 | 9/2018 |

OTHER PUBLICATIONS

Kijanka et al. (Eur J Nucl Med Mol Imaging, 40: 1718-1729, 2013).*
Extended European Search Report mailed May 27, 2024, issued in corresponding European Application No. 21764118.2, 11 pages.
U.S. Appl. No. 14/209,699, filed Feb. 28, 2017, Gavin et al.
Rosenberg, S. A. (2014). IL-2: the first effective immunotherapy for human cancer. The Journal of Immunology, 192(12), 5451-5458.
Arenas-Ramirez, N., Zou, C., Popp, S., Zingg, D., Brannetti, B., Wirth, E., Calzascia, T., Kovarik, J., Sommer, L., Zenke, G., et al. (2016). Improved cancer immunotherapy by a CD25-mimobody conferring selectivity to human interleukin-2. Sci Transl Med 8.
Levin, A.M., Bates, D.L., Ring, A.M., Krieg, C., Lin, J.T., Su, L., Moraga, I., Raeber, M.E., Bowman, G.R., Novick, P., et al. (2012). Exploiting a natural conformational switch to engineer an interleukin-2 'superkine'. Nature 484, 529-U159.
Silva, D.A., Yu, S., Ulge, U.Y., Spangler, J.B., Jude, K.M., Labao-Almeida, C., Ali, L.R., Quijano-Rubio, A., Ruterbusch, M., Leung, I., et al. (2019). De novo design of potent and selective mimics of IL-2 and IL-15. Nature 565, 186-191.
Zhu, E.F., Gai, S.A., Opel, C.F., Kwan, B.H., Surana, R., Mihm, M.C., Kauke, M.J., Moynihan, K.D., Angelini, A., Williams, R.T., et al. (2015). Synergistic Innate and Adaptive Immune Response to Combination Immunotherapy with Anti-Tumor Antigen Antibodies and Extended Serum Half-Life IL-2. Cancer Cell 27, 489-501.
Needleman, Saul B., and Christian D. Wunsch. "A general method applicable to the search for similarities in the amino acid sequence of two proteins." Journal of molecular biology 48.3 (1970): 443-453.
Anderson N.L. The clinical plasma proteome: a survey of clinical assays for proteins in plasma and serum. Clin. Chem. 2010;56:177-185. [PubMed] [Google Scholar].

(Continued)

*Primary Examiner* — Nelson B Moseley, II
(74) *Attorney, Agent, or Firm* — Meunier Carlin & Curfman LLC

(57) ABSTRACT

Disclosed herein are compositions and methods for increasing the stability of recombinant nanobodies. Also disclosed herein are recombinant nanobodies comprising an IL-2 polypeptide that bind serum albumin and uses thereof for treating cancers.

24 Claims, 26 Drawing Sheets

Specification includes a Sequence Listing.

(56)       References Cited

OTHER PUBLICATIONS

Baker M. Reproducibility crisis: blame it on the antibodies. Nature. 2015;521:274-276.

Boyman O., Sprent J. The role of interleukin-2 during homeostasis and activation of the immune system. Nat. Rev. Immunol. 2012;12:180-190.

Carter P.J. Potent antibody therapeutics by design. Nat. Rev. Immunol. 2006;6:343-357.

Chait B.T., Cadene M., Olinares P.D., Rout M.P., Shi Y. Revealing higher order protein structure using mass spectrometry. J. Am. Soc. Mass Spectrom. 2016;27:952-965.

Chen X., Bian Y., Xie Y., Zheng N., Nie K., Liu R., Yan M., Luo H., Wang H., Yang J. A dual target-directed single domain-based fusion protein against interleukin-6 receptor decelerate experimental arthritis progression via modulating JNK expression. Inflammation. 2021;44:1620-162.

Chen Z.-L., Meng J.-M., Cao Y., Yin J.- L., Fang R.-Q., Fan S.-B., Liu C., Zeng W.-F., Ding Y.-H., Tan D. A high-speed search engine pLink 2 with systematic evaluation for proteome-scale identification of cross-linked peptides. Nat. Commun. 2019;10:3404.

Coppieters K., Dreier T., Silence K., de Haard H., Lauwereys M., Casteels P., Beirnaert E., Jonckheere H., Van de Wiele C., Staelens L. Formatted anti-tumor necrosis factor alpha VHH proteins derived from camelids show superior potency and targeting to inflamed joints in a murine model of collagen-induced arthritis. Arthritis Rheum. 2006;54:1856-1866.

Cox J., Mann M. MaxQuant enables high peptide identification rates, individualized p.p.b.-range mass accuracies and proteome-wide protein quantification. Nat. Biotechnol. 2008;26:1367-1372.

Crooks G.E., Hon G., Chandonia J.M., Brenner S.E. WebLogo: a sequence logo generator. Genome Res. 2004;14:1188-1190.

Cunningham S., Piedra P.A., Martinon-Torres F., Szymanski H., Brackeva B., Dombrecht E., Detalle L., Fleurinck C. Nebulised ALX-0171 for respiratory syncytial virus lower respiratory tract infection in hospitalised children: a double-blind, randomised, placebo-controlled, phase 2b trial. Lancet Respir. Med. 2021;9:21-32.

Czajkowsky D.M., Hu J., Shao Z., Pleass R.J. Fc-fusion proteins: new developments and future perspectives. EMBO Mol. Med. 2012;4:1015-1028.

D Brooks B. The importance of epitope binning for biological drug discovery. Curr. Drug Discov. Tech. 2014;11:109-112.

Dong G.Q., Fan H., Schneidman-Duhovny D., Webb B., Sali A. Optimized atomic statistical potentials: assessment of protein interfaces and loops. Bioinformatics. 2013;29:3158-3166.

Durrum E.L., Jencks W.P., Smith E.R. The clinical significance of the analysis of serum protein distribution by filter paper electrophoresis. Am. J. Med. 1956;21:387-405.

Fernandez-Martinez J., Kim S.J., Shi Y., Upla P., Pellarin R., Gagnon M., Chemmama I.E., Wang J., Nudelman I., Zhang W. Structure and function of the nuclear pore complex cytoplasmic mRNA export platform. Cell. 2016;167:1215-1228.e25.

Finicle B.T., Jayashankar V., Edinger A.L. Nutrient scavenging in cancer. Nat. Rev. Cancer. 2018;18:619-633.

Fleming B.D., Urban D.J., Hall M.D., Longerich T., Greten T.F., Pastan I., Ho M. Engineered Anti-GPC3 Immunotoxin, HN3-ABD-T20, Produces regression in mouse liver cancer xenografts through prolonged serum retention. Hepatology. 2020;71:1696-1711.

Flyak A.I., Kuzmina N., Murin C.D., Bryan C., Davidson E., Gilchuk P., Gulka C.P., Ilinykh P.A., Shen X., Huang K. Broadly neutralizing antibodies from human survivors target a conserved site in the Ebola virus glycoprotein HR2-MPER region. Nat. Microbiol. 2018;3:670-677.

Fridy P.C., Li Y., Keegan S., Thompson M.K., Nudelman I., Scheid J.F., Oeffinger M., Nussenzweig M.C., FenyöD., Chait B.T. A robust pipeline for rapid production of versatile nanobody repertoires. Nat. Methods. 2014;11:1253-1260.

Fuchs H., Igney F. Binding to ocular albumin as a half-life extension principle for intravitreally injected drugs: evidence from mechanistic rat and rabbit studies. J. Ocul. Pharmacol. Ther. 2017;33:115-122.

Gallien S., Duriez E., Crone C., Kellmann M., Moehring T., Domon B. Targeted proteomic quantification on quadrupole-orbitrap mass spectrometer. Mol. Cell Proteomics. 2012;11:1709-1723.

Geyer P.E., Holdt L.M., Teupser D., Mann M. Revisiting biomarker discovery by plasma proteomics. Mol. Syst. Biol. 2017;13:942.

Ghuman J., Zunszain P.A., Petitpas I., Bhattacharya A.A., Otagiri M., Curry S. Structural basis of the drug-binding specificity of human serum albumin. J. Mol. Biol. 2005;353:38-52.

Greish K. Enhanced permeability and retention of macromolecular drugs in solid tumors: a royal gate for targeted anticancer nanomedicines. J. Drug Target. 2007;15:457-464.

Hamers-Casterman C., Atarhouch T., Muyldermans S., Robinson G., Hamers C., Songa E.B., Bendahman N., Hamers R. Naturally occurring antibodies devoid of light chains. Nature. 1993;363:446-448.

Harmsen M.M., De Haard H.J. Properties, production, and applications of camelid single-domain antibody fragments. Appl. Microbiol. Biotechnol. 2007;77:13-22.

Harris J.M., Chess R.B. Effect of pegylation on pharmaceuticals. Nat. Rev. Drug Discov. 2003;2:214-221.

Hassanzadeh-Ghassabeh G., Devoogdt N., De Pauw P., Vincke C., Muyldermans S. Nanobodies and their potential applications. Nanomedicine. 2013;8:1013-1026.

Heinrich L., Tissot N., Hartmann D.J., Cohen R. Comparison of the results obtained by ELISA and surface plasmon resonance for the determination of antibody affinity. J. Immunol. Methods. 2010;352:13-22.

Hirsch F.R., Varella-Garcia M., Cappuzzo F. Predictive value of EGFR and HER2 overexpression in advanced non-small-cell lung cancer. Oncogene. 2009;28(Suppl 1):S32-S37.

Hoefman S., Ottevaere I., Baumeister J., Sargentini-Maier M.L. Pre-clinical intravenous serum pharmacokinetics of albumin binding and non-half-life extended Nanobodies® Antibodies. 2015;4:141-156.

Holliger P., Hudson P.J. Engineered antibody fragments and the rise of single domains. Nat. Biotechnol. 2005;23:1126-1136.

Jovčevska I., Muyldermans S. The therapeutic potential of nanobodies. BioDrugs. 2020;34:11-26.

Kang T.H., Jung S.T. Boosting therapeutic potency of antibodies by taming Fc domain functions. Exp. Mol. Med. 2019;51:1-9.

Katzelnick L.C., Gresh L., Halloran M.E., Mercado J.C., Kuan G., Gordon A., Balmaseda A., Harris E. Antibody-dependent enhancement of severe dengue disease in humans. Science. 2017;358:929-932.

Khair D.O., Bax H.J., Mele S., Crescioli S., Pellizzari G., Khiabany A., Nakamura M., Harris R.J., French E., Hoffmann R.M. Combining immune checkpoint inhibitors: established and emerging targets and strategies to improve outcomes in melanoma. Front. Immunol. 2019;10:453.

Kijanka M., Dorresteijn B., Oliveira S., van Bergen en Henegouwen P.M.P. Nanobody-based cancer therapy of solid tumors. Nanomedicine (Lond) 2015;10:161-174.

Kim S.J., Fernandez-Martinez J., Nudelman I., Shi Y., Zhang W., Raveh B., Herricks T., Slaughter B.D., Hogan J.A., Upla P. Integrative structure and functional anatomy of a nuclear pore complex. Nature. 2018;555:475-482.

Kontermann R.E. Half-life extended biotherapeutics. Expert Opin. Biol. Ther. 2016;16:903-915.

Kratz F. Albumin as a drug carrier: design of prodrugs, drug conjugates and nanoparticles. J. Control Release. 2008;132:171-183.

Larios Mora A., Detalle L., Gallup J.M., Van Geelen A., Stohr T., Duprez L., Ackermann M.R. Delivery of ALX-0171 by inhalation greatly reduces respiratory syncytial virus disease in newborn lambs. MAbs. 2018;10:778-795.

Larsen M.T., Kuhlmann M., Hvam M.L., Howard K.A. Albumin-based drug delivery: harnessing nature to cure disease. Mol. Cell Ther. 2016;4:3.

(56) References Cited

OTHER PUBLICATIONS

Letunic I., Bork P. Interactive Tree of Life (iTOL): an online tool for phylogenetic tree display and annotation. Bioinformatics. 2007;23:127-128.

Liang W., Pan H.W., Vllasaliu D., Lam J.K.W. Pulmonary delivery of biological drugs. Pharmaceutics. 2020;12:1025. [PMC free article] [PubMed] [Google Scholar].

Low B.E., Wiles M.V. A humanized mouse model to study human albumin and albumin conjugates pharmacokinetics. Methods Mol. Biol. 2016;1438:115-122.

Mastronarde D.N., Held S.R. Automated tilt series alignment and tomographic reconstruction in IMOD. J. Struct. Biol. 2017;197:102-113.

Merlot A.M., Kalinowski D.S., Richardson D.R. Unraveling the mysteries of serum albumin-more than just a serum protein. Front. Physiol. 2014;5:299.

Moynihan K.D., Opel C.F., Szeto G.L., Tzeng A., Zhu E.F., Engreitz J.M., Williams R.T., Rakhra K., Zhang M.H., Rothschilds A.M. Eradication of large established tumors in mice by combination immunotherapy that engages innate and adaptive immune responses. Nat. Med. 2016;22:1402-1410.

Müller M.R., Saunders K., Grace C., Jin M., Piche-Nicholas N., Steven J., O'Dwyer R., Wu L., Khetemenee L., Vugmeyster Y. Improving the pharmacokinetic properties of biologics by fusion to an anti-HSA shark VNAR domain. MAbs. 2012;4:673-685.

Nambulli S., Xiang Y., Tilston-Lunel N.L., Rennick L.J., Sang Z., Klimstra W.B., Reed D.S., Crossland N.A., Shi Y., Duprex W.P. Inhalable nanobody (PiN-21) prevents and treats SARS-CoV-2 infections in Syrian hamsters at ultra-low doses. Sci. Adv. 2021;7:eabh0319.

Niesen F.H., Berglund H., Vedadi M. The use of differential scanning fluorimetry to detect ligand interactions that promote protein stability. Nat. Protoc. 2007;2:2212-2221.

Nivarthi U.K., Kose N., Sapparapu G., Widman D., Gallichotte E., Pfaff J.M., Doranz B.J., Weiskopf D., Sette A., Durbin A.P. Mapping the human memory B cell and serum neutralizing antibody responses to dengue virus serotype 4 infection and vaccination. J. Virol. 2017;91:e02016-e02041.

Ovacik M., Lin K. Tutorial on monoclonal antibody pharmacokinetics and its considerations in early development. Clin. Transl. Sci. 2018;11:540-552.

Overwijk W.W., Restifo N.P. B16 as a mouse model for human melanoma. Curr. Protoc. Immunol. 2001 Chapter 20, Unit 20.21.

Patton J.S., Byron P.R. Inhaling medicines: delivering drugs to the body through the lungs. Nat. Rev. Drug Discov. 2007;6:67-74.

Peterson A.C., Russell J.D., Bailey D.J., Westphall M.S., Coon J.J. Parallel reaction monitoring for high resolution and high mass accuracy quantitative, targeted proteomics. Mol. Cell Proteomics. 2012;11:1475-1488.

Pettersen E.F., Goddard T.D., Huang C.C., Couch G.S., Greenblatt D.M., Meng E.C., Ferrin T.E. Ucsf Chimera—a visualization system for exploratory research and analysis. J. Comput. Chem. 2004;25:1605-1612.

Pettersen E.F., Goddard T.D., Huang C.C., Meng E.C., Couch G.S., Croll T.I., Morris J.H., Ferrin T.E. UCSF ChimeraX: structure visualization for researchers, educators, and developers. Protein Sci. 2021;30:70-82.

Pleiner T., Bates M., Trakhanov S., Lee C.-T., Schliep J.E., Chug H., Böhning M., Stark H., Urlaub H., Görlich D. Nanobodies: site-specific labeling for super-resolution imaging, rapid epitope-mapping and native protein complex isolation. Elife. 2015;4:e11349.

Polack F.P., Hoffman S.J., Crujeiras G., Griffin D.E. A role for nonprotective complement-fixing antibodies with low avidity for measles virus in atypical measles. Nat. Med. 2003;9:1209-1213.

Pyzik M., Rath T., Lencer W.I., Baker K., Blumberg R.S. FcRn: the architect behind the immune and nonimmune functions of IgG and albumin. J. Immunol. 2015;194:4595-4603.

Ring A.M., Manglik A., Kruse A.C., Enos M.D., Weis W.I., Garcia K.C., Kobilka B.K. Adrenaline-activated structure of beta2-adrenoceptor stabilized by an engineered nanobody. Nature. 2013;502:575-579.

Roopenian D.C., Low B.E., Christianson G.J., Proetzel G., Sproule T.J., Wiles M.V. Albumin-deficient mouse models for studying metabolism of human albumin and pharmacokinetics of albumin-based drugs. MAbs. 2015;7:344-351.

Rosenberg S.A. IL-2: the first effective immunotherapy for human cancer. J. Immunol. 2014;192:5451-5458.

Rout M.P., Sali A. Principles for integrative structural biology studies. Cell. 2019;177:1384-1403.

Russel D., Lasker K., Webb B., Velazquez-Muriel J., Tjioe E., Schneidman-Duhovny D., Peterson B., Sali A. Putting the pieces together: integrative modeling platform software for structure determination of macromolecular assemblies. PLoS Biol. 2012;10:e1001244.

Sakamoto S., Putalun W., Vimolmangkang S., Phoolcharoen W., Shoyama Y., Tanaka H., Morimoto S. Enzyme-linked immunosorbent assay for the quantitative/qualitative analysis of plant secondary metabolites. J. Nat. Med. 2018;72:32-42.

Sand K.M.K., Bern M., Nilsen J., Noordzij H.T., Sandlie I., Andersen J.T. Unraveling the interaction between FcRn and albumin: opportunities for design of albumin-based therapeutics. Front. Immunol. 2015;5:1-21.

Scheres S.H. Relion: implementation of a Bayesian approach to cryo-EM structure determination. J. Struct. Biol. 2012;180:519-530.

Schmidt M.M., Townson S.A., Andreucci A.J., King B.M., Schirmer E.B., Murillo A.J., Dombrowski C., Tisdale A.W., Lowden P.A., Masci A.L. Crystal structure of an HSA/FcRn complex reveals recycling by competitive mimicry of HSA ligands at a pH-dependent hydrophobic interface. Structure. 2013;21:1966-1978.

Schneidman-Duhovny D., Inbar Y., Nussinov R., Wolfson H.J. PatchDock and SymmDock: servers for rigid and symmetric docking. Nucleic Acids Res. 2005;33:W363-W367.

Schneidman-Duhovny D., Wolfson H.J. Modeling of multimolecular complexes. Methods Mol. Biol. 2020;2112:163-174.

Schwartz R.N., Stover L., Dutcher J.P. Managing toxicities of high-dose interleukin-2. Oncology (Williston Park) 2002;16:11-20. Abstract.

Scully M., Cataland S.R., Peyvandi F., Coppo P., Knöbl P., Kremer Hovinga J.A., Metjian A., de la Rubia J., Pavenski K., Callewaert F. Caplacizumab treatment for acquired thrombotic thrombocytopeniaurpura. N. Engl. J. Med. 2019;380:335-346.

Shi Y., Fernandez-Martinez J., Tjioe E., Pellarin R., Kim S.J., Williams R., Schneidman-Duhovny D., Sali A., Rout M.P., Chait B.T. Structural characterization by cross-linking reveals the detailed architecture of a coatomer-related heptameric module from the nuclear pore complex. Mol. Cell Proteomics. 2014;13:2927-2943.

Shi Y., Pellarin R., Fridy P.C., Fernandez-Martinez J., Thompson M.K., Li Y., Wang Q.J., Sali A., Rout M.P., Chait B.T. A strategy for dissecting the architectures of native macromolecular assemblies. Nat. Methods. 2015;12:1135-1138.

Sievers F., Higgins D.G. Clustal Omega, accurate alignment of very large Nos. of sequences. Methods Mol. Biol. 2014;1079:105-116.

Sleep D., Cameron J., Evans L.R. Albumin as a versatile platform for drug half-life extension. Biochim. Biophys. Acta-General Subjects. 2013;1830:5526-5534.

Sproston N.R., Ashworth J.J. Role of C-reactive protein at sites of inflammation and infection. Front. Immunol. 2018;9:754.

Steel J.C., Waldmann T.A., Morris J.C. Interleukin-15 biology and its therapeutic implications in cancer. Trends Pharmacological Sciences. 2012;33:35-41.

Steeland S., Puimège L., Vandenbroucke R.E., Van Hauwermeiren F., Haustraete J., Devoogdt N., Hulpiau P., Leroux-Roels G., Laukens D., Meuleman P. Generation and characterization of small single domain antibodies inhibiting human tumor necrosis factor receptor 1. J. Biol. Chem. 2015;290:4022-4037.

Steeland S., Vandenbroucke R.E., Libert C. Nanobodies as therapeutics: big opportunities for small antibodies. Drug Discov. Today. 2016;21:1076-1113.

Sudlow G., Birkett D.J., Wade D.N. The characterization of two specific drug binding sites on human serum albumin. Mol. Pharmacol. 1975;11:824-832.

(56) References Cited

OTHER PUBLICATIONS

Sugio S., Kashima A., Mochizuki S., Noda M., Kobayashi K. Crystal structure of human serum albumin at 2.5 A resolution. Protein Eng. 1999;12:439-446.

Sun Z., Ren Z., Yang K., Liu Z., Cao S., Deng S., Xu L., Liang Y., Guo J., Bian Y. A next-generation tumor-targeting IL-2 preferentially promotes tumor-infiltrating CD8(+) T-cell response and effective tumor control. Nat. Commun. 2019;10:3874.

Tang G., Peng L., Baldwin P.R., Mann D.S., Jiang W., Rees I., Ludtke S.J. EMAN2: an extensible image processing suite for electron microscopy. J. Struct. Biol. 2007;157:38-46.

Terryn S., Francart A., Lamoral S., Hultberg A., Rommelaere H., Wittelsberger A., Callewaert F., Stohr T., Meerschaert K., Ottevaere I. Protective effect of different anti-rabies virus VHH constructs against rabies disease in mice. PLoS One. 2014;9:e109367.

Tijink B.M., Laeremans T., Budde M., Stigter-van Walsum M., Dreier T., de Haard H.J., Leemans C.R., van Dongen G.A.M.S. Improved tumor targeting of anti-epidermal growth factor receptor Nanobodies through albumin binding: taking advantage of modular Nanobody technology. Mol. Cancer Ther. 2008;7:2288-2297.

Uhlar C.M., Whitehead A.S. Serum amyloid A, the major vertebrate acute-phase reactant. Eur. J. Biochem. 1999;265:501-523.

Van Faassen H., Ryan S., Henry K.A., Raphael S., Yang Q., Rossotti M.A., Brunette E., Jiang S., Haqqani A.S., Sulea T. Serum albumin-binding V Hs with variable pH sensitivities enable tailored half-life extension of biologics. FASEB J. 2020;34:8155-8171.

Van Heeke G., Allosery K., De Brabandere V., De Smedt T., Detalle L., de Fougerolles A. Nanobodies® as inhaled biotherapeutics for lung diseases. Pharmacol. Ther. 2017;169:47-56.

Vincke C., Loris R., Saerens D., Martinez-Rodriguez S., Muyldermans S., Conrath K. General strategy to humanize a camelid single-domain antibody and identification of a universal humanized nanobody scaffold. J. Biol. Chem. 2009;284:3273-3284.

Vosjan M.J.W.D., Vercammen J., Kolkman J.A., Stigter-van Walsum M., Revets H., van Dongen G.A.M.S. Nanobodies targeting the hepatocyte growth factor: potential new drugs for molecular cancer therapy. Mol. Cancer Ther. 2012;11:1017-1025.

Webb B., Sali A. Comparative protein structure modeling using MODELLER. Curr. Protoc. Bioinformatics. 2014;47:5 6 1-32.

Weller M.G. Quality issues of research antibodies. Anal Chem. Insights. 2016;11:21-27.

Xiang Y., Nambulli S., Xiao Z., Liu H., Sang Z., Duprex W.P., Schneidman-Duhovny D., Zhang C., Shi Y. Versatile and multivalent nanobodies efficiently neutralize SARS-CoV-2. Science. 2020;370:1479-1484.

Xiang Y., Shen Z., Shi Y. Chemical cross-linking and mass spectrometric analysis of the endogenous yeast exosome complexes. Methods Mol. Biol. 2020;2062:383-400.

Xiang Y., Sang Z., Bitton L., Xu J., Liu Y., Schneidman-Duhovny D., Shi Y. Integrative proteomics identifies thousands of distinct, multi-epitope, and high-affinity nanobodies. Cell Syst. 2021;12:220-234.e9.

Yu C., Huang L. Cross-linking mass spectrometry: an emerging technology for interactomics and structural biology. Anal. Chem. 2018;90:144-165.

Zhu E.F., Gai S.A., Opel C.F., Kwan B.H., Surana R., Mihm M.C., Kauke M.J., Moynihan K.D., Angelini A., Williams R.T. Synergistic innate and adaptive immune response to combination immunotherapy with anti-tumor antigen antibodies and extended serum half-life IL-2. Cancer Cell. 2015;27:489-501.

International Preliminary Report on Patentability dated Sep. 15, 2022, issued for Application No. PCT/US2021/021094.

International Search Report and Written Opinion in PCT/US2021/021094. Mailed Jul. 22, 2021. 14 pages.

Hansen et al., Identification and Mapping of Linear Antibody Epitopes in Human Serum Albumin Using High-Intensity Peptide Arrays, PLos One. Jul. 23, 2014.

Partial Supplementary European Search Report mailed Mar. 6, 2024, issued in corresponding European Application No. 21764118.2, 14 pages.

Boutureira, O. et al. Advances in chemical protein modification. Chemical Reviews, 2015, 115: 2174-2195.

Khodabakhsh, F. et al. Single-Domain Antibodies or Nanobodies: A Class of Next-Generation Antibodies. International Reviews of Immunology 2018, vol. 37, No. 6, 316-322.

Kosobokova, E.N. et al. Overview of fusion tags for recombinant proteins. Biochemistry (Moscow), 2016, 81(3): 187-200.

McMahon, C. et al. Yeast surface display platform for rapid discovery of conformationally selective nanobodies. Nature Structural & Molecular Biology 2018, vol. 25, 289-296.

Van Vught, R. et al. Site-specific functionalization of proteins and their applications to therapeutic antibodies. Computational and Structural Biotechnology Journal, 2014, 9(14): 1-13.

Yu, K. et al. Synthetic fusion protein design and applications. Biotechnology Advances, 2015, 33: 155-164.

* cited by examiner e f g h
| DSS crosslinks | Distance (Å) |
|---|---|
| Nb80 (K66) - HSA (K372) | 6.3 |
| Nb80 (K77) - HSA (K414) | 16.4 |
| Nb80 (K77) - HSA (K475) | 22.5 |
| Nb80 (K77) - HSA (K378) | 27.1 |
| Nb13 (K66) - HSA (K4) | 11.1 |
| Nb13 (K66) - HSA (K12) | 18.4 |
| Nb29 (K77) - HSA (K564) | 25.4 |
i
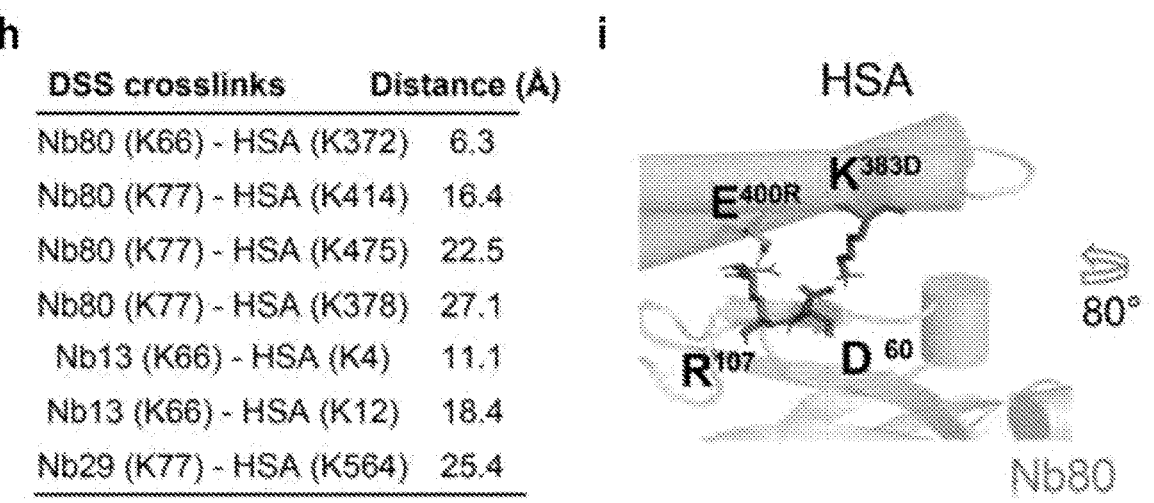
j
377                          401
YETTLEKCCAAADPHECYAKVFDEF
YEATLEDCCAKDDPHACYATVFDKL
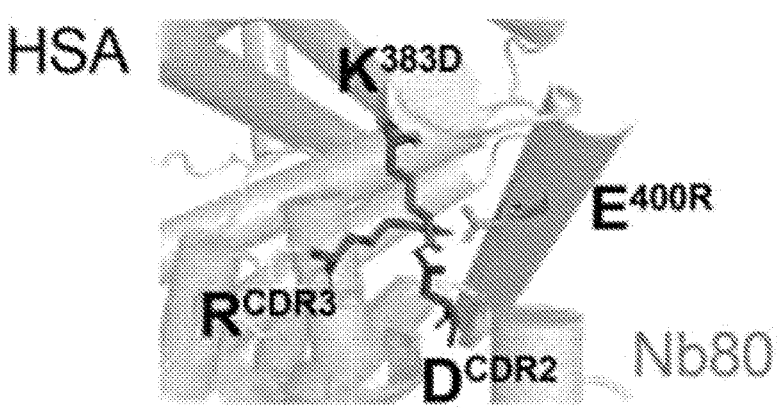
k
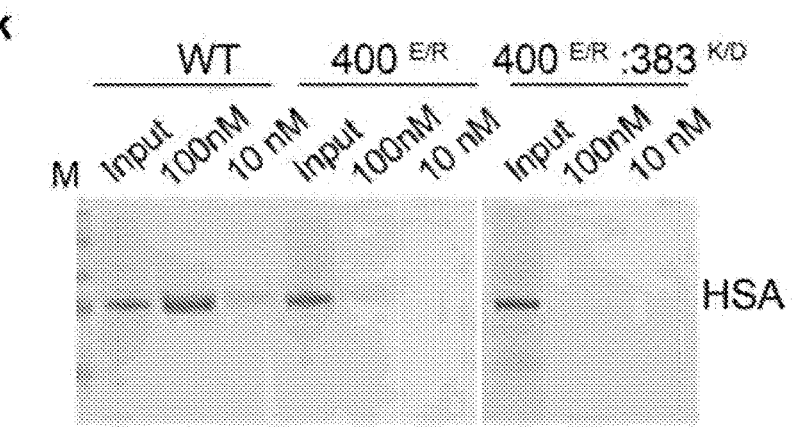
FIGS. 3h-3k a
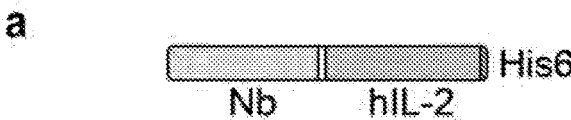
b
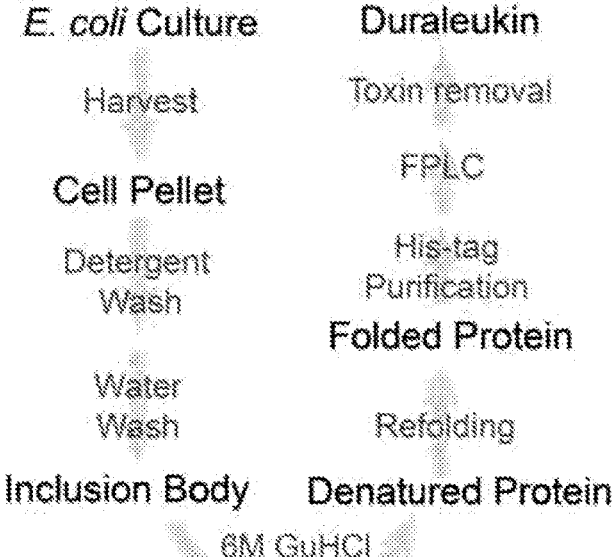
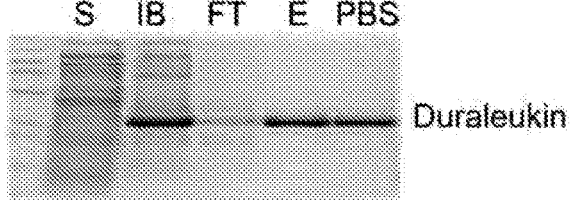
c
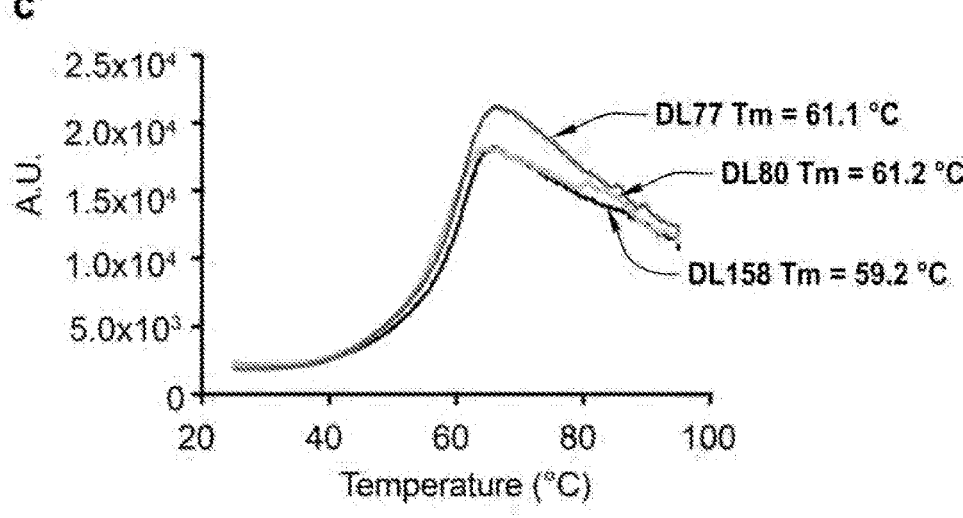
FIGS. 5a-5c

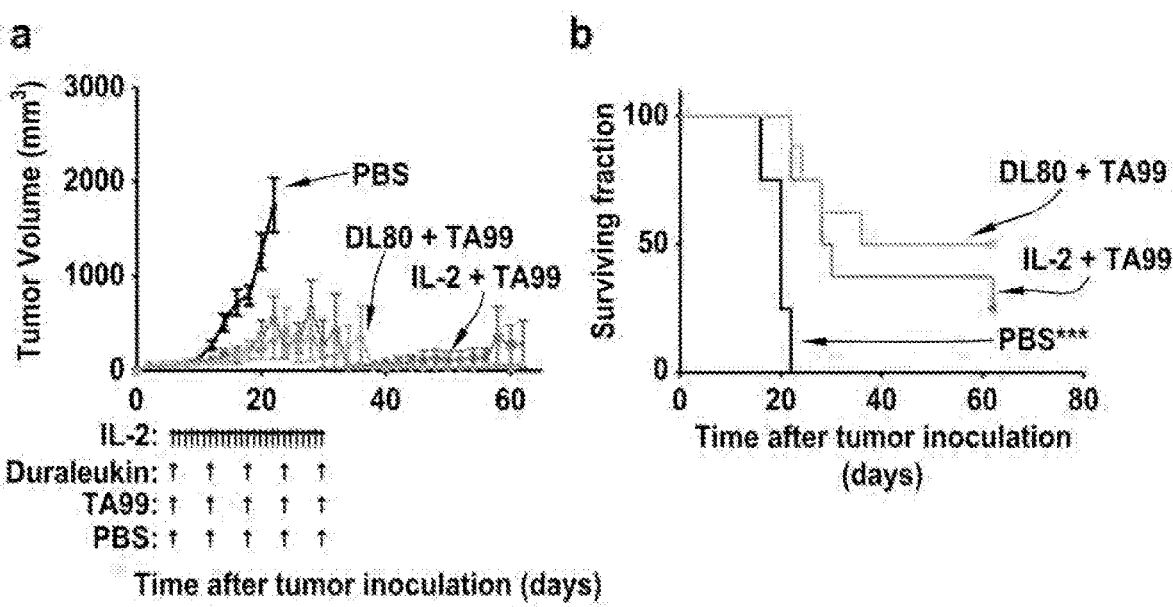
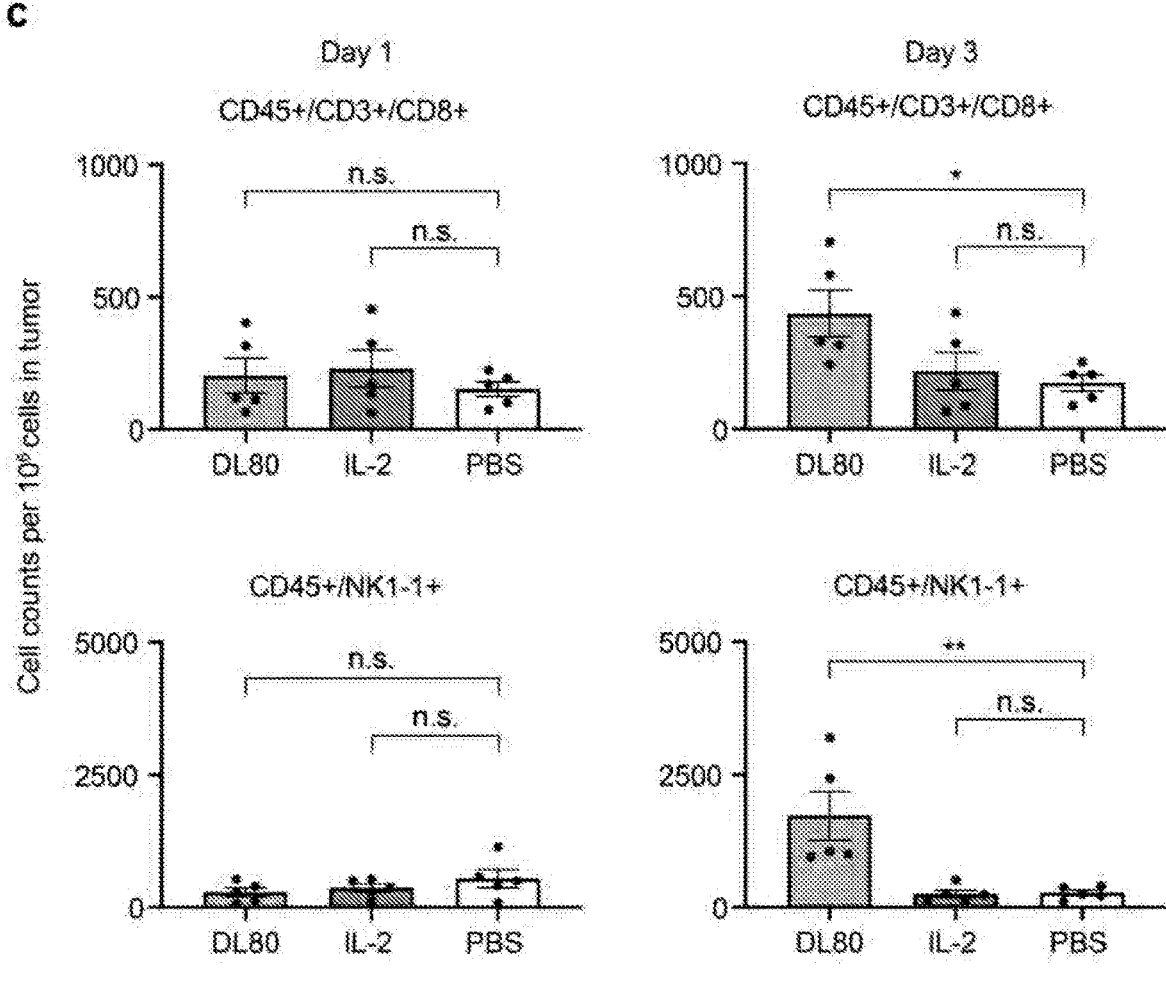
FIGS. 6a-6c

FIGS. 11a-11e a b c

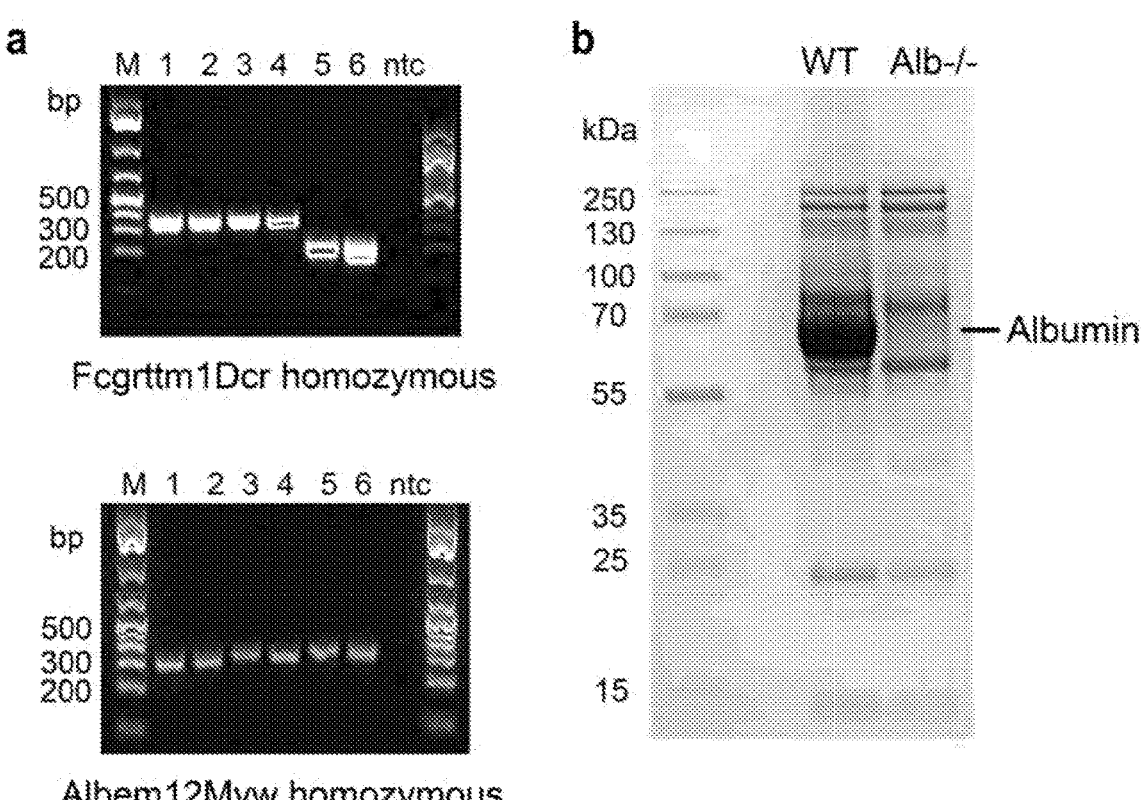
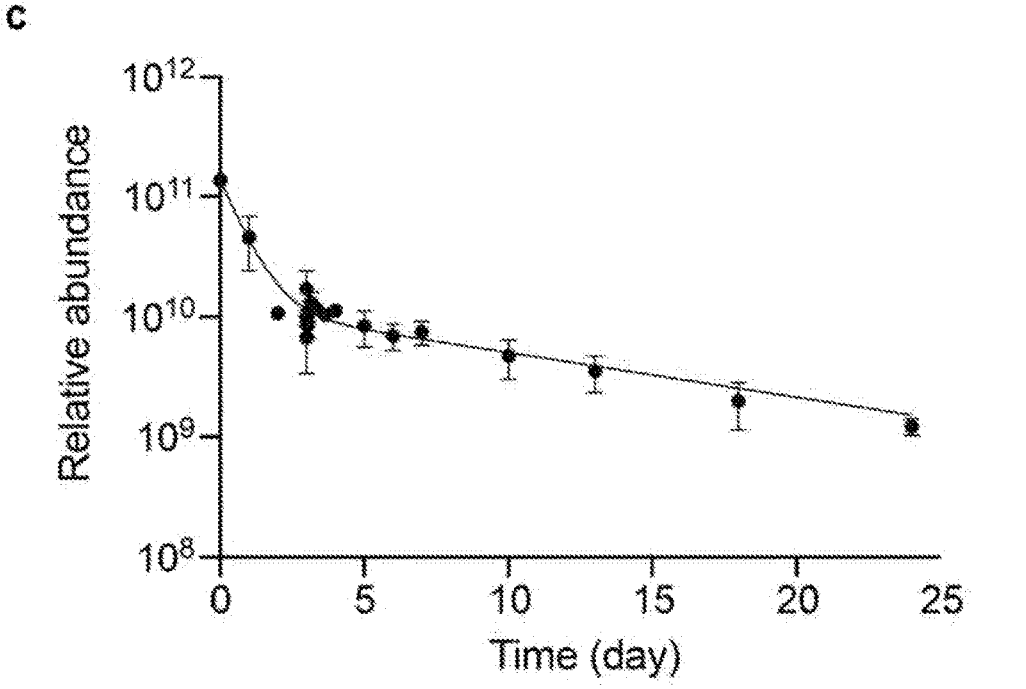
FIGS. 13a-13c

SERUM ALBUMIN BINDING NANOBODY COMPOSITIONS AND METHODS FOR USING THE SAME

CROSS-REFERENCE TO RELATED APPLICATIONS

This application is a United States National Phase Patent Application of International Patent Application Number PCT/US2021/021094, filed on Mar. 5, 2021, which claims the benefit of U.S. Provisional Application No. 62/986,180, filed Mar. 6, 2020, which are expressly incorporated herein by reference in their entireties.

FIELD

The present disclosure relates to human serum albumin binding nanobodies.

BACKGROUND

Nanobodies (Nbs) are minimal, intact and natural antigen-binding domains derived from camelid ungulates heavy-chain only antibodies ($V_HH$). Nbs are characterized by good solubility, thermostability, tissue penetration and potentially low toxicity to humans due to high sequence similarity with human IgG2/3; however, their therapeutic potentials are significantly limited by the short T1/2—typically less than a couple of hours. Small (approximately 15 kDa), devoid of heavy-light chain pairing and glycosylations, Nbs can be synthesized as recombinant DNA fragments for rapid, bulk production from *E. coli*. The ease of bioengineering of Nbs enables development of multi-functionality agents. Similar to IgGs, antigen-binding specificity of Nbs is primarily achieved by complementarity-determining regions (CDRs, 3 vs. 6 in IgG)-hypervariable loops in which CDR3 is the most variable "fingerprint". The CDR loops are presented by a robust tertiary core composed of four highly conserved framework regions. With smaller paratopes, it has been postulated that Nbs may have compromised affinity for antigen engagement. Several pilot structure studies show that Nbs can access "cryptic" epitopes-like cavities on the antigens, where IgGs may be inaccessible due to steric hindrance. Binding to these epitopes are achieved by both the small size and the "convex" shape that collectively facilitate insertion of CDR loop(s) into the grooves.

Although many Nbs have been developed for specific targets, the field still limited by the availability of high-quality and versatile Nb agents for drug delivery. While it is conceivable that solubility, thermostability, cross-species binding and robustness of bioengineering are critical, it remains unclear, whether and to what extent other biophysical, physicochemical and structural characteristics are important. Moreover, since biologics often have varied therapeutic windows, a sustainable, and fine-tuned add individualized half-life would be mostly desirable for maximizing drug efficacy while reducing side-effects. Systematic and comprehensive evaluation of these factors will help design the next generation agents for precision medicine.

Human serum albumin (HSA) is the most stable serum protein with a half-life of approximately 3 weeks. Unlike small molecules which are predominantly eliminated via glomerular filtration, HSA (67 kDa) cannot be directly cleared in the kidney. Continuously internalized, it forms a stable complex with cellular FeRn—a coreceptor for IgG. It has been shown that HSA can be efficiently recycled by the FcRn-mediated endocytosis, preventing the fast lysosomal degradation common for large serum proteins. While it remains unclear the local concentration(s) of HSA-FcRn interaction inside the endosome where the complex is recycled, resistance of endosomal acidic environment can be a prerequisite for successfully recycling of HSA and its stabilization.

However, HSA's interaction with Nbs has not been characterized, and there remains a need for effective nanobody therapies in many areas, including cytokine therapy. Cytokine therapy is an important component of immunomodulation. Interleukin-2 (IL-2) is a central immune cytokine that is crucial for the homeostasis and regulation of T cell activities. By stimulating the growth of cytotoxic T cells, IL-2 will upregulate immune responses and suppress tumor development. PROLEUKIN (aldesleukin, Novartis) is a recombinant form of the human interleukin-2 (IL-2) and the first approved cancer immunotherapy drug. IL-2 is used for the treatments of advanced melanoma and metastatic renal cell carcinoma. It has been reported that such treatments result in complete remission of as much as 10% of the patients bearing the metastatic tumors, sometimes without recurrence for up to 25 years Approximatively 70% of the patients with IL-2 treatments have a complete tumor regression. Major drawbacks of IL-2 however include its poor pharmacokinetics, low drug efficacy and high toxicity. Because of its small size (approximately 15 kDa), IL-2 is rapidly cleared from the circulation via glomerular filtration, with a median half-life of less than 30 minutes after administration in humans. As a result, high-dose and repetitive administration (as often as 7 hours per administration) is often required, which can lead to severe toxicity and side effects including the vascular leak syndrome.

For drug delivery, the availability of high-quality and versatile agents is limited. While it is conceivable that solubility, thermostability, cross-species binding and robustness of bioengineering are critical, it remains unclear, whether and to what extent other biophysical, physicochemical and structural characteristics are important. Moreover, since biologics often significantly vary in their therapeutic windows, a fine-tuned, sustainable, individualized half-life is mostly desirable for maximizing the drug potency while reducing side-effects.

Accordingly, what is needed are compositions and methods for maximizing the potency and half-life of therapeutic compositions, such as IL-2. The compositions and methods disclosed herein address these and other needs.

SUMMARY

In some aspects, disclosed herein is a recombinant nanobody that comprises a human serum albumin (HSA) binding polypeptide and an IL-2 polypeptide. In some embodiments, the HSA binding polypeptide specifically binds to an HSA epitope selected from the group consisting of epitope 1, epitope 2, epitope 3, and epitope 4, wherein epitope 1 comprises the amino acid residues 298-307, 311, 332-341, and 371-386 of SEQ ID NO: 1, wherein epitope 2 comprises the amino acid residues 5-13, 62-67, 93-99, and 228-266 of SEQ ID NO: 1, wherein epitope 3 comprises the amino acid residues 226-230 and 298-337 of SEQ ID NO: 1, and wherein epitope 4 comprises the amino acid residues 33-38 and 111-145 of SEQ ID NO: 1. In some embodiments, the HSA binding polypeptide comprises an amino acid sequence selected from the group consisting of SEQ ID NO: 2, SEQ ID NO: 3, and SEQ ID NO: 4. Also disclosed herein is a nanobody that comprises a human serum albumin (HSA) binding polypeptide, wherein the HSA binding polypeptide comprises a complementarity determining region (CDR)3, wherein the CDR3 comprises an amino acid sequence having at least 50% similarity to any of SEQ ID NOs: 10-100. In some embodiments, the recombinant nanobodies disclosed herein is less than 50 kDa in size. In some embodiments, the nanobody further comprises an IL-2 polypeptide. Such nanobodies can surprisingly improve the stability of IL-2 polypeptide while does not significantly decrease the affinity between the IL-2 polypeptide of the nanobody and an IL-2 receptor.

It is shown herein that administering the recombinant nanobody disclosed herein can decrease tumor volume and improve survival rate in a subject receiving the treatment. Accordingly, in some aspects, disclosed herein is a method of treating a cancer in a subject in need thereof, comprising administering a therapeutically effective amount of a recombinant nanobody comprising a human serum albumin (HSA) binding polypeptide and an IL-2 polypeptide.

DESCRIPTION OF DRAWINGS

FIGS. 1(a-h) show identification and characterization of HSA-Nbs. FIG. 1e shows correlation between ELISA OD and KD affinity by SPR.

FIGS. 2(a-d) show structural docking and cross-linking of HSA-Nb complexes.

FIGS. 3(a-k) show integrative structural characterization of a tetrameric HSA-Nb complex. FIG. 3h is the summary of cross-link satisfactions to the model. FIGS. 3i to 3k show site-directed mutagenesis analysis of two charged residues (K383 and D400) that form crossed, stable salt bridges with the corresponding residues on Nb80.

FIGS. 4(a-d) show high-throughput Nb pharmacokinetics in a humanized mouse model.

FIGS. 5(a-g) show development of Duraleukin—a novel class of Nb-fusion cytokine. FIG. 5a depicts schematic design of Duraleukin. FIG. 5b shows a protocol for Duraleukin production. FIG. 5c shows thermostability of Duraleukins by differential scanning fluorimetry.

FIGS. 6(a-c) show evaluation of the in vivo efficacy of Duraleukin in a melanoma mouse model. FIG. 6a shows the tumor growth curve. C57BL/6J mice bearing subcutaneous B16F10 tumors were treated with a combination of TA99 and Duraleukin or hIL-2 (n=8) with different doses/intervals. PBS treatment was used for control. FIG. 6b shows animal survival curve after treatment. FIG. 6c shows flow cytometry analysis of tumor-infiltrating immune cells.

FIGS. 7(a-r) (counted Nb100 and 113) show the Surface Plasmon Resonance (SPR) measurements of representative HSA Nbs. Ka (on rate), Kd (off rate) and affinity $K_D$ were documented.

FIGS. 8(a-t) show the thermostability $T_m$ of the representative HSA Nbs. The measurements were performed by differential scanning fluorimetry (DSF).

FIGS. 10(a-d) show the purification and negative-stain electron microscopy (EM) particle selection of the tetrameric Nb-HSA complex. FIG. 10b shows Nb80-Nb13-Nb29-HSA complex; FIG. 10c shows MBP-Nb80-Nb13-Nb29-MBP-HSA complex; FIG. 10d shows HSA.

Figures 11A, 11B, 11C, 11D, 11E:
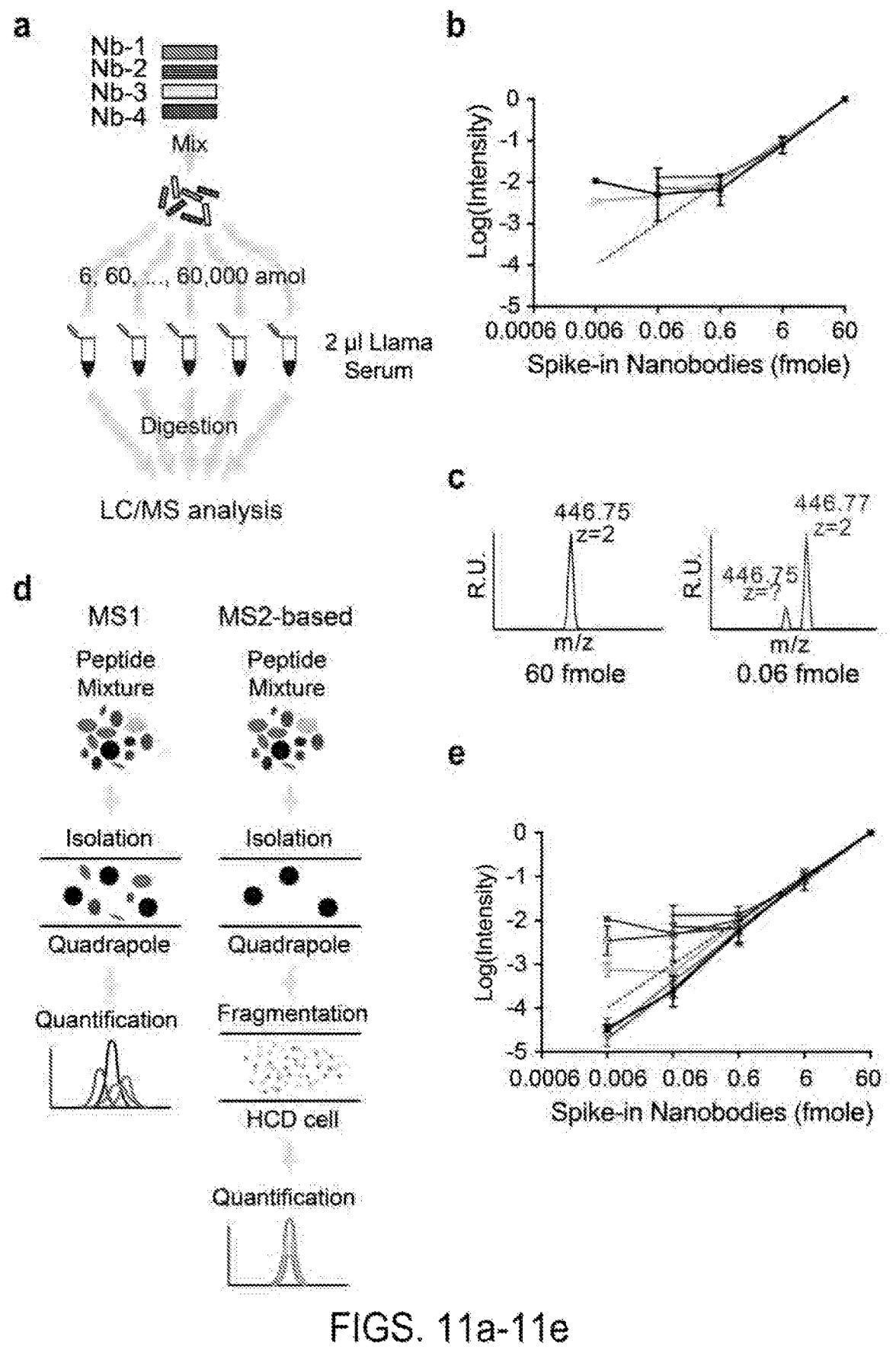

FIGS. 11(a-e) show the schematics of a novel fragment-ion-based method for multiplexed quantification of Nb PKs. FIG. 11a is a schematic of the digestion and LC/MS analysis steps. FIG. 11b is a chart showing spike-in nanobodies wherein dark squares designate Nb1-MS1, dark circles designate Nb2-MS1, light squares designate Nb3-MS1, and light circles indicate Nb4-MS1. FIG. 11c is a chart showing. FIG. 11d is a schematic of the isolation, quadrapole, fragmentation, HCD Cell and quantification steps. FIG. 11e is a chart showing spike-in nanobodies where darkened circles designate Nb1-PRM, darkened squares designate Nb1-MS1, darkened upside down triangles designate Nb2-PRM, darkened circles designate Nb2-MS1, open circles designate Nb3-PRM, open squares designate Nb3-MS1, open right side up triangles designate Nb4-PRM, open upside down triangles designate Nb4-MS1.

FIGS. 13(a-c) show the verification of B6.Cg-Tg (FCGRT) 32Der Alb$^{em12Mvw}$ Fcgrt$^{tm1Dcr}$/MvwJ mouse model. FIG. 13a shows the verification of Albem 12Mvw homozygous mice by DNA electrophoresis. FIG. 13b shows Fcgrttm1Dcr homozygous mice by Sanger sequencing and SDS-PAGE analysis. FIG. 13c shows the pharmacokinetics (PK) of HSA in the mouse model. Half-life (slow)=8.08 (day); half-life (fast)=0.53 (day); R2=0.9547. Half life (slow)=8.08 (day); half life (fast)=0.53 (day); R2=0.9547.

DETAILED DESCRIPTION

Figure 1A:
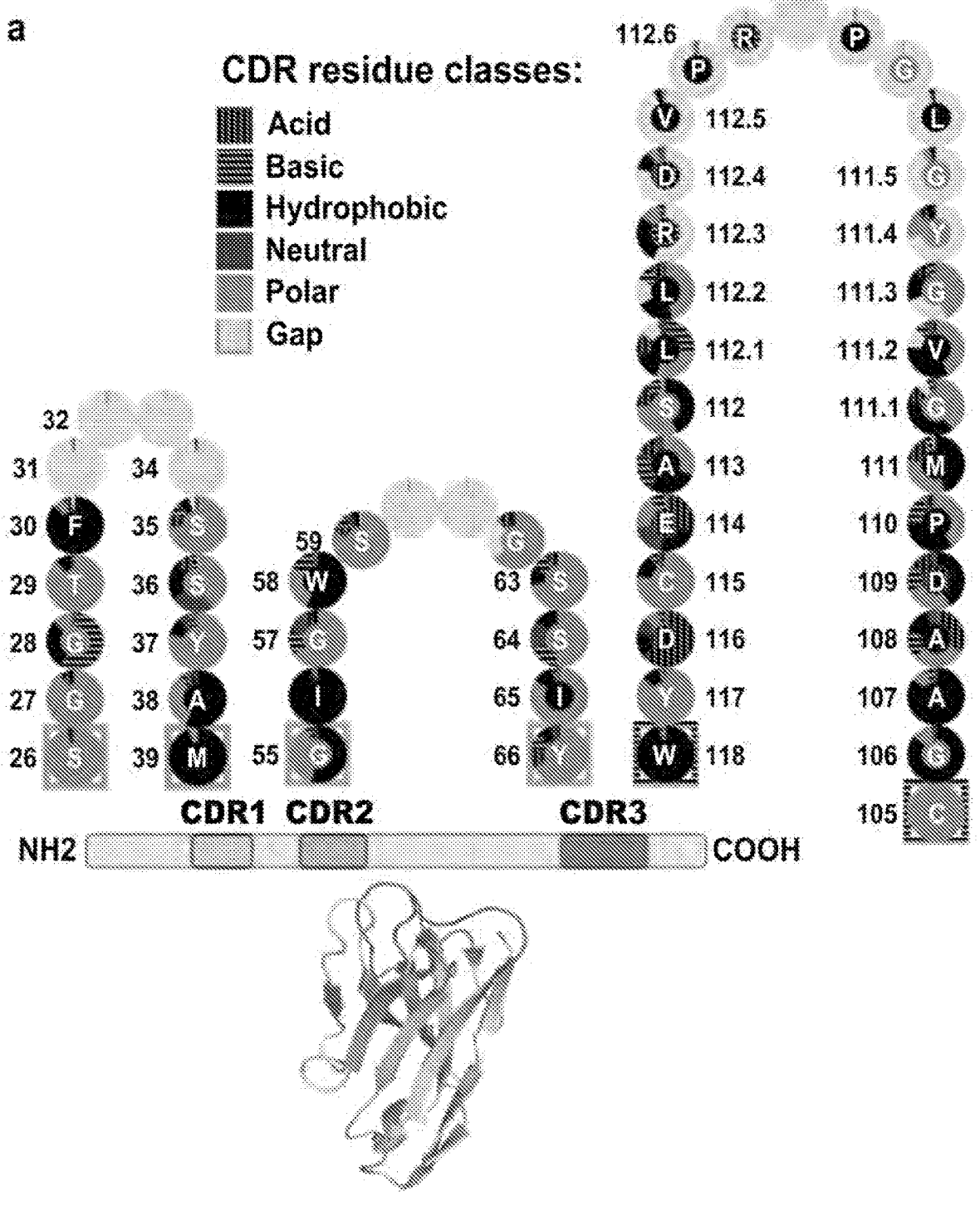
FIG. 1a shows schematic structure and amino acid composition of HSA-Nbs.

Recently, by using camelid immunization and an integrative proteomics pipeline, a large repertoire of nanobodies (Nbs) for HSA binding were identified. Here, a cohort of high-quality HSA-Nbs were expressed and systematically characterized using multidisciplinary approaches. In some embodiments, several HSA-Nbs were combined with cytokine human IL-2, developing highly stable compositions, collectively referred to as "Duraleukins," that can be used for melanoma treatment in a mouse model.

Duraleukins have been described with four outstanding features:

First, ease of production and manufacture. The Nb fusion of IL-2 (Duraleukins) have been demonstrated herein to be easily produced in bulk as highly purified, intact and functional proteins in bacteria, e.g., in E. coli cells. Note large administration dose of IL-2 (PROLEUKIN (aldesleukin, Novartis)) is a perquisite for its drug efficacy. In contrast, production of ALBULEUKIN (Human Genome Sciences) is mainly restricted in the rather expensive mammalian cells which limits its practical utility.

Second, ease of bioengineering. Bioengineering of Duraleukins is straightforward and simple. In one example, fusing another polypeptide drug at the C terminus can make a "trifunctionality drug". This is in sharp contrast with ALBULEUKIN (Human Genome Sciences) where bioengineering could be very challenging.

Third, outstanding flexibility and different in vivo half-lives for optimized/tailored drug development and clinical applications. Using a humanized albumin mouse model, it is demonstrated herein that different albumin Nbs have different in vivo pharmacokinetics (PK). This indicates that different Duraleukins with different HSA can have unique PKs which can be utilized to optimize the drug efficacy and to minimize the side effects of the drug, which are the major issues of the commercial drug PROLEUKIN (aldesleukin, Novartis).

Fourth, superior potency. The recombinant polypeptides inherit the outstanding physicochemical properties of Nbs such as thermostability and resistance (almost immune) to serum protease activities. Three times smaller than ALBULEUKIN (Human Genome Sciences) (30 kDa vs. 90 kDa), Duraleukins are structurally sound and retain the full functionality of the carrier protein IL-2. Due to their small sizes, Duraleukins can easily reach maximum effective molar concentration for drug administration since there is a limited drug uptake capacity. Fusing with a small intact domain of Nb (15 kDa) does not significantly affect the interaction between IL-2 and its receptor FcRN complexes, while a large recombinant protein like ALBULEUKIN (Human Genome Sciences) can be affected by structural steric hindrance, especially when it comes to the rather large bulky IL-2 receptor complexes.

Accordingly, disclosed herein are compositions that improve the stability and/or effectiveness of IL-2 in treating diseases (e.g., cancer), wherein the compositions are recombinant nanobodies that comprises a human serum albumin (HSA) binding polypeptide and an IL-2 polypeptide. In some embodiments, the recombinant nanobody increases the half-life of IL-2 compared to a natural or recombinant IL-2 polypeptide. Administering the recombinant nanobody comprising a human serum albumin (HSA) binding polypeptide and an IL-2 polypeptide surprisingly decreases tumor volume and improves survival rate in a subject receiving the treatment.

Terms used throughout this application are to be construed with ordinary and typical meaning to those of ordinary skill in the art. However, Applicants desire that the following terms be given the particular definition as provided below.

Terminology

As used in the specification and claims, the singular form "a," "an," and "the" include plural references unless the context clearly dictates otherwise. For example, the term "a cell" includes a plurality of cells, including mixtures thereof.

The term "about" as used herein when referring to a measurable value such as an amount, a percentage, and the like, is meant to encompass variations of ±20%, ±10%, ±5%, or ±1% from the measurable value.

"Administration" to a subject or "administering" includes any route of introducing or delivering to a subject an agent. Administration can be carried out by any suitable route, including oral, intravenous, intraperitoneal, intranasal, inhalation and the like. Administration includes self-administration and the administration by another.

The terms "antibody" and "antibodies" are used herein in a broad sense and include polyclonal antibodies, monoclonal antibodies, and bi-specific antibodies. In addition to intact immunoglobulin molecules, also included in the term "antibodies" are fragments or polymers of those immunoglobulin molecules, and human or humanized versions of immunoglobulin molecules or fragments thereof. Antibodies are usually heterotetrameric glycoproteins of about 150,000 daltons, composed of two identical light (L) chains and two identical heavy (H) chains. Each heavy chain has at one end a variable domain ($V_H$) followed by a number of constant domains Each light chain has a variable domain at one end ($V_L$) and a constant domain at its other end.

The antibodies can be tested for their desired activity using the in vitro assays described herein, or by analogous methods, after which, their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The terms "antigenic determinant" and "epitope" may also be used interchangeably herein, referring to the location on the antigen or target recognized by the antigen-binding molecule (such as the nanobodies of the invention). Epitopes can be formed both from contiguous amino acids (a "linear epitope") or noncontiguous amino acids juxtaposed by tertiary folding of a protein. The latter epitope, one created by at least some noncontiguous amino acids, is described herein as a "conformational epitope." An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The terms "antigen binding site", "binding site" and "binding domain" refer to the specific elements, parts or amino acid residues of a polypeptide, such as a nanobody, that bind the antigenic determinant or epitope.

The word "cancer" refers to cells which exhibit relatively autonomous growth, so that they exhibit an aberrant growth phenotype characterized by a significant loss of control of cell proliferation (i.e., de-regulated cell division). Cancer cells can be malignant or benign. Examples of various cancers include but are not limited to, melanoma, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In some embodiments, the cancer is melanoma. In some embodiments, the cancer is kidney cancer.

The terms "CDR" and "complementarity determining region" are used interchangeably and refer to a part of the variable chain of an antibody that participates in binding to an antigen. Accordingly, a CDR is a part of, or is, an "antigen binding site." In some embodiments, the nanobody comprises three CDR that collectively form an antigen binding site.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

"Composition" refers to any agent that has a beneficial biological effect. Beneficial biological effects include both therapeutic effects, e.g., treatment of a disorder or other undesirable physiological condition, and prophylactic effects, e.g., prevention of a disorder or other undesirable physiological condition. The terms also encompass pharmaceutically acceptable, pharmacologically active derivatives of beneficial agents specifically mentioned herein, including, but not limited to, a bacterium, a vector, polynucleotide, cells, salts, esters, amides, proagents, active metabolites, isomers, fragments, analogs, and the like. When the terms "composition" is used, then, or when a particular composition is specifically identified, it is to be understood that the term includes the composition per se as well as pharmaceutically acceptable, pharmacologically active vector, polynucleotide, salts, esters, amides, proagents, conjugates, active metabolites, isomers, fragments, analogs, etc. In some aspects, the composition disclosed herein comprises a recombinant polypeptide comprising a human serum albumin (HSA) binding polypeptide and an IL-2 polypeptide.

"Effective amount" encompasses, without limitation, an amount that can ameliorate, reverse, mitigate, prevent, or diagnose a symptom or sign of a medical condition or disorder (e.g., cancer). Unless dictated otherwise, explicitly or by context, an "effective amount" is not limited to a minimal amount sufficient to ameliorate a condition. The severity of a disease or disorder, as well as the ability of a treatment to prevent, treat, or mitigate, the disease or disorder can be measured, without implying any limitation, by a biomarker or by a clinical parameter. In some embodiments, the term "effective amount of a recombinant nanobody" refers to an amount of a recombinant nanobody sufficient to prevent, treat, or mitigate a cancer.

The "fragments" or "functional fragments," whether attached to other sequences or not, can include insertions, deletions, substitutions, or other selected modifications of particular regions or specific amino acids residues, provided the activity of the fragment is not significantly altered or impaired compared to the nonmodified peptide or protein. These modifications can provide for some additional property, such as to remove or add amino acids capable of disulfide bonding, to increase its bio-longevity, to alter its secretory characteristics, etc. In any case, the functional fragment must possess a bioactive property, such as binding to HSA and/or ameliorating cancer.

The "half-life" of an amino acid sequence, compound or polypeptide of the invention can generally be defined as the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of a nanobody, amino acid sequence, compound or polypeptide of the invention can be determined in any manner known, such as by pharmacokinetic analysis. these, for example, Kenneth, A et al., Chemical Stability of Pharmaceuticals: A Handbook for Pharmacists; Peters et al., Pharmacokinete analysis: A Practical Approach (1996); "Pharmacokinetics", M Gibaldi & D Perron, published by Marcel Dekker, 2nd Rev. edition (1982).

The term "identity" or "homology" shall be construed to mean the percentage of nucleotide bases or amino acid residues in the candidate sequence that are identical with the bases or residues of a corresponding sequence to which it is compared, after aligning the sequences and introducing gaps, if necessary to achieve the maximum percent identity for the entire sequence, and not considering any conserva- tive substitutions as part of the sequence identity. A poly- nucleotide or polynucleotide region (or a polypeptide or polypeptide region) that has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software pro- grams known in the art. Such alignment can be provided using, for instance, the method of Needleman et al. (1970) J. Mol. Biol. 48:443-453, implemented conveniently by computer programs such as the Align program (DNAstar, Inc.).

The term "increased" or "increase" as used herein gen- erally means an increase by a statically significant amount; for the avoidance of any doubt, "increased" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a refer- ence level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the terms "nanobody", "$V_H H$", "VAH antibody fragment" and "single domain antibody" are used indifferently and designate a variable domain of a single heavy chain of an antibody of the type found in Camelidae, which are without any light chains, such as those derived from Camelids as described in PCT Publication No. WO 94/04678, which is incorporated by reference in its entirety.

As used herein, "operatively linked" refers to the arrange- ment of polypeptide segments within a single polypeptide chain, where the individual polypeptide segments can be, without limitation, a protein, fragments thereof, linking peptides, and/or signal peptides. The term operatively linked can refer to direct fusion of different individual polypeptides within the single polypeptides or fragments thereof where there are no intervening amino acids between the different segments as well as when the individual polypeptides are connected to one another via a "linker" that comprises one or more intervening amino acids.

The term "reduced", "reduce", "reduction", or "decrease" as used herein generally means a decrease by a statistically significant amount. However, for avoidance of doubt, "reduced" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e., absent level as compared to a reference sample), or any decrease between 10-100% as compared to a reference level.

The term "nucleic acid" as used herein means a polymer composed of nucleotides, e.g. deoxyribonucleotides (DNA) or ribonucleotides (RNA). The terms "ribonucleic acid" and "RNA" as used herein mean a polymer composed of ribo- nucleotides. The terms "deoxyribonucleic acid" and "DNA" as used herein mean a polymer composed of deoxyribo- nucleotides.

The terms "polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limit- ing examples of polynucleotides: a gene or gene fragment, exons, introns, messenger RNA (mRNA), transfer RNA, ribosomal RNA, ribozymes, cDNA, recombinant polynucle- otides, branched polynucleotides, plasmids, vectors, isolated DNA of any sequence, isolated RNA of any sequence, nucleic acid probes, and primers. A polynucleotide may comprise modified nucleotides, such as methylated nucleo- tides and nucleotide analogs. If present, modifications to the nucleotide structure may be imparted before or after assem- bly of the polymer. The sequence of nucleotides may be interrupted by non-nucleotide components. A polynucle- otide may be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

"Pharmaceutically acceptable carrier" (sometimes referred to as a "carrier") means a carrier or excipient that is useful in preparing a pharmaceutical or therapeutic compo- sition that is generally safe and non-toxic, and includes a carrier that is acceptable for veterinary and/or human phar- maceutical or therapeutic use. The terms "carrier" or "phar- maceutically acceptable carrier" can include, but are not limited to, phosphate buffered saline solution, water, emul- sions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations con- taining these materials is described in, e.g., *Remington's Pharmaceutical Sciences,* 21st Edition, ed. University of the Sciences in Philadelphia, Lippincott, Williams & Wilkins, Philadelphia, PA, 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc., Bridgewater, New Jersey), polyethylene glycol (PEG), and PLURONICS™ (BASF; Florham Park, NJ). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

"Recombinant" used in reference to a polypeptide refers herein to a combination of two or more polypeptides, which combination is not naturally occurring.

The term "specificity" refers to the number of different types of antigens or antigenic determinants to which a particular antigen-binding molecule (such as the nanobody of the invention) can bind. A nanobody with low specificity binds to multiple different epitopes via a single antigen binding site or binding domain, whereas a nanobody with high specificity binds to one or a few epitopes via a single antigen binding site or binding domain. In some embodiments, the few epitopes are similar or highly similar, such as, for example, cross-species epitopes. As used herein, the term "specifically binds," as used herein with respect to a nanobody refers to the nanobody's preferential binding to an epitope as compared with other epitopes. Specific binding can depend upon binding affinity and the stringency of the conditions under which the binding is conducted. In one example, a nanobody specifically binds an epitope when there is high affinity binding under stringent conditions. In some embodiments, the HSA binding polypeptide or nanobody described herein specifically binds to human serum albumin.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

"Therapeutically effective amount" refers to the amount of a composition such as recombinant nanobody comprising a human serum albumin (HSA) binding polypeptide and an IL-2 polypeptide that will elicit the biological or medical response of a tissue, system, animal, or human that is being sought by the researcher, veterinarian, medical doctor or other clinician over a generalized period of time. In some embodiments, a desired response is reduction of tumor size, mitigation of cancer (e.g., melanoma) and/or related symptoms. In other embodiments, a desired response is an increase in anti-tumor immune response, including, for examples, activation of anti-tumor cytotoxic T lymphocytes, natural killer cells, and/or B cells, and/or increased levels of tumor antigen-specific antibodies in the subject. In some instances, a desired biological or medical response is achieved following administration of multiple dosages of the composition to the subject over a period of days, weeks, or years. The therapeutically effective amount will vary depending on the composition, the disorder or conditions and its severity, the route of administration, time of administration, rate of excretion, drug combination, judgment of the treating physician, dosage form, and the age, weight, general health, sex and/or diet of the subject to be treated. The therapeutically effective amount of recombinant nanobody comprising a human serum albumin (HSA) binding polypeptide and an IL-2 polypeptide as described herein can be determined by one of ordinary skill in the art.

A therapeutically significant reduction in a symptom is, e.g., at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject. Measured or measurable parameters include clinically detectable markers of disease, for example, elevated or depressed levels of a biological marker, such as decreased tumor sizes, increase in anti-tumor immune responses, including, for examples, activation of anti-tumor cytotoxic T lymphocytes, natural killer cells, and/or B cells, increased levels of tumor antigen-specific antibodies in circulation and/or a tumor of a subject, and/or prolonged survival of a subject. It will be understood, that the total daily usage of the compositions and formulations as disclosed herein will be decided by the attending physician within the scope of sound medical judgment. The exact amount required will vary depending on factors such as the type of disease being treated.

The terms "treat," "treating," "treatment," and grammatical variations thereof as used herein, include partially or completely delaying, alleviating, mitigating or reducing the intensity of one or more attendant symptoms of a cancer or condition and/or alleviating, mitigating or impeding one or more causes of a cancer Treatments according to the invention may be applied preventively, prophylactically, palliatively or remedially. In some embodiments, the treatment is a reduction in a tumor size. In some embodiments, the treatment is a reduction of cancer metastasis or cancer lesions. In some embodiments, the treatment is a reduction in a tumor number.

Prophylactic compositions are administered to a subject prior to onset (e.g., before obvious signs of a cancer), during early onset (e.g., upon initial signs and symptoms of a cancer), after an established development of a cancer, or at the late stage of a cancer. Prophylactic administration can occur for several minutes to months prior to the manifestation of a cancer.

Compositions

Disclosed herein are a recombinant nanobodies comprising a human serum albumin (HSA) binding polypeptide and an IL-2 polypeptide, wherein the HSA binding polypeptide specifically binds to an HSA epitope. As discussed above, this group of recombinant nanobodies have been shown herein to be surprisingly effective at prolonging the half-life of the IL-2 polypeptide. In some embodiments, the affinity between the IL-2 polypeptide of the nanobody and an IL-2 receptor is not significantly decreased or not decreased as compared to an IL-2 that is not a part of or joined to the nanobody.

With regard to the human serum albumin portion of the nanobody, "serum albumin" is a type of globular protein in vertebrate blood. Serum albumin is produced by the liver. "Human serum albumin" or "HSA" refers herein to a polypeptide that synthesizes and hydrolyzes cyclic adenosine 5'-diphosphate-ribose, and is encoded by the ALB gene. In some embodiments, the HSA polypeptide is that identified in one or more publicly available databases as follows: HGNC: 399, Entrez Gene. 213, Ensembl: ENSG00000163631, OMIM: 103600, UniProtKB. P02768. In some embodiments, the HSA polypeptide comprises the sequence of SEQ ID NO: 1, or a polypeptide sequence having at or greater than about 80%, about 85%, about 90%, about 95%, or about 98% homology with SEQ ID NO: 1, or a polypeptide comprising a portion of SEQ ID NO: 1. The HSA polypeptide of SEQ ID NO: 1 may represent an immature or pre-processed form of mature HSA, and accordingly, included herein are mature or processed portions of the HSA polypeptide in SEQ ID NO: 1.

Figure 16:
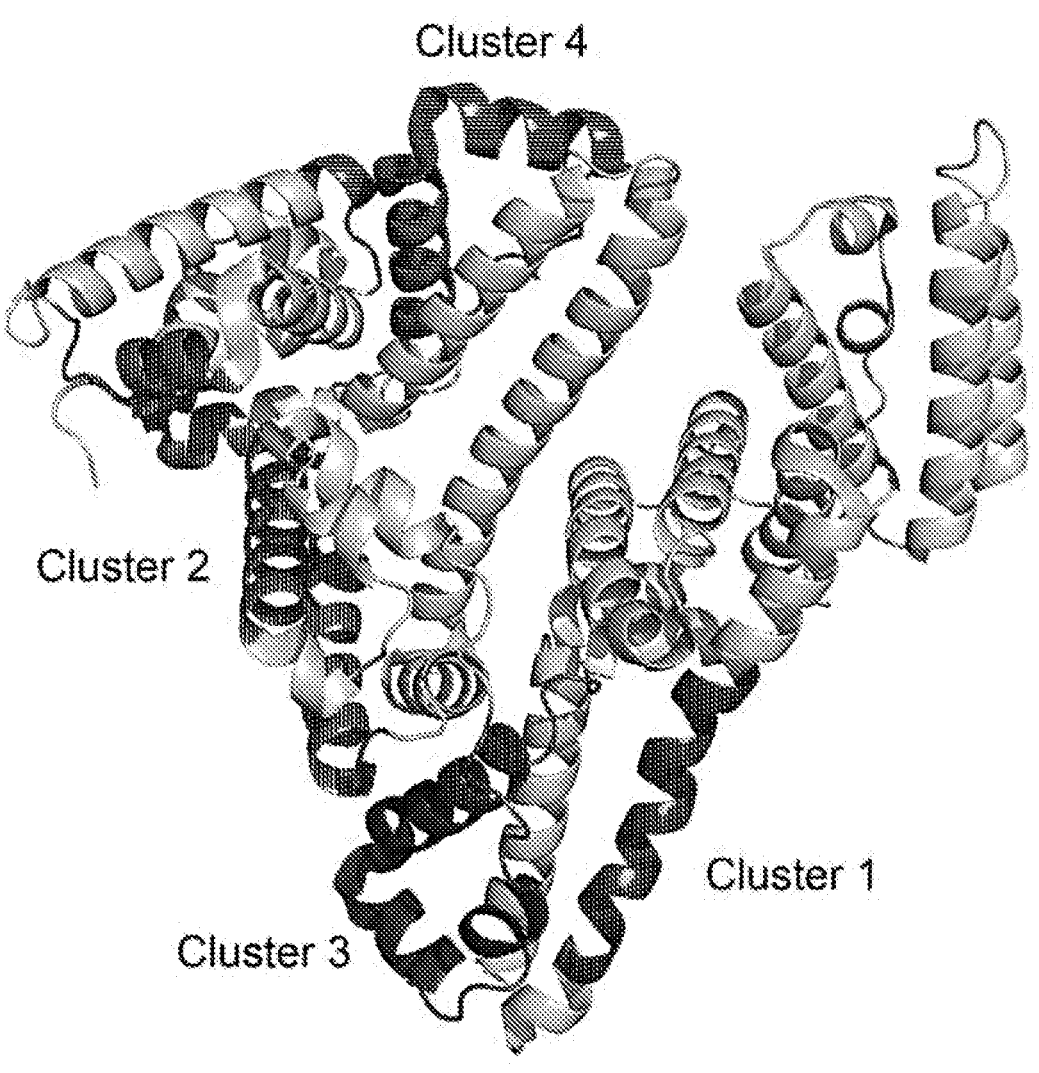
FIG. 16 shows four clusters on HSA where the Nb-binding epitopes locate. Cluster 1 (Nb80): 298-307, 311, 332-341, and 371-386 (aa); cluster 2 (Nb13): 5-13, 62-67, 93-99, and 228-266 (aa); cluster 3:226-230 and 298-337; cluster 4 (Nb29): 33-38 and 111-145.

As noted above, an "epitope" is the location on the antigen or target recognized by the antigen-binding molecule (such as the nanobodies of the invention). The term "epitope" includes both linear epitopes and conformational epitopes. FIG. 16 shows several epitopes on HSA and refers to those epitopes as "clusters."

Accordingly, in some aspects, disclosed herein is a recombinant nanobody comprising a human serum albumin (HSA) binding polypeptide and an IL-2 polypeptide, wherein the HSA binding polypeptide specifically binds to an HSA epitope selected from the group consisting of epitope 1, epitope 2, epitope 3, and epitope 4, wherein epitope 1 comprises the amino acid residues 298-307, 311, 332-341, and 371-386 of SEQ ID NO: 1, wherein epitope 2 comprises the amino acid residues 5-13, 62-67, 93-99, and 228-266 of SEQ ID NO: 1, wherein epitope 3 comprises the amino acid residues 226-230 and 298-337 of SEQ ID NO: 1, and wherein epitope 4 comprises the amino acid residues 33-38 and 111-145 of SEQ ID NO: 1. In some embodiments, the HSA binding polypeptide specifically binds to an HSA epitope comprising the amino acid residues 298-307, 311, 332-341, and 371-386 of SEQ ID NO: 1. In some embodiments, the HSA binding polypeptide specifically binds to an HSA epitope comprising 5-13, 62-67, 93-99, and 228-266 of SEQ ID NO: 1. In some embodiments, the HSA binding polypeptide specifically binds to an HSA epitope comprising the amino acid residues 33-38 and 111-145 of SEQ ID NO: 1. In some embodiments, the HSA binding polypeptide specifically binds to an HSA epitope comprising the amino acid residues 298-307, 311, 332-341, and 371-386 of SEQ ID NO: 1.

It should be understood that the specificity of an antigen-binding molecule (e.g., the HSA binding polypeptides, the nanoantibodies of the present invention) can be determined based on affinity and/or avidity. The affinity, represented by the equilibrium constant for the dissociation of an antigen with an antigen-binding molecule ($K_D$), is a measure for the binding strength between an antigenic determinant and an antigen-binding site on the antigen-binding molecule: the lesser the value of the Ko, the stronger the binding strength between an antigenic determinant and the antigen-binding molecule (alternatively, the affinity can also be expressed as the affinity constant ($K_A$), which is $1/K_D$). Methods for determining affinity are well known to those of ordinary skill in the art. Avidity is the measure of the strength of binding between an antigen-binding molecule (such as the HSA binding polypeptides and the nanobodies of the present invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as the HSA binding polypeptides and the nanobodies of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles) In some embodiments, the Ka (on rate, IMs) is about $10^5$, $10^6$, $10^7$, $10^8$, $10^9$, $10^{10}$, or $10^{11}$. In some embodiments, the Ka is about $10^7$. In some embodiments, the Kd (off rate, s) is about $10^{-5}$, $10^{-6}$, $10^{-7}$, $10^{-8}$, $10^{-9}$, $10^{-10}$, or $10^{-11}$. In some embodiments, the $K_D$ is about $10^{-7}$. In some embodiments, the antigen-binding protein disclosed herein binds to its antigen with a $K_D$ of less than about $10^{-9}$ moles/liter. Any $K_D$ value greater than 10 μM is generally considered to indicate non-specific binding. The dissociation constant may be the actual or apparent dissociation constant, as will be clear to the person of ordinary skill in the art.

In some embodiments, the HSA binding polypeptide of the nanobody specifically binds to a human HSA. In some embodiments, the HSA binding polypeptide of the nanobody specifically binds to a human HSA and a mouse serum albumin. In some embodiments, the specificity of nanobody binding can be attributed or largely attributed to a CDR3 region of the nanobody.

Therefore, in some embodiments, the HSA binding polypeptide of the nanobody comprises a complementarity determining region (CDR)3, wherein the CDR3 comprises an amino acid sequence at least 50% similarity of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO. 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100.

The "50% similarity" is calculated as follows:
Residue Group: amino acid residues are grouped according to their biophysical properties as follows:
  Group 1: A, V, I, L, F, M, W, P→V (hydrophobic residue)
  Group 2: S, G, C, N, Q, Y, T→T (polar residue)
  Group 3: K, R, H→R (positive charge residue)
  Group 4: D, E→E (negative charge residue)
  Seq_1 is a sequence selected from the group consisting of SEQ ID NOs: 10 to 100.
  Seq_2 is the incoming sequence
    1. Represent amino acid as group of residues
    2. Generate 4-mer set Set_1, Set_2 for both sequences
    3. Calculate score=(Set$_1$∩Set$_2$)/(Set_1)

Example

Seq_1=DRVLYWSCGLYSTSDDV
Seq_2=AGGGGLYKIATQYDY (incoming sequence)
Transform to residues groups:
Seq_1=ERVVTVTTTVTTTTEEV
Seq_2=VTTTTVTRVVTTTET
Generate 4-mer set:
Set_1={'ERVV', 'RVVT', 'TEEV', 'TTEE', 'TTTE', 'TTTT', 'TTTV', 'TTVT', 'TVTT', 'VTTT', 'VTVT', 'VVTV'}
Set_2={'RVVT', 'TRVV', 'TTET', 'TTTE', 'TTTT', 'TTTV', 'TIVT', 'TVTR', 'VTRV', 'VTTT', 'VVTT'}
Set_1∩Set_2={'RVVT', 'TTTE', 'TTTT', 'TTTV', 'TTVT', 'VTTT'}
Score=0.5
Therefore, Seq_2 is considered 50% similarity of Seq_1, based on the score being 0.5.

In the present disclosure, "score threshold ≥0.5: i.e." refers to all the amino acid sequences (CDR3 fingerprint sequences of nanoantibodies) that share equal or great than 50% similarity (including, for example, at least 60% similarity, at least 65% similarity, at least 70% similarity, at least 75% similarity, at least 80% similarity, least 85% similarity, at least 90% similarity, at least 95% similarity, at least 98% similarity, or at least 99% similarity) to the 91 CDR3 sequences that are set forth in SEQ ID NOs: 10 to 100.

In some embodiments, the HSA binding polypeptide of the nanobody comprises a complementarity determining region (CDR)3 comprising an amino acid sequence selected from the group consisting of SEQ ID NO: 10, SEQ ID NO: 11, SEQ ID NO: 12, SEQ ID NO: 13, SEQ ID NO. 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO. 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, and SEQ ID NO: 100.

Accordingly, in some embodiments, the HSA binding polypeptide of the nanobody comprises a CDR3 comprising an amino acid sequence selected from the group consisting of SEQ ID NO. 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO. 18, SEQ ID NO: 19, SEQ ID NO: 20, SEQ ID NO. 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO:

30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO. 81, SEQ ID NO: 82, SEQ ID NO: 83, SEQ ID NO: 84, SEQ ID NO: 85, SEQ ID NO. 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO. 97, SEQ ID NO: 98, SEQ ID NO: 99, and SEQ ID NO: 100, wherein the CDR3 specifically binds to an HSA epitope selected from the group consisting of epitope 1, epitope 2, epitope 3, and epitope 4, wherein epitope 1 comprises the amino acid residues 298-307, 311, 332-341, and 371-386 of SEQ ID NO: 1, wherein epitope 2 comprises the amino acid residues 5-13, 62-67, 93-99, and 228-266 of SEQ ID NO: 1, wherein epitope 3 comprises the amino acid residues 226-230 and 298-337 of SEQ ID NO: 1, and wherein epitope 4 comprises the amino acid residues 33-38 and 111-145 of SEQ ID NO: 1 In some embodiments, the HSA binding polypeptide of the nanobody comprises an amino acid sequence selected from the group consisting of SEQ ID NO: 2, SEQ ID NO: 3, and SEQ ID NO: 4.

With regard to the IL-2 portion of the nanobody, IL-2 is an interleukin involved in activation, proliferation, and survival of B lymphocyte, T lymphocyte, and natural killer cells through its binding to the IL-2 receptor on a cell surface. "IL-2" refers herein to a polypeptide that synthesizes and hydrolyzes cyclic adenosine 5'-diphosphate-ribose, and in humans, is encoded by the IL2 gene. In some embodiments, the IL-2 polypeptide is that identified in one or more publicly available databases as follows: HGNC: 6001, Entrez Gene: 3558, Ensembl: ENSG00000109471, OMIM: 147680, UniProtKB. P60568. In some embodiments, the IL-2 polypeptide comprises the sequence of SEQ ID NO: 5, or a polypeptide sequence having at or greater than about 80%, about 85%, about 90%, about 95%, or about 98% homology with SEQ ID NO: 5, or a polypeptide comprising a portion of SEQ ID NO: 5. The IL-2 polypeptide of SEQ ID NO. 5 may represent an immature or pre-processed form of mature IL-2, and accordingly, included herein are mature or processed portions of the HSA polypeptide in SEQ ID NO: 5.

Accordingly, in some embodiments, the IL-2 polypeptide comprises the amino acid sequence of SEQ ID NO: 5 or a functional fragment thereof. It should be understood herein that a "functional fragment" of IL-2 refers to a fragment of IL-2 that possesses a bioactive property, including, for example, binding to an IL-2 receptor, and/or activating NK cells, B and/or T lymphocytes. In some embodiments, the HSA binding polypeptide linked to the IL-2 polypeptide via a linker. In some embodiments, the linker comprises the amino acid sequence of SEQ ID NO: 6.

In some embodiments, the IL-2 polypeptide is a recombinant human IL-2 polypeptide, including, but not limited to, an aldesleukin. The aldesleukin can have a serine substituted for a cysteine at amino acid position 125. In some embodiments, the aldesleukin comprises an amino acid sequence of SEQ ID NO: 103. In some embodiments, the aldesleukin is PROLEUKIN (Novartis).

Accordingly, in some embodiments, disclosed herein is a recombinant nanobody comprising an HSA binding polypeptide and an IL-2 polypeptide, wherein the HSA binding polypeptide comprises an amino acid sequence selected from the group consisting of SEQ ID NO: 2, SEQ ID NO: 3, and SEQ ID NO: 4, wherein the IL-2 polypeptide comprises the amino acid sequence of SEQ ID NO: 5 or a functional fragment thereof, wherein the HSA binding polypeptide is linked to the IL-2 polypeptide via a linker, and wherein the linker comprises the amino acid sequence of SEQ ID NO: 6.

In some embodiments the nanobody has increased thermostability and/or increased resistance to serum protease activities as compared to a natural IL-2 or other IL-2 such as ALBULEUKIN (Human Genome Sciences). In some embodiments, the nanobody reaches an in vivo maximum effective molar concentration more quickly than a natural IL-2 or other IL-2 such as ALBULEUKIN (Human Genome Sciences).

In some embodiments, the recombinant nanobody of any preceding aspect is less than about 50 kDa, which can be, for example, less than about 45 kDa, less than about 40 kDa, less than about 35 kDa, or less than about 30 kDa. In some embodiments, the recombinant nanobody of any preceding aspect comprises an amino acid sequence selected from the group consisting of SEQ ID NO. 7, SEQ ID NO. 8, and SEQ ID NO: 9.

In some embodiments, the recombinant nanobody has about the same affinity or an increased affinity between the IL-2 polypeptide portion of the nanobody and an IL-2 receptor as compared to a natural IL-2 or other IL-2 such as ALBULEUKIN (Human Genome Sciences). The IL-2 receptor is a heterotrimeric receptor having three subunits often referred as alpha subunit (or IL-2Rα or CD25), beta subunit (or IL-2Rβ or CD122), and gamma subunit (or IL-2γ, common gamma chain, or CD132). The beta and gamma subunits form a complex with intermediate affinity binding to IL-2 (Kd approximately $10^{-9}$ M); while the alpha, beta, and gamma subunits form a high affinity IL-2 receptor binding to IL-2 (Kd approximately $10^{-11}$ M). In some embodiments, the recombinant nanobody has about the same affinity or an increased affinity between the IL-2 polypeptide portion of the nanobody and an IL-2 receptor that comprises, for example, an alpha subunit, a beta and a gamma subunit, or alpha, beta, and gamma subunit. In some embodiments, the recombinant nanobody has about the same affinity or an increased affinity between the IL-2 polypeptide portion of the nanobody and an IL-2 receptor, where in the IL-2 receptor comprises an alpha, a beta, and a gamma subunit.

It is understood herein that affinity at acidic pH correlates well with elimination rate (spearman ρ=0.78), followed by affinity at neutral pH (in particular, the off rates). Therefore, both slow binding off-rates and acidic pH-dependent interaction are important to extend the stability of the nanobody-HSA-FcRn ternary complex in the endosome. In some embodiments, the HSA binding polypeptide of the recombinant nanobody specifically binds to HSA in a structurally stable form at pH ranging from about 3.5 to about 7.5.

A natural IL-2 has a half-life around less than 30 to 60 minutes in humans Targeting the endogenous human serum albumin by using the recombinant nanobodies can extend the half-life of IL-2. Accordingly, in some embodiments, the recombinant IL-2 nanobody as described herein has a half-life at least 50 times (for example, at least 100 times, at least 200 times, least 300 times, least 400 times, at least 500 times, at least 600 times, at least 700 times, at least 800 times, at least 900 times, or at least 1000 times) higher than a natural or non-nanobody recombinant IL-2 polypeptide or a control nanobody. In some embodiments, the recombinant IL-2 nanobody described herein has a half-life at least 50 times (for example, at least 100 times, at least 200 times, least 300 times, least 400 times, at least 500 times, at least 600 times, at least 700 times, at least 800 times, at least 900 times, or at least 1000 times) higher than a recombinant human IL-2 such as an aldesleukin. In some embodiments, the recombinant IL-2 nanobody described herein has a half-life at least 2 times, 5 times, 10 times, 20 times, 30 times, 40 times, 50 times, 60 times, 70 times, 80 times, 90 times or 100 times higher than a recombinant human IL-2 such as ALBULEUKIN (Human Genome Sciences) (HSA/IL-2 fusion protein).

In some aspects, disclosed herein is a nanobody comprising a human serum albumin (HSA) binding polypeptide, wherein the HSA binding polypeptide comprises a complementarity determining region (CDR)3, wherein the CDR3 comprises an amino acid sequence at least 50% similarity (including, for example, at least 60% similarity, at least 65% similarity, at least 70% similarity, at least 75% similarity, at least 80% similarity, least 85% similarity, at least 90% similarity, at least 95% similarity, at least 98% similarity, or at least 99% similarity) of SEQ ID NO: 10, SEQ ID NO: 11, SEQ ID NO: 12, SEQ ID NO: 13, SEQ ID NO: 14, SEQ ID NO: 15, SEQ ID NO. 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO. 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO. 76, SEQ ID NO: 77, SEQ ID NO: 78, SEQ ID NO: 79, SEQ ID NO: 80, SEQ ID NO. 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO. 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100. Similarity is calculated as described above.

In some aspects, disclosed herein is a polypeptide comprising a human serum albumin (HSA) binding polypeptide, wherein the HSA binding polypeptide comprises a complementarity determining region (CDR)3, wherein the CDR3 comprises an amino acid sequence selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO. 28, SEQ ID NO: 29, SEQ ID NO: 30, SEQ ID NO: 31, SEQ ID NO: 32, SEQ ID NO:

33, SEQ ID NO: 34, SEQ ID NO: 35, SEQ ID NO: 36, SEQ ID NO: 37, SEQ ID NO: 38, SEQ ID NO. 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: SS, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO. 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, and SEQ ID NO: 100.

In some embodiments, the recombinant nanobody or polypeptide of any preceding aspect is formulated in a pharmaceutically acceptable carrier.

Methods of Treatment

Provided herein are methods of treating a cancer in a subject in need thereof, comprising administering a therapeutically effective amount of a recombinant nanobody described herein. The current disclosure demonstrates the surprising finding that administering a therapeutically effective amount of a recombinant nanobody comprising a human serum albumin (HSA) binding polypeptide and an IL-2 polypeptide results in a treatment of cancer.

Accordingly, included herein are methods of treating cancer in a subject in need thereof, comprising administering a therapeutically effective amount of a recombinant nanobody, wherein the nanobody comprises a human serum albumin (HSA) binding polypeptide and an IL-2 polypeptide, wherein the HSA binding polypeptide specifically binds to an HSA epitope, wherein the HSA epitope is selected from the group consisting of epitope 1, epitope 2, epitope 3, and epitope 4, wherein epitope 1 comprises the amino acid residues 298-307, 311, 332-341, and 371-386 of SEQ ID NO: 1, wherein epitope 2 comprises the amino acid residues 5-13, 62-67, 93-99, and 228-266 of SEQ ID NO: 1, wherein epitope 3 comprises the amino acid residues 226-230 and 298-337 of SEQ ID NO: 1, and wherein epitope 4 comprises the amino acid residues 33-38 and 111-145 of SEQ ID NO: 1.

In some embodiments of the method, the HSA binding polypeptide portion of the nanobody specifically binds to an HSA epitope comprising the amino acid residues 298-307, 311, 332-341, and 371-386 of SEQ ID NO: 1. In some embodiments, the HSA binding polypeptide specifically binds to an HSA epitope comprising 5-13, 62-67, 93-99, and 228-266 of SEQ ID NO: 1. In some embodiments, the HSA binding polypeptide specifically binds to an HSA epitope comprising the amino acid residues 33-38 and 111-145 of SEQ ID NO: 1. In some embodiments, the HSA binding polypeptide specifically binds to an HSA epitope comprising the amino acid residues 298-307, 311, 332-341, and 371-386 of SEQ ID NO: 1.

Examples of cancers that can be treated using the methods described herein include, but are not limited to, melanoma, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In some embodiments, the cancer is melanoma. In some embodiments, the cancer is renal carcinoma.

In some embodiments, the administration of the recombinant nanobody described herein decreases metastasis, slows down and/or stops tumor growth, reduces tumor size, promotes activation, proliferation, and cytotoxic function of T cells and NK cells, increases levels of anti-tumor antibodies, prolongs the survival of the subject, and/or increases the survival rate. It should be understood and herein contemplated that the terms "increase", "promote", "prolong" and "decrease", "reduce" used herein refer to an increase or decrease as compared to compared with prior to the treatment of the subject or as compared with incidence of such symptom in a general or study population.

In some embodiments of the method, the HSA binding polypeptide of any preceding aspect comprises a complementarity determining region (CDR)3, wherein the CDR3 comprises an amino acid sequence at least 50% similarity (including, for example, at least 60% similarity, at least 65% similarity, at least 70% similarity, at least 75% similarity, at least 80% similarity, least 85% similarity, at least 90% similarity, at least 95% similarity, at least 98% similarity, or at least 99% similarity) of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO. 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, or SEQ ID NO: 100.

The "50% similarity" is calculated as follows:

Residue Group: amino acid residues are grouped according to their biophysical properties as follows:

Group 1: A, V, I, L, F, M, W, P→V (hydrophobic residue)

Group 2: S, G, C, N, Q, Y, T→T (polar residue)

Group 3: K, R, H→R (positive charge residue)

Group 4: D, E→E (negative charge residue)

Seq_1 is a sequence selected from the group consisting of SEQ ID NOs: 10 to 100.

Seq_2 is the incoming sequence

1. Represent amino acid as group of residues

2. Generate 4-mer set Set_1, Set_2 for both sequences

3. Calculate score=(Set$_1 \cap$Set$_2$)/(Set_1)

Example

Seq_1=DRVLYWSCGLYSTSDDV
Seq_2=AGGGGLYKIATQYDY (incoming sequence)
Transform to residues groups:
Seq_1=ERVVTVTTTVTTTTEEV
Seq_2=VTTTTVTRVVTTTET
Generate 4-mer set:
Set_1={'ERVV', 'RVVT', 'TEEV', 'TTEE', 'TTTE', 'TTTT', 'TTTV', 'TTVT', 'TVTT', 'VTTT', 'VTVT', 'VVTV'}
Set_2={'RVVT', 'TRVV', 'TTET', 'TTTE', 'TTTT', 'TTTV', 'TIVT', 'TVTR', 'VTRV', 'VTTT', 'VVTT'}
Set_1∩Set_2={'RVVT', 'TTTE', 'TTTT', 'TTTV', 'TTVT', 'VTTT'}
Score=0.5
Therefore, Seq_2 is considered 50% similarity of Seq_1, based on the score being 0.5.

In the present disclosure, score threshold ≥0.5: i.e., refers to all the amino acid sequences (CDR3 fingerprint sequences of nanoantibodies) that share equal or great than 50% similarity (including, for example, at least 60% similarity, at least 65% similarity, at least 70% similarity, at least 75% similarity, at least 80% similarity, least 85% similarity, at least 90% similarity, at least 95% similarity, at least 98% similarity, or at least 99% similarity) of the 91 CDR3 master sequences that are set forth in SEQ ID NOs: 10 to 100.

In some embodiments of the method, the HSA binding polypeptide of any preceding aspect comprises a complementarity determining region (CDR)3 comprising an amino acid sequence selected from the group consisting of SEQ ID NO: 10 to 100 In some embodiments, the method of treating cancer comprises administering a therapeutically effective amount of a recombinant nanobody comprising a human serum albumin (HSA) binding polypeptide and an IL-2 polypeptide, wherein the HSA binding polypeptide comprises an amino acid sequence selected from the group consisting of SEQ ID NO: 2, SEQ ID NO: 3, and SEQ ID NO: 4. In some embodiments, the IL-2 polypeptide portion of the nanobody comprises the amino acid sequence of SEQ ID NO: 5 or a functional fragment thereof. In some embodiments, the HSA binding polypeptide is linked to the IL-2 polypeptide via a linker. In some embodiments, the linker comprises the amino acid sequence of SEQ ID NO: 6.

In some embodiments of the method, the recombinant nanobody is less than about 50 kDa, which can be, for example, less than about 45 kDa, less than about 40 kDa, less than about 35 kDa, or less than about 30 kDa. In one example, the recombinant polypeptide comprises an amino acid sequence selected from the group consisting of SEQ ID NOs: 7, SEQ ID NO: 8, and SEQ ID NO: 9.

In some embodiments of the present invention, the recombinant nanobody has a half-life in the subject about 10 times, about 20 times, about 30 times, about 40 times, 50 times, about 100 times, about 200 times, about 300 times, about 400 times, about 500 times, about 600 times, about 700 times, about 800 times, about 900 times, or about 1000 times higher than a natural IL-2 polypeptide, an aldesleukin (e.g., PROLEUKIN, Novartis) or an ALBULEUKIN (Human Genome Sciences).

Accordingly, in some embodiments, the dosing frequency of the recombinant nanobody is about 2-fold less, about 3-fold less, about 4-fold less, about 5-fold less, about 6-fold less, about 7-fold less, about 8-fold less, about 9-fold less, about 10-fold less, about 15-fold less, about 20-fold less, about 30-fold less, about 40-fold less, about 50-fold less, about 80-fold or less, about 100-fold or less, about 150-fold or less, about 200-fold or less, about 300-fold or less, about 500-fold or less, about 800-fold or less, or about 1000-fold less than the dosing frequency of administering a natural IL-2 polypeptide, an aldesleukin or ALBULEUKIN (Human Genome Sciences).

Dosing frequency for the recombinant nanobody of any preceding aspect, includes, but is not limited to, at least once every month, once every three weeks, once every two weeks, once a week, twice a week, three times a week, four times a week, five times a week, six times a week, daily, or twice a day, three times a day, four times a day, five times a day, six times a day, seven times a day, eight times a day, or nine times a day. In some embodiments, the interval between each administration is less than about 2 months, less than about a month, less than about 3 weeks, less than about 2 weeks, or less than less than about a week, such as less than about any of 6, 5, 4, 3, 2, or 1 day(s). In some embodiments, the dosing frequency for the recombinant nanobody includes, but is not limited to, at least once a day, twice a day, or three times a day. In some embodiments, the interval between each administration is less than about 48 hours, about 36 hours, about 24 hours, about 22 hours, about 20 hours, about 18 hours, about 16 hours, about 14 hours, about 12 hours, about 10 hours, about 9 hours, about 8 hours, or about 7 hours. In some embodiments, the interval between each administration is less than about 24 hours, about 22 hours, about 20 hours, about 18 hours, about 16 hours, about 14 hours, about 12 hours, about 10 hours, about 9 hours, about 8 hours, about 7 hours, or about 6 hours. In some embodiments, the interval between each administration is constant. For example, the administration can be carried out daily, every two days, every three days, every four days, every five days, or weekly. Administration can also be continuous and adjusted to maintaining a level of the recombinant nanobody within any desired and specified range.

The present disclosure shows that the recombinant nanobody described herein can prolong the half-life of IL-2. In some embodiments, the recombinant nanobody can increase duration of the therapeutic effect of IL-2 and/or decrease the amount of IL-2 that must be administered as compared to a natural IL-2 polypeptide or ALBULEUKIN (Human Genome Sciences). Accordingly, the therapeutically effective dosage amount of IL-2 as a portion of the recombinant nanobody can be in an amount which is less than the amount recommended for one dosage of IL-2 (e.g, a natural IL-2 polypeptide or ALBULEUKIN (Human Genome Sciences)). For example, if the traditionally recommended dosage of IL-2 is X amount then the nanoparticle or the recombinant polypeptide composition can comprise an IL-2 in an amount of about 0.9×, about 0.8×, about 0.7×, about 0.6×, about 0.5×, about 0.4×, about 0.3×, about 0.2×, or about 0.1×. In some embodiments, these lower therapeutically effective dosage amounts of IL-2 can reduce side effects of IL-2, if any, and/or reduce likelihood of the subject's resistance to IL-2 after administration for a period of time.

The disclosed methods can be performed any time prior to the onset of cancer. In some aspects, the disclosed methods can be employed 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 years; 12, 11, 10, 9, 8, 7, 6, 5, 4, 3, 2, or 1 months; 30, 29, 28, 27, 26, 25, 24, 23, 22, 21, 20, 19, 18, 17, 16, 15, 14, 13, 12, 11, 10, 9, 8, 7, 6, 5, 4, or 3 days; 60, 48, 36, 30, 24, 18, 15, 12, 10, 9, 8, 7, 6, 5, 4, 3, or 2 hours prior to the onset of cancer; or 1, 2, 3, 4, 5, 6, 7, 8, 9, 10, 15, 20, 25, 30, 35, 40, 45, 50, 55, 60, 75, 90, 105, 120 minutes; 3, 4, 5, 6, 7, 8, 9, 10, 11, 12, 15, 18, 24, 30, 36, 48, 60 hours; 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days; 4, 5, 6, 7, 8, 9, 10, 11, 12 or more months; 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1 years after the onset of cancer. The disclosed method can be performed at any stage of cancer, including, stage 0, stage I, stage II, stage III, and stage IV of cancer.

The recombinant nanobody described herein may be in any appropriate dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intravenous, intrathecal, intravitreal, intracerebral, gingival, subgingival, intracerebroventricular, and intradermal. Such formulations may be prepared by any method known in the art.

The compounds and compositions disclosed shown herein are effective in treating, inhibiting, reducing, decreasing, ameliorating and/or preventing cancers, and/or metastasis in a subject comprising administering to the subject a therapeutically effective amount of the compound of any preceding aspect or the pharmaceutical composition of any preceding aspect. In some examples, the cancer is selected from the group consisting of lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, breast cancer, epithelial cancer, renal cancer, genitourinary cancer, esophageal carcinoma, head and neck carcinoma, large bowel cancer, hematopoietic cancers, testicular cancer, colon cancer, rectal cancer, prostate cancer, and pancreatic cancer.

In some embodiments, the recombinant nanobody of any preceding aspect is formulated in a pharmaceutically acceptable carrier.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1: Systematic Characterization of HSA-Nbs

Figure 1B:
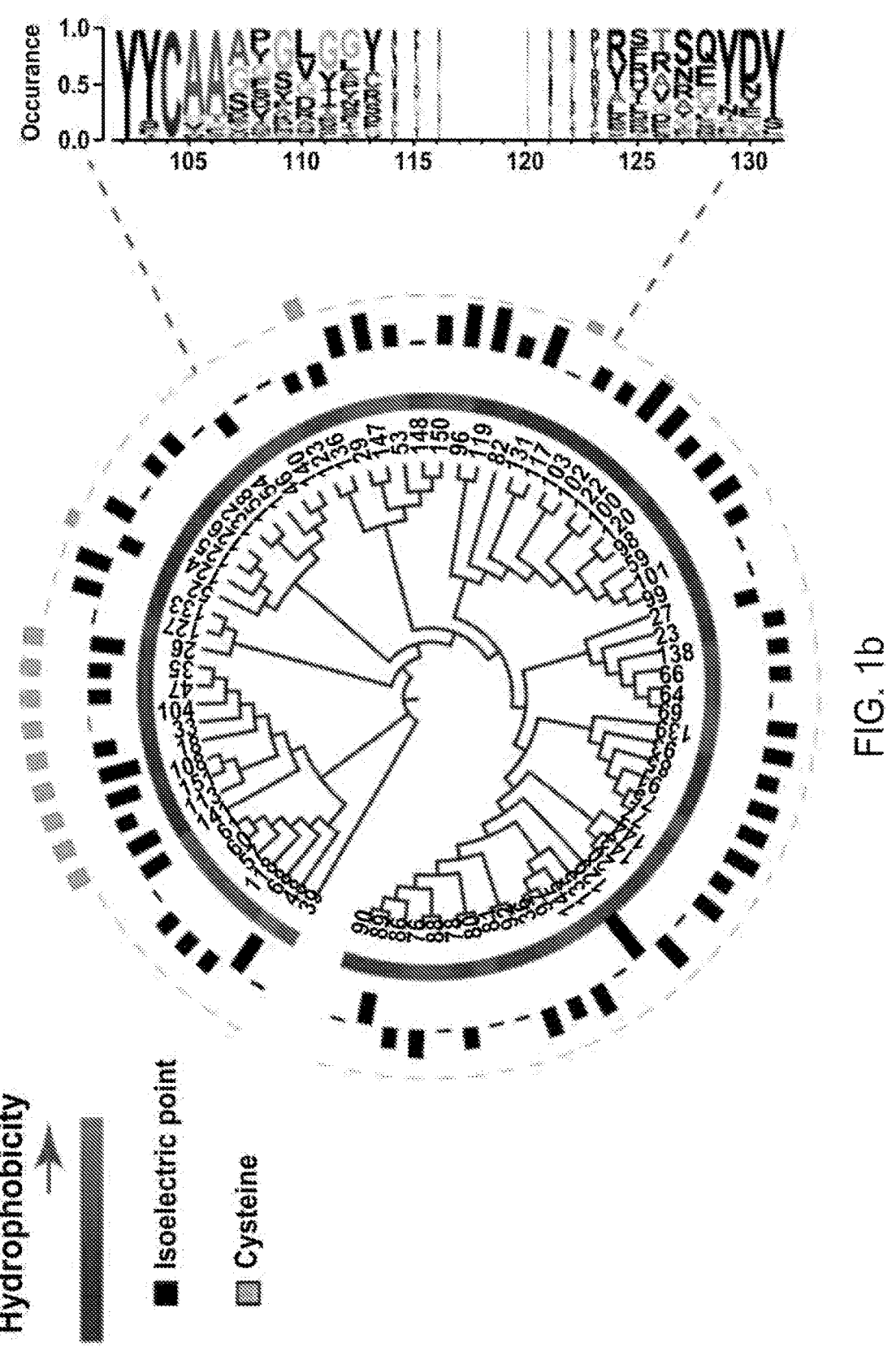
FIG. 1b shows circos and logo plots showing the diversity of CDR3.

Eighty nine recombinant, soluble nanobodies (Nbs) with unique CDR3 sequences were expressed and purified from E. coli using His-cobalt resin. Schematics of the Nbs and their amino acid compositions on the CDR loops are presented in FIG. 1a. These Nbs have highly diversified CDR3 sequences and vary considerably in physicochemical properties (FIG. 1b) including isoelectric points, hydrophobicity, and CDR3 cysteine that forms intramolecular disulfide, which is important for thermostability. CDR3 amino acids were aligned and the occurrence at each position was calculated to generate the sequence web logo (FIG. 1b). Enzyme-linked immunosorbent assay (ELISA) was performed to assess the relative affinity of Nbs for binding to albumin of different species including human, monkey and mouse. While all 89 Nbs bind HSA, over three orders of magnitude O.D. affinity was observed. Interestingly, less than 50% of HSA-Nbs bind highly conserved cynomolgus monkey albumin and only approximately 9% (8 Nbs) can appreciably cross-react with mouse albumin. Whereas HSA-specific Nbs demonstrated outstanding specificity, these cross-species binders are also useful for experiments in the respective animal models.

Figures 1C, 1D, 1E, 1F, 1G, 1H:
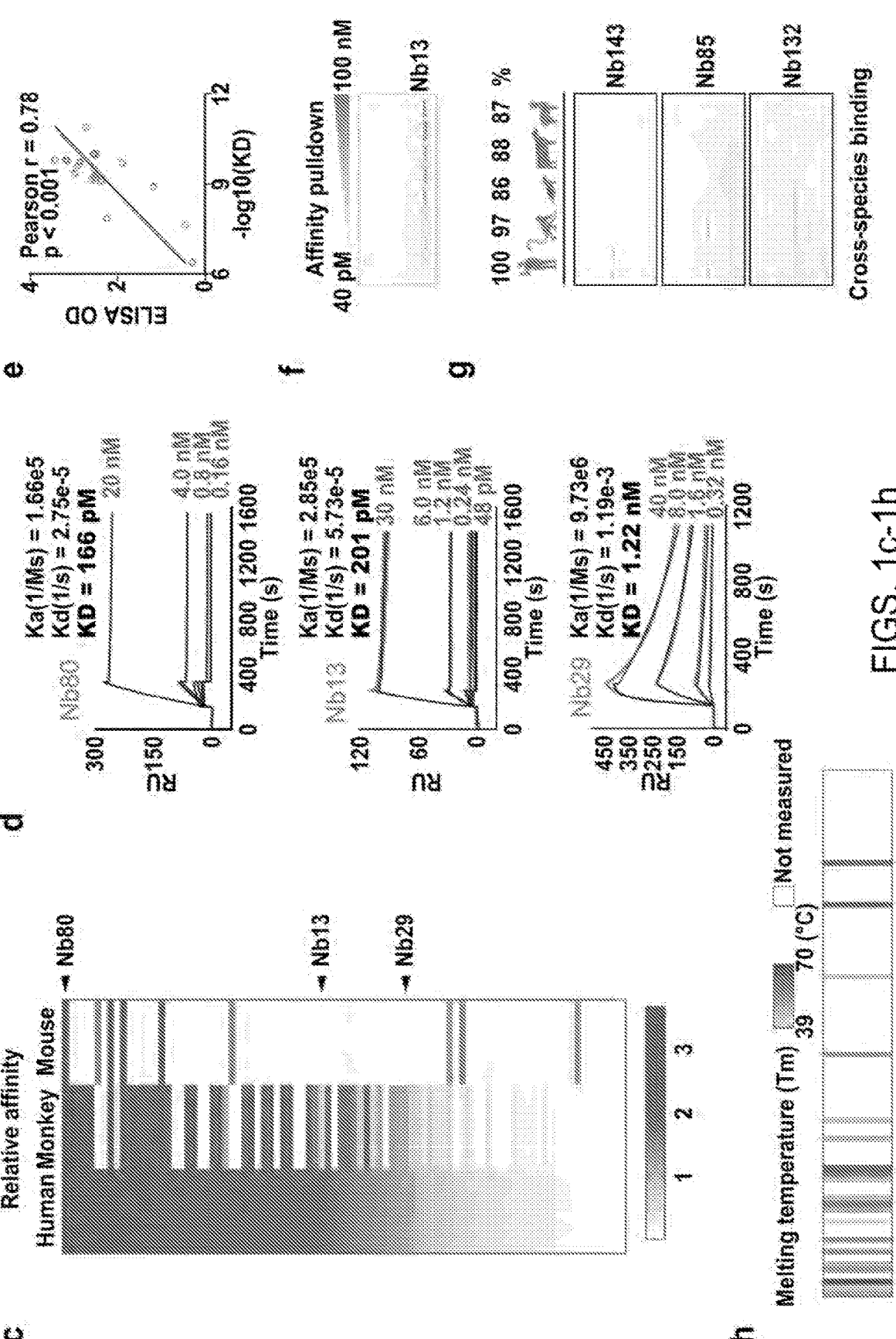
FIG. 1e shows ELISA heat map of albumin cross-species binding of 89 different Nbs.
FIG. 1d shows KD (including Ka and Kd) of 3 representative Nbs by surface plasmon resonance.
FIG. 1f shows beads binding assay of HSA-Nb13 complex at various Nb concentrations.
FIG. 1g shows validation of Nb cross reactivity by pulldown assay. Three representative Nbs (Nb3, Nb6 and Nb13) were immunoprecipitated by affinity resins that are coupled with albumin of different species including human, monkey, mouse, bovine and llama.
FIG. 1h shows heatmap of Nb thermostability by differential scanning fluorimetry.
Figures 8A, 8B, 8C, 8D, 8E, 8F, 8G, 8H, 8I, 8J, 8K, 8L:
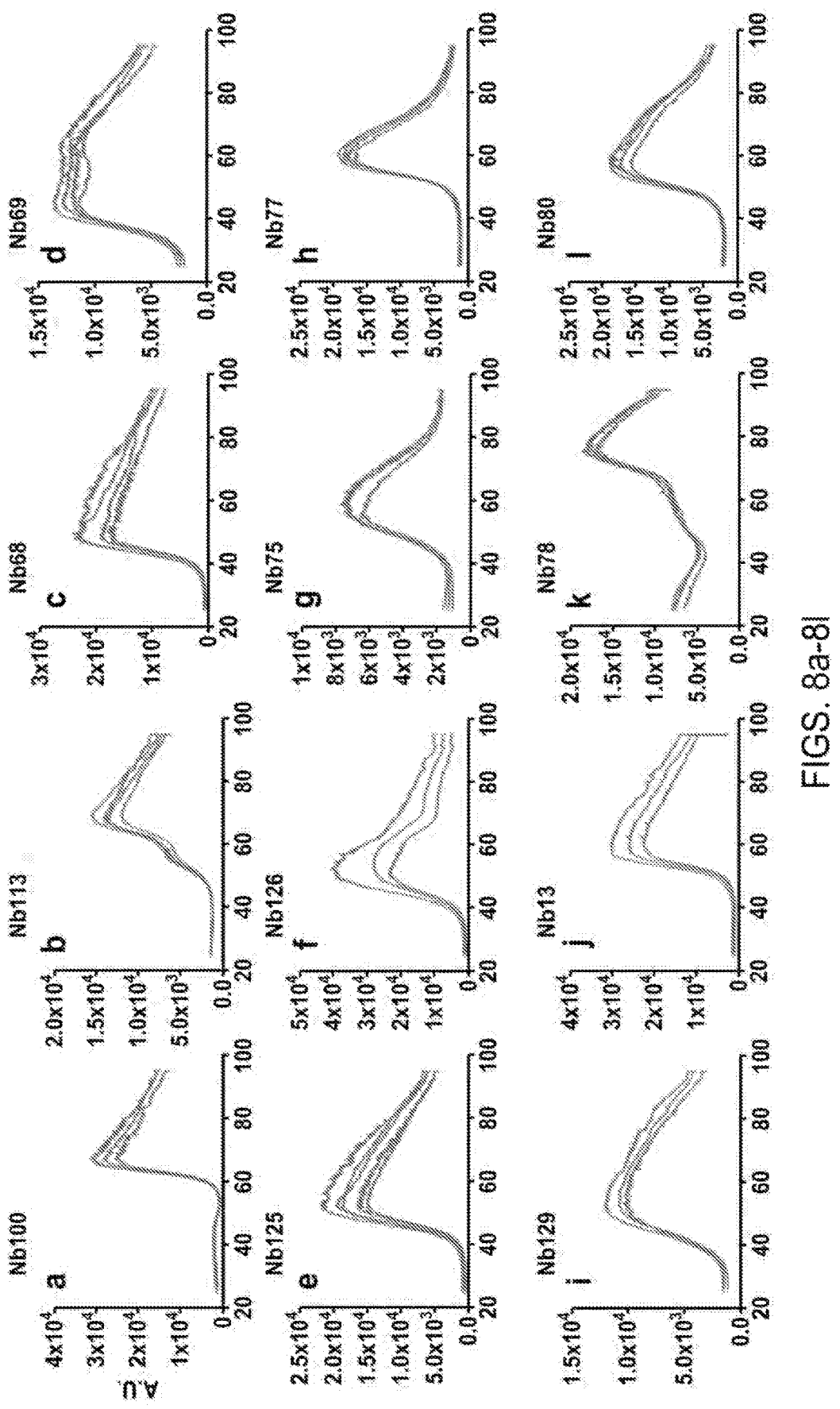
FIG. 8a, Nb100: Tm=63.37° C.
FIG. 8b, Nb113: Tm=64.12° C.
FIG. 8c, Nb68: Tm=44° C.
FIG. 8d Nb69: Tm=38.02° C.
FIG. 8e, Nb125: Tm=47.07° C.
FIG. 8f, Nb126: Tm=45.89° C.
FIG. 8g, Nb75: Tm=49.34° C.
FIG. 8h, Nb77: Tm=54.29° C.
FIG. 8i, Nb129: Tm=44.12° C.
FIG. 8j, Nb13: Tm=53.42° C.
FIG. 8k, Nb78: Tm=70.52° C.
FIG. 8l, Nb80: Tm=50.82° C.
Figures 8M, 8N, 8O, 8P, 8Q, 8R, 8S, 8T:
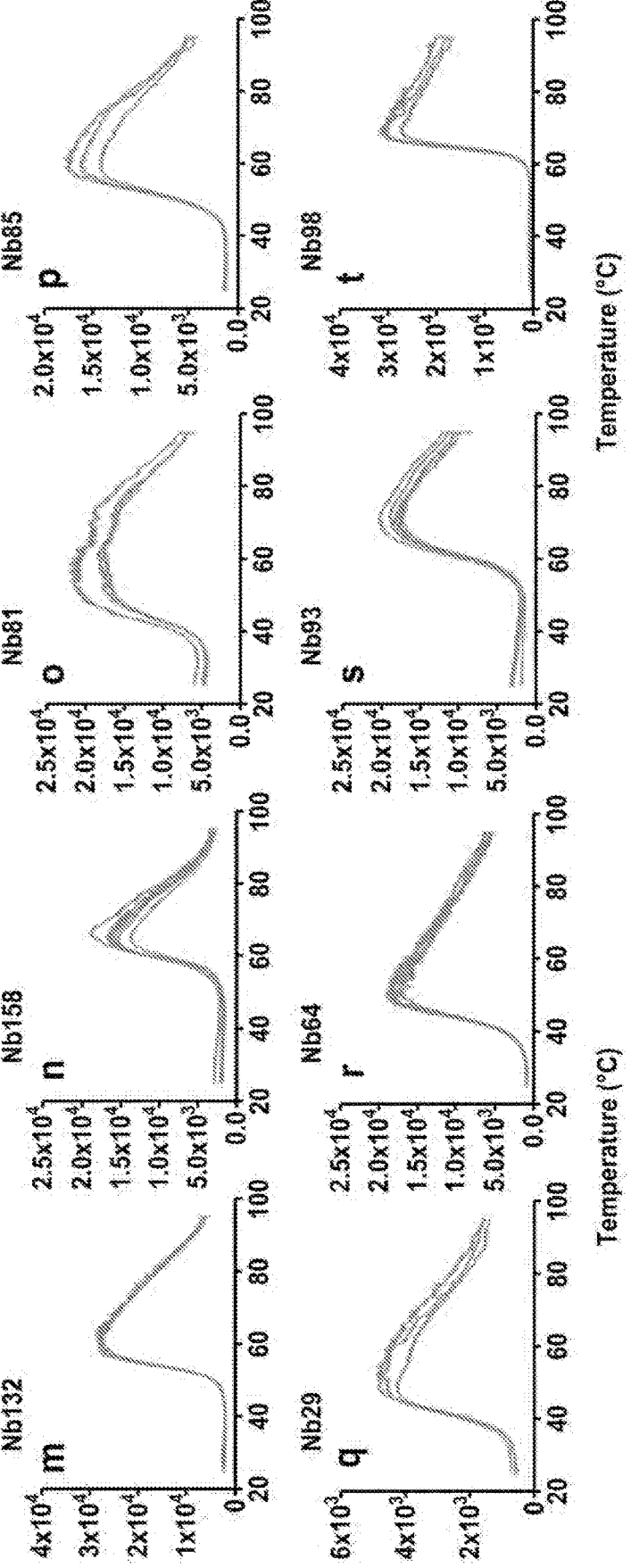
FIG. 8m, Nb132: Tm=54° C., FIG. 8n, Nb158: Tm=59.97° C.
FIG. 8o, Nb81: Tm=42.68° C.
FIG. 8p, Nb85: Tm=53.17° C.
FIG. 8q. Nb29: Tm=42.16° C.
FIG. 8r, Nb64: Tm=45.17° C.
FIG. 8s, Nb93: Tm=61.18° C.
FIG. 8t, Nb98: Tm=64.91° C.

Twenty HSA-Nbs spanning different ELISA ranges were randomly selected to carefully determine their $K_D$ affinity (both $K_{on}$ and $K_{off}$) by surface plasmon resonance (SPR). 75% (15/20) of the selected Nbs are affinity-matured, obtaining sub-nM affinity for HSA binding but with unique, often diverse association and dissociation kinetics (FIG. 1d). For example, Nb 126 has a $K_{off}$ of $1.7\times10^3$ (1/s), two orders of magnitude faster than Nb 26; however, both obtain similar $K_D$ (251 pM and 206 pM, respectively) owing to different association rates. Other Nbs such as Nb 77 (13 pM), Nb 13 (201 pM) and Nb 80 (166 pM) demonstrated both quick-on and slow-off rates. Beads binding assay was carried out to confirm the SPR measurement (FIG. 1f). In addition, a good correlation (R2=0.78, p<0.001) between calculated ELISA affinity and the SPR $K_D$ was found (FIG. 1e). Cross-species binding of albumins was confirmed by beads binding assay (FIG. 1g). The thermostability of 20 HSA-Nbs was evaluated using differential scanning calorimetry (DSC). A wide range of melting temperature from 30 to 70° C. was observed (FIG. 1h, FIG. 8). In conclusion, this rich repertoire is composed of exceptionally high-quality and diversified Nbs.

Figure 2A:
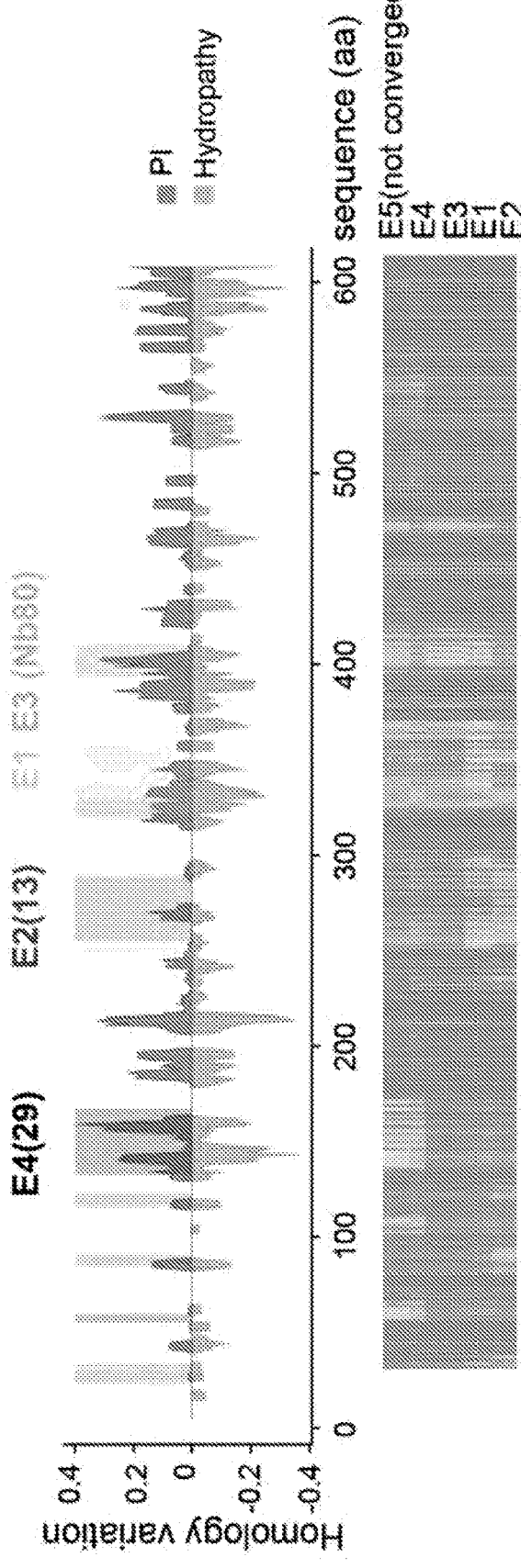
FIG. 2a shows major HSA epitopes identified by structural docking.
Figures 2B, 2C, 2D:
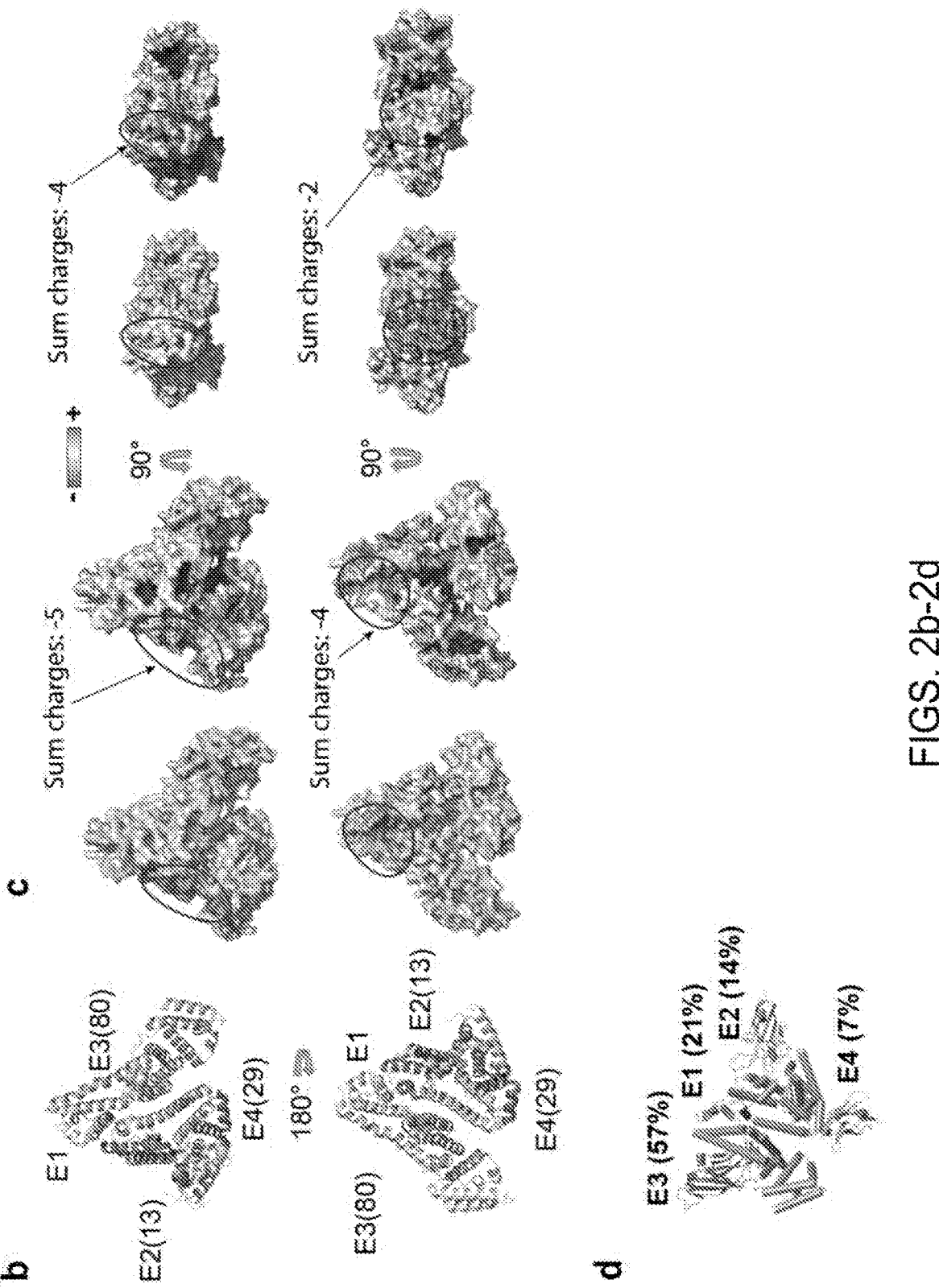
FIG. 2b shows a cartoon representation of HSA and the four major epitopes.
FIG. 2c shows co-localization of electrostatic surfaces of HSA and the epitopes.
FIG. 2d shows the relative abundance of epitopes based on cross-link models of HSA-Nb complexes.
Figure 9:
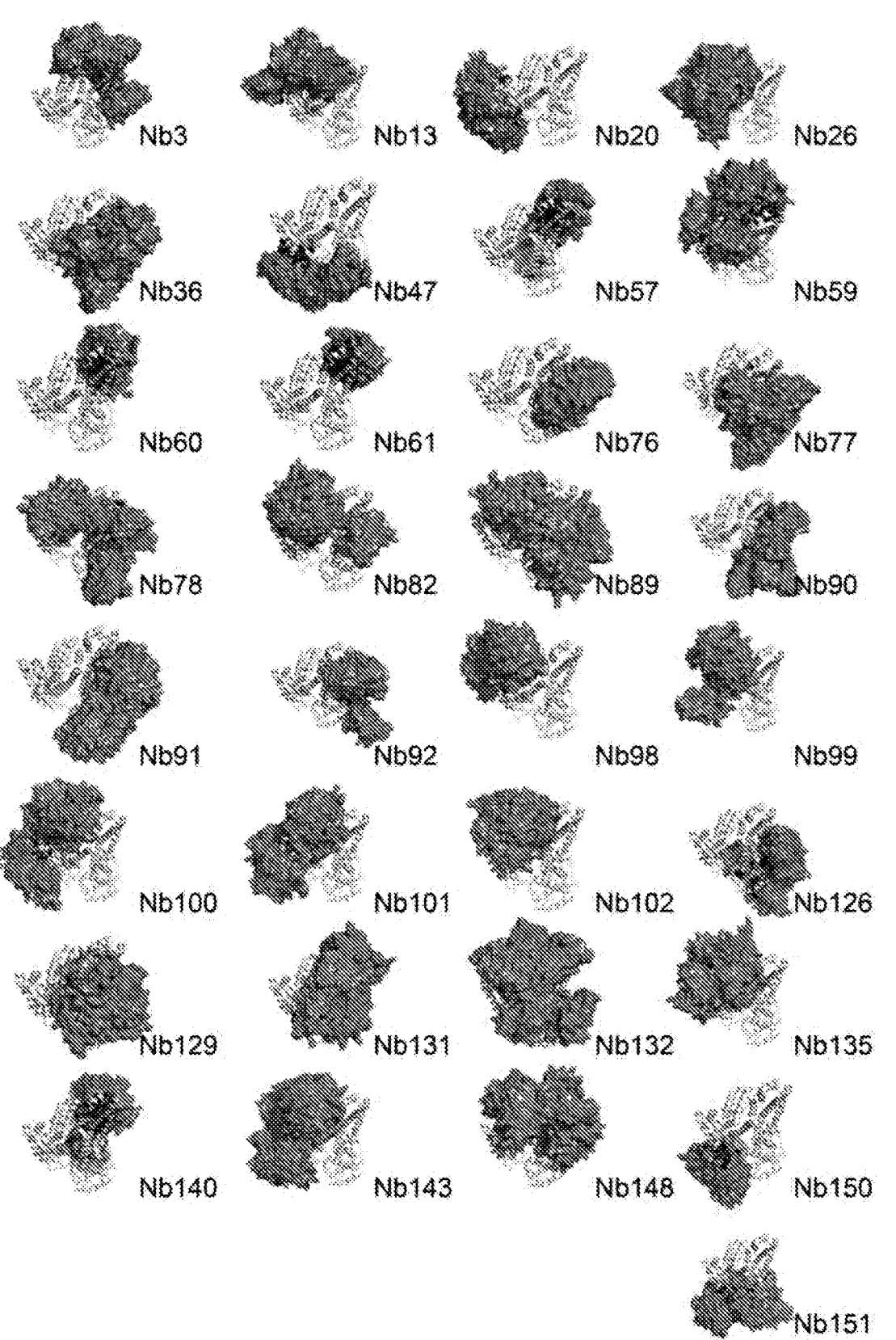
FIG. 9 shows the cross-link models of the representative HSA-Nb complexes.
Figures 10A, 10B, 10C, 10D:
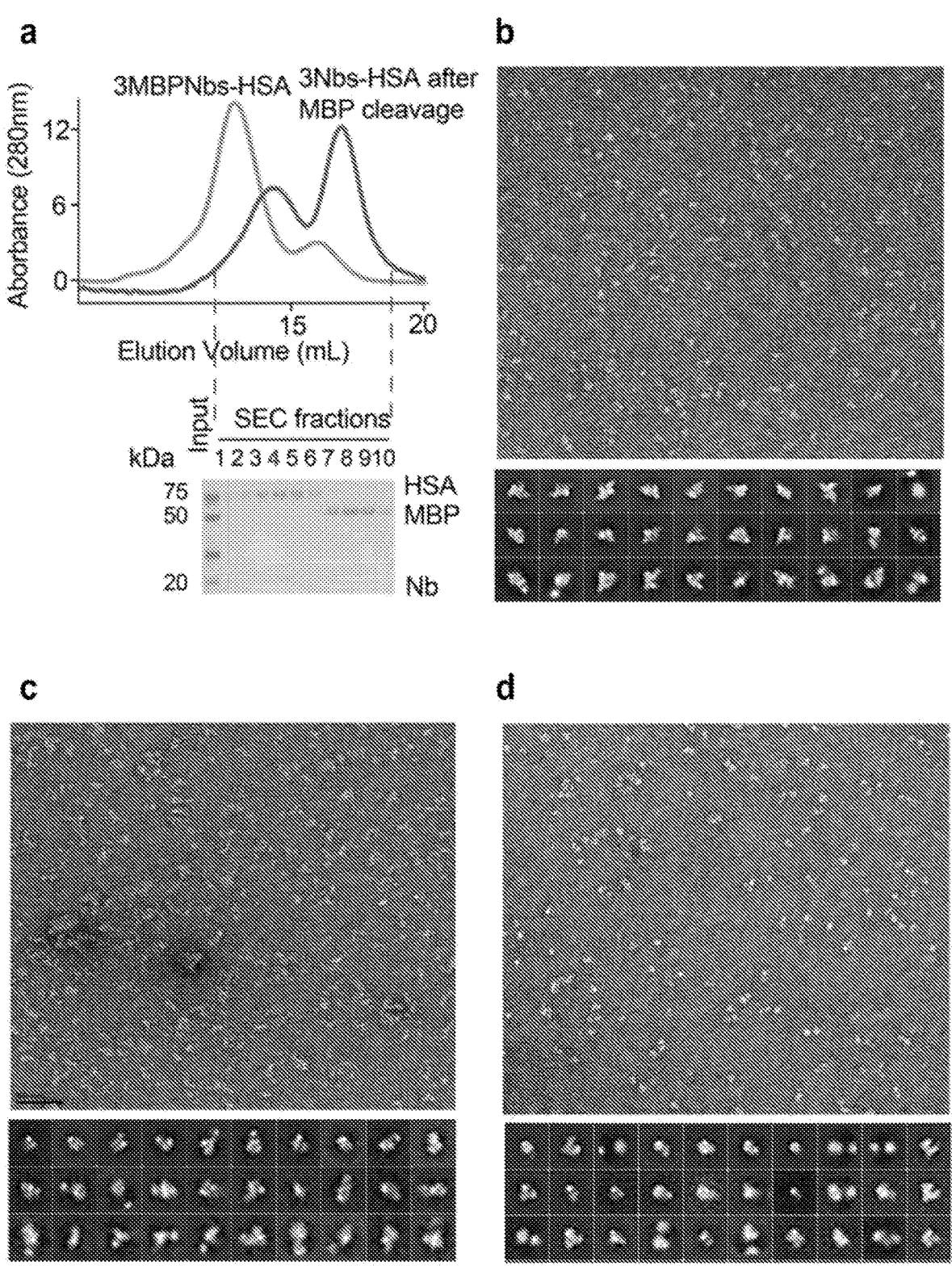
FIG. 10a shows the size-exclusion chromatography and SDS-PAGE analysis of the reconstituted tetrameric HSA-Nb complex.
FIGS. 10b-10d show the EM images of the HSA-Nb complex w/o a MBP (maltose binding protein) tag and HSA.

Example 2. The Landscape of HSA Immunogenicity Revealed by Cross-Linking and Modeling A fundamental characteristic of humoral immunity is its ability to produce a large cohort of antibodies to recognize any exogenous structures that are exposed, although the structural basis that supports such universality remains to be fully understood. Here, to better appreciate the landscape and nature of immunogenicity, a rapid docking approach was employed to identify the epitope(s) (FIG. 2a) which were subsequently verified by chemical cross-linking and mass spectrometry (MS) (CXMS, FIG. 2b, FIG. 9). Several features were learned. 1) Despite highly divergent CDR3 sequences and other physicochemical properties of HSA-Nbs, only four dominant epitopes were identified (FIGS. 2a-2d and FIG. 16, indicating the presence of immunodominance. 2) Epitopes are highly selective by the mammalian immune system to avoid shared sequences between human and camelid. 3) Surface electrostatic charges and epitope shapes are important.

Figures 3A, 3B, 3C, 3D:
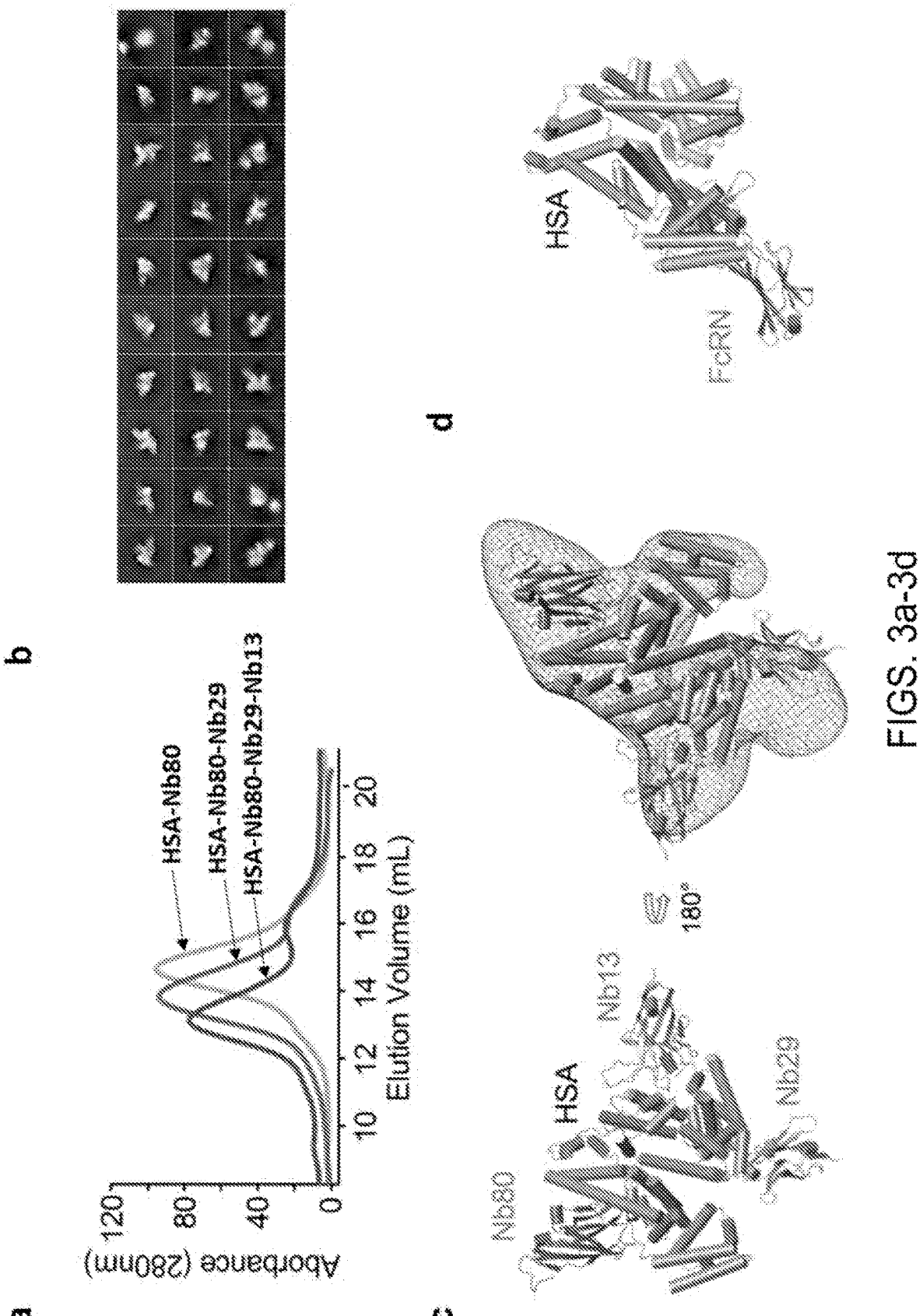
FIG. 3a shows size-exclusion chromatography (SEC) analysis of the reconstituted tetrameric complex that is composed by Nb13, Nb29, Nb80 and HSA.
FIG. 3b shows negative stain images of the complex.
FIG. 3c shows hybrid structural model (best score) of the complex overlapped by negative stain EM.
FIG. 3d shows X-ray structure of HSA-FcRn complex.
Figure 3E:
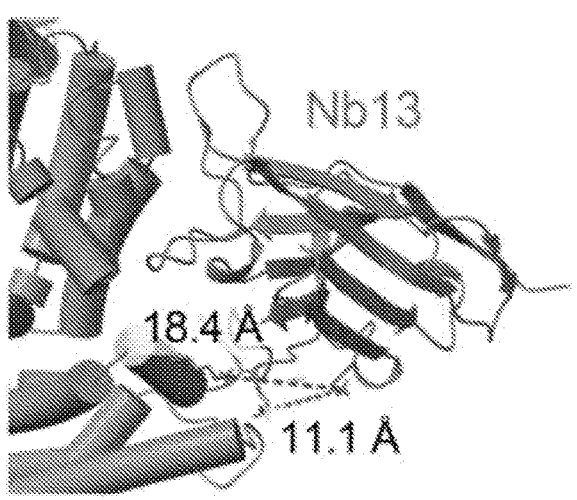
FIGS. 3e to 3g show close-up views of interfaces and cross-link restraints on the models.
Figure 3F:
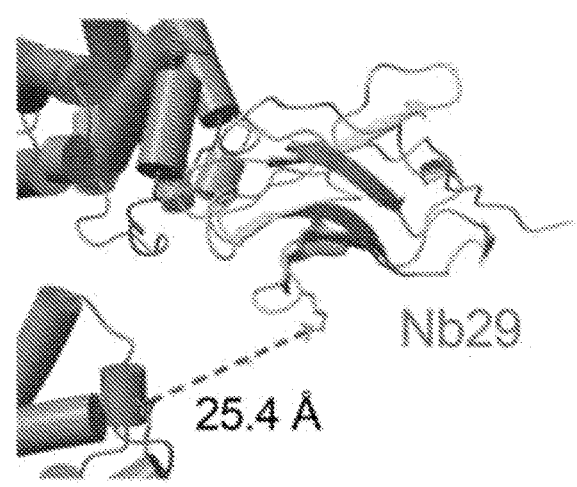
Figure 3G:
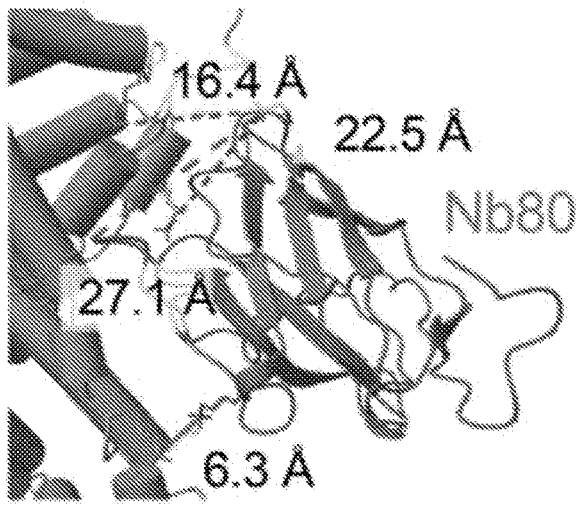

Example 3. Hybrid Structural Characterization of a Tetrameric HSA-Nb Complex To further verify the dominant epitopes and to better understand the structural basis of immunogenicity, an assessment was done to determine a hybrid structure of a tetrameric complex composed of HSA and 3 representative Nbs (Nbs 80, 13 and 29) corresponding to different major epitopes. First, size-exclusion chromatography (SEC) was employed to confirm that 3 Nbs did not co-occupy—i.e., they did not compete for HSA interaction (FIG. 3a); as shown in FIG. 3a, a clear size shift upon the addition of each Nb was observed. The homogenous fraction of the complex was analyzed by negative stain electron microscopy (EM) (FIG. 3b, FIGS. 10b to 10d). Approximately 22,000 EM particles were averaged to reconstruct a 3D density map (FIGS. 3b-3c). Structural models were then computed and the lowest energy models were screened using cross-links to constrain the orientation and localization of the Nbs. The final model was verified by simultaneously satisfying EM, cross-link restraints and mutagenesis (FIGS. 3e-3h).

The overall architecture of the tetrameric complex confirms the major epitopes and is a reminiscence of a Christmas tree in which a "pine tree" of HSA is decorated with three conformational Nb "gifts" at different locations. There are several observations beyond the overall architecture. 1) Nbs do not co-occupy with HSA FcRn binding site to interfere FcRn-mediated endocytosis, a process critical for HSA stability. 2) Good complementarity between the epitope cavities and the concave paratopes of Nbs was confirmed. Interestingly, the shape complementarity correlates with its affinity, with the highest of Nb 80 (160 pM) being nicely matched and the lowest of Nb 29 (approximately 1 nM) relatively poorly matched. Importantly, none of these Nbs co-localize with the reported HSA-Nb (#5VNW, approximately 450 nM $K_D$).

Rich hydrophobic and charged residues on the interfaces were observed, which can explain the high-affinity. To further investigate these interactions, two charged residues (K 383 and E400) on HSA were mutated. Based on the model described herein, these residues can form two crossed, stable salt bridges with the respective opposite charge on Nb CDRs to better mimic camelid residues (FIG. 3i and FIG. 3j). Interestingly, while one mutation E400$^R$ significantly weakened the Nb 80-HSA interaction, double mutants K383$^D$: E400$^R$ completely abolished such a strong interaction (FIG. 3k), further confirming the accuracy of the models described herein. The sequences shown in FIG. 3j are YETTLEKCCAAADPHECYAKVFDEF (SEQ ID NO: 101) and YEATLEDCCAKDDPHACYATVEDKL (SEQ ID NO: 102).

Example 4. Development of an Accurate MS Assay for Multiplexed Nb Pharmacokinetic Analysis A new MS assay was then developed to enable high-throughput, accurate and specific PK analysis of Nbs while reducing the bias and challenges of comparing among a large number of animals. The label-free, fragment-ion-based MS method has good linearity for detection of Nbs in the serum (FIGS. 11a-11e). Since the majority of these HSA-Nbs do not cross-react with mouse albumin, a humanized albumin mouse model (Tg32-Alb$^{-/-}$ mFcRn$^{-/-}$ hFcRn$^{Tg/Tg}$) was chosen-having double knock-out of mAlb and its receptor mFcRn with additional knock-in of hFcRn. It has been reported that when HSA was introduced, it recapitulated the half-life of native HSA in humans.

Figure 12A:
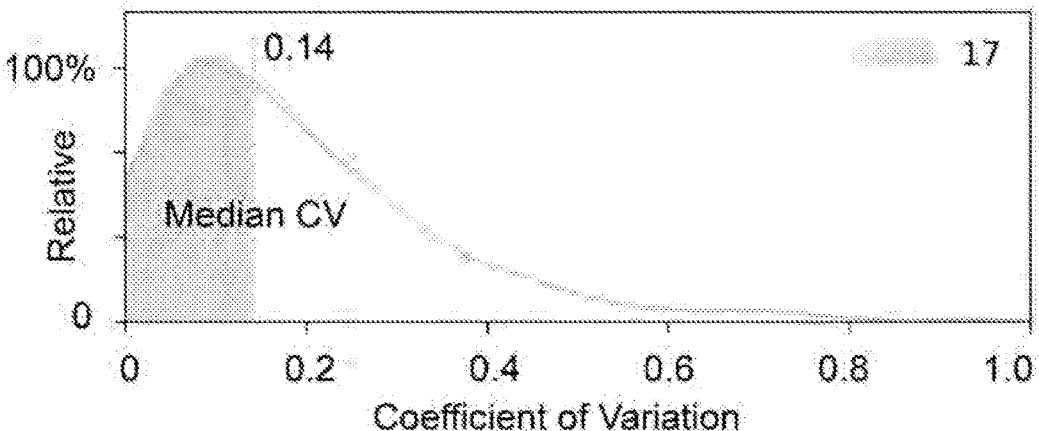
FIGS. 12(a-c) show the accuracy (median coefficient variations or CVs) of the Nb PK measurements from three different mice (12a (mouse 1), 12b (mouse two), 12c (mouse three)).
Figure 12B:
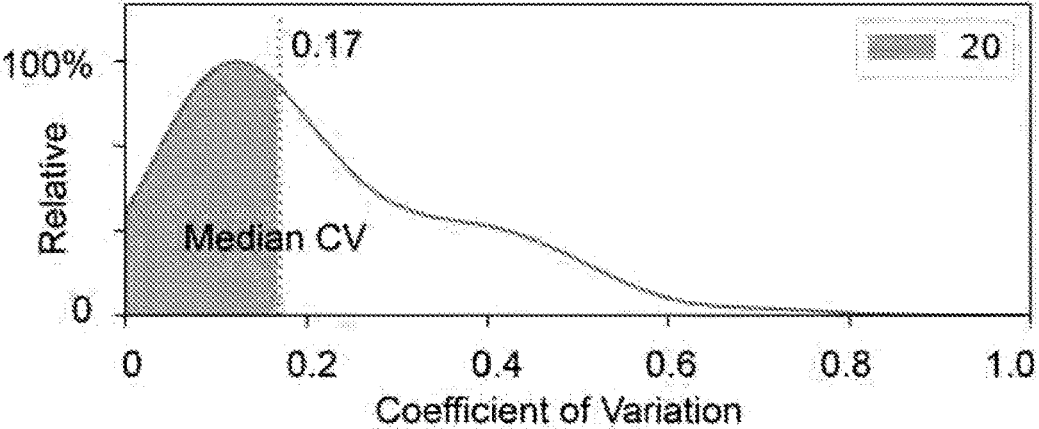
Figure 12C:
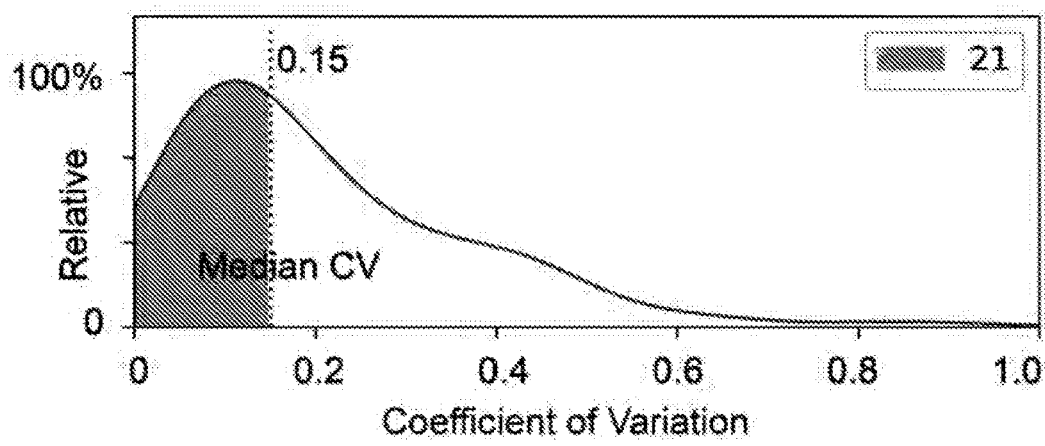

Followed by HSA injection, 22 Nbs including 20 HSA binders and 2 non-binder controls were mixed with equal molarity in PBS and administered to this model (n=3) via single bolus intravenous (i.v.) injections. A molar ratio of 1:5 between Nbs and HSA was used to ensure the presence of an excessive amount of HSA to bind. Blood was sampled at different time points post injection and stored as sera. The sera proteins including Nbs were proteolyzed; the resulting peptides were separated by advanced liquid chromatography (LC) and Nb signature peptides together with their fragment ions were quantified by high-resolution orbitrap MS (FIG. 4a, FIGS. 11a-11e). The average quantification CV based on hundreds of LC runs was 15.3% (FIGS. 12a-12c).

Figures 4A, 4B:
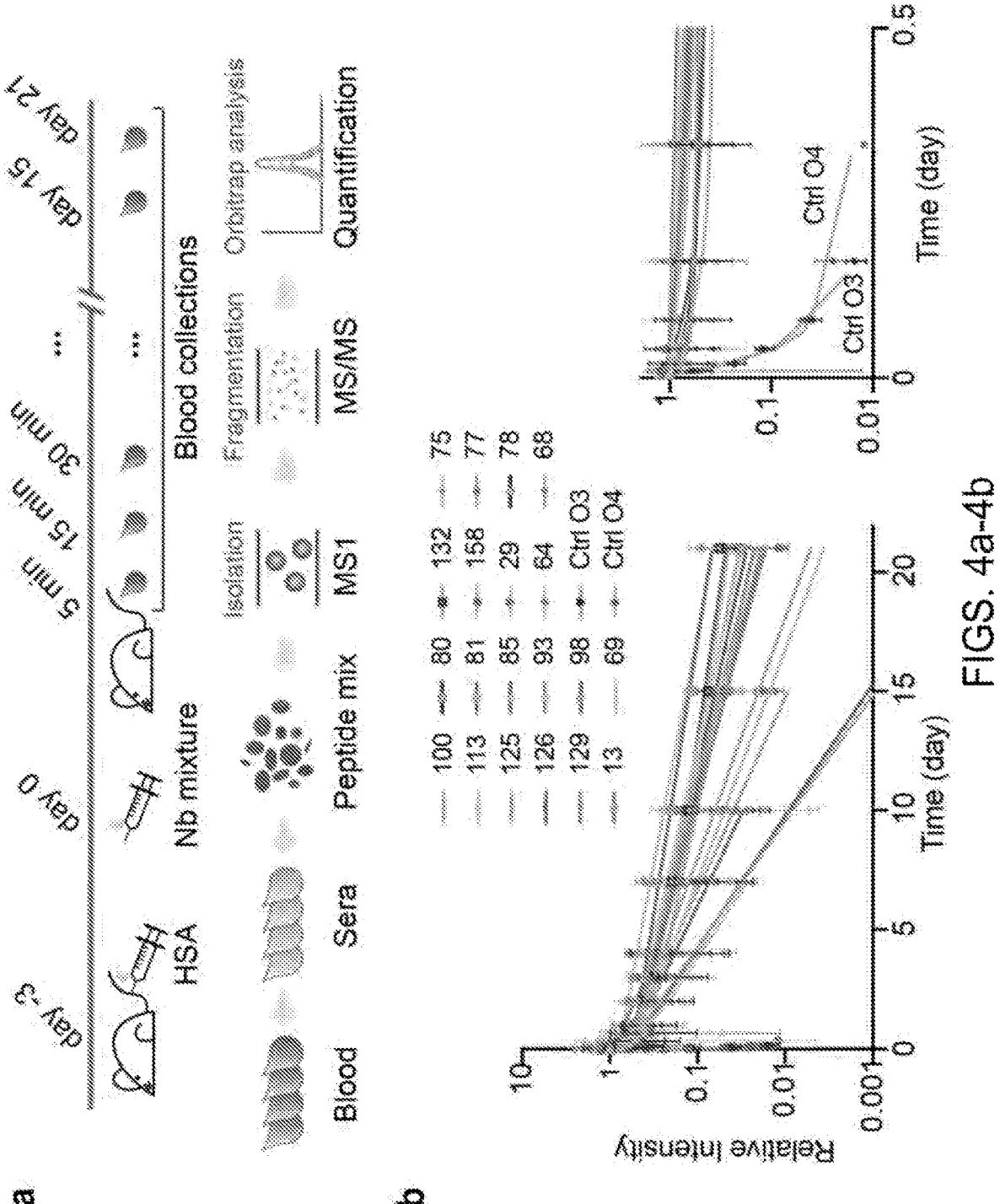
FIG. 4a shows schematics of the MS-based assay for multiplexed PK measurement.
FIG. 4b shows PK analysis of 22 Nbs in a humanized mouse model. Single bolus administration of an equimolar mixture of 22 Nbs including 20 HSA-Nbs and 2 non-binder controls were i.v. injected into three animals. Serum samples were collected at different time points, proteolysed, the resulting peptides were separated by LC and these molecules and their fragment ion products were quantified by an orbitrap QE HFX mass spectrometer. Each data point indicates the median Nb abundance from three different animals. The data was then fitted into a biphasic model to calculate the Nb half-lives.
Figures 4C, 4D:
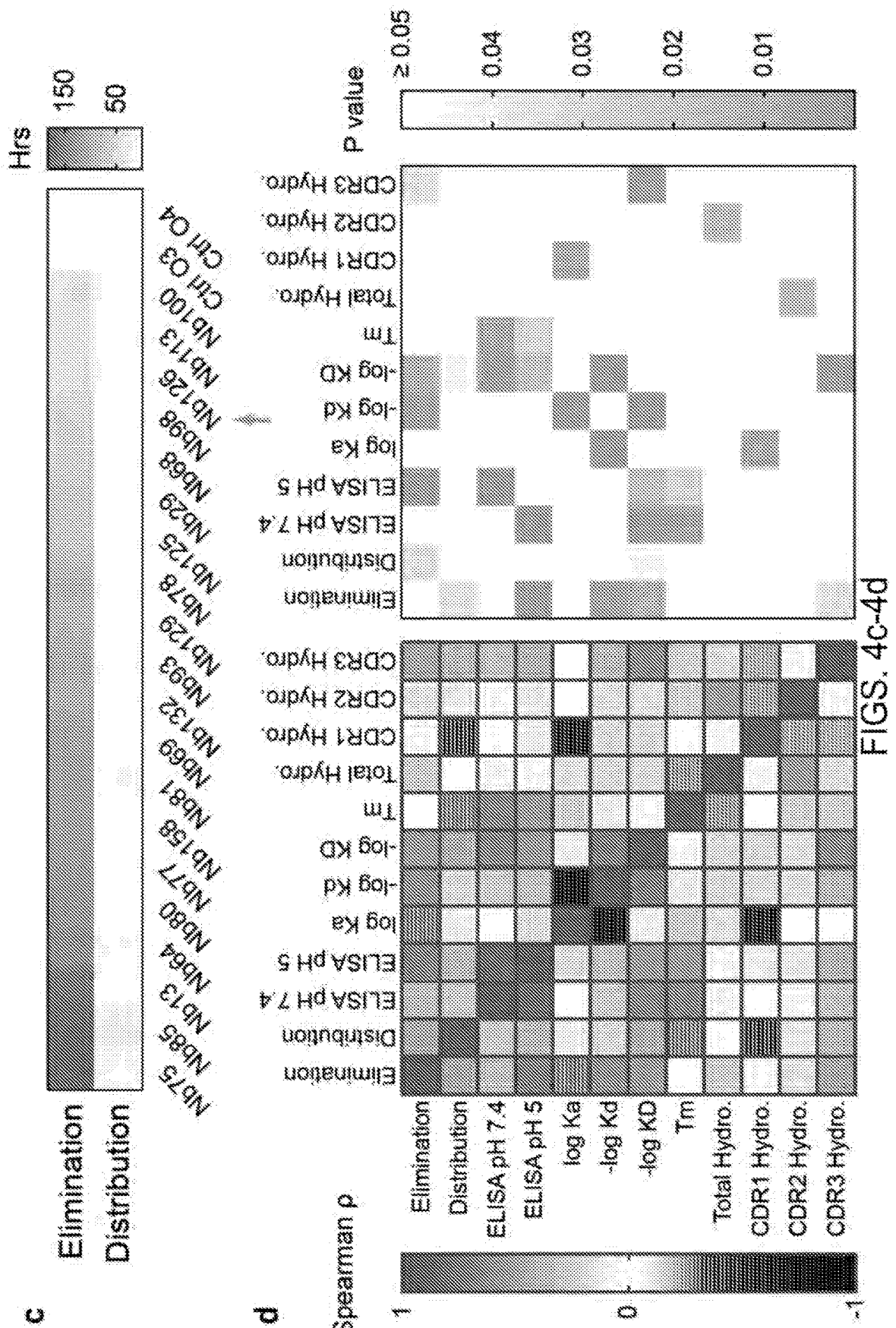
FIG. 4c shows heatmap summary of distribution and elimination of PK.
FIG. 4d shows correlative analysis between PK and the properties of Nbs.
Figure 14:
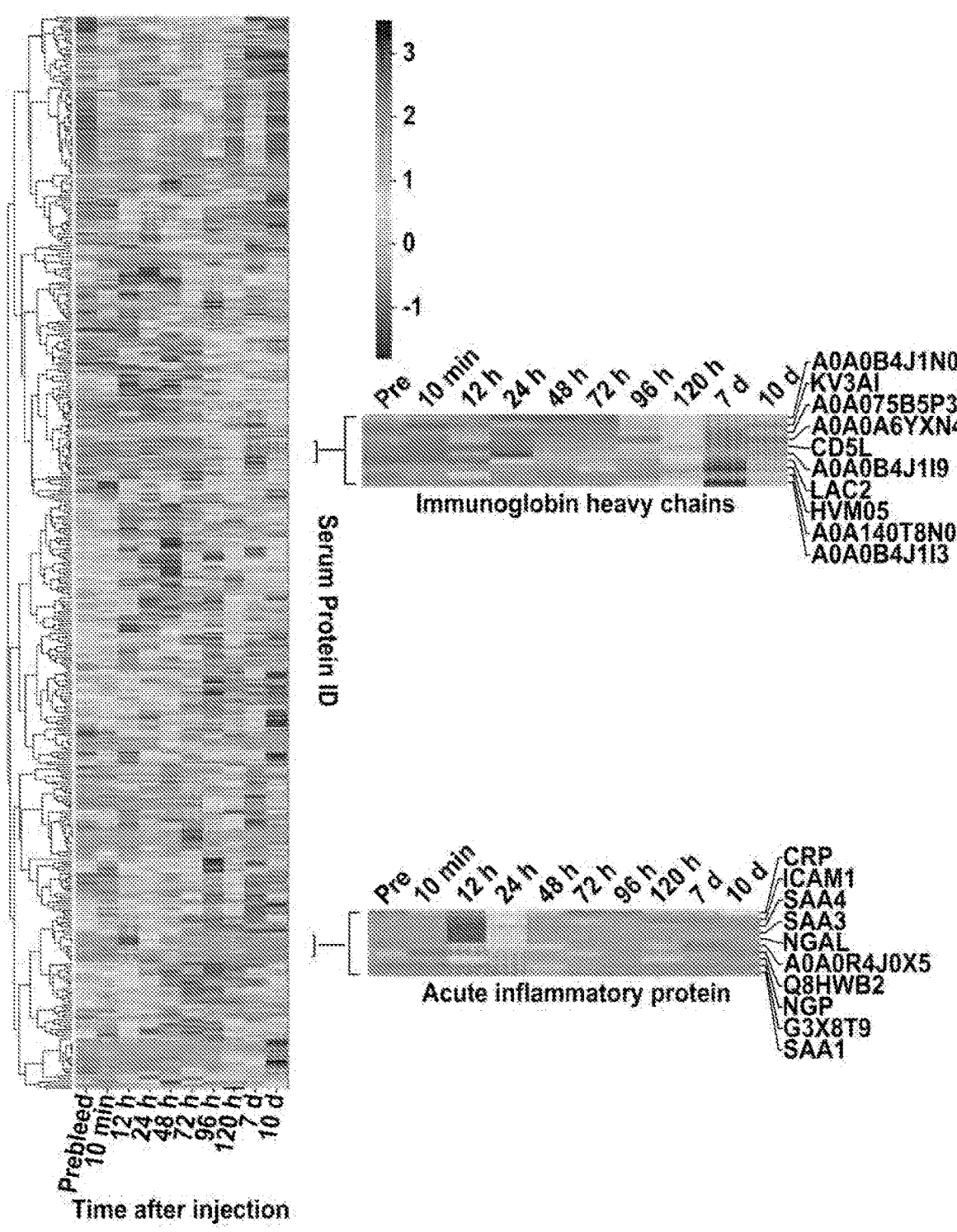
FIG. 14 shows the serum protein quantification upon HSA and Nb administration in the humanized mouse model. At day 7, a significant increase of mouse IgGs was confirmed.

As shown in FIG. 4b, compared with control Nbs whose serum half-life was approximately 26-60 mins, HSA-Nbs showed significantly improved half-lives-up to 771-fold of decreased blood clearance (Nb 158) was observed. Surprisingly, unique and greatly varied T1/2 (from 1.6 days to 7.6 days) was observed (FIG. 4c), which correlates well with the half-life of 8.1 days for HSA (w/o Nb co-injection, FIG. 13c), instead of 21 days as previously reported in this model. Label-free quantitative serum proteomics identified hundreds of fold increase of serum IgG levels 5-6 days post HSA injection indicating the development of an anti-HSA immune response in the model (FIG. 14), which was not unusual for such a well-folded exogenous protein when administered at relatively high dose (still below the full physiological level though).

Example 5. Correlation of Nb Pharmacokinetics and their Physicochemical Properties To better understand the difference of HSA-Nb PKs, correlation analysis was performed (FIG. 4d) between Nb PK and physicochemical properties including affinity (both at 7.4 and acidic pH), melting temperature, isoelectric points and hydrophobicity (at both CDR and whole protein levels). Interestingly, affinity at acidic pH correlates well with elimination rate (spearman ρ=0.78), followed by affinity at neutral pH (in particular, the off rates) and CDR3 hydrophobicity; a reasonable correlation can be found among the three parameters. It is conceivable that both slow binding off-rates and acidic pH-dependent interaction are important to extend the stability of the Nb-HSA-FcRn ternary complex in the endosome; weakened binding leads to early termination of the "hitchhiking" journal, resulting faster elimination of the piggybacked Nb cargos. The data described herein indicate that increased hydrophobicity on the paratope can be important for high-affinity binding.

Example 6. Development of Duraleukins: A Novel Class of Nb-Fusion Cytokine for Cancer Immunotherapy For proof-of-concept, this Nb toolkit was applied to a model therapeutic molecule Interleukin-2 (IL-2). IL-2 is a master cytokine that functions in augmenting both innate and adaptive (e.g., CD8+T and natural killer cells) immune responses to suppress cancer development. As the first cancer immunotherapy drug, human IL-2 (approximately 15 kDa) has been applied to effectively treat multiple cancers such as kidney cancer and advanced melanoma, however, its clinical efficacy remains largely limited by the short half-life (<30-60 minutes in humans). In addition, high-dose, frequent administration of hIL-2, while necessary for its anti-cancer activity, can lead to pronounced side-effects including liver toxicity and vascular leak syndrome.

Figures 5D, 5E, 5F, 5G:
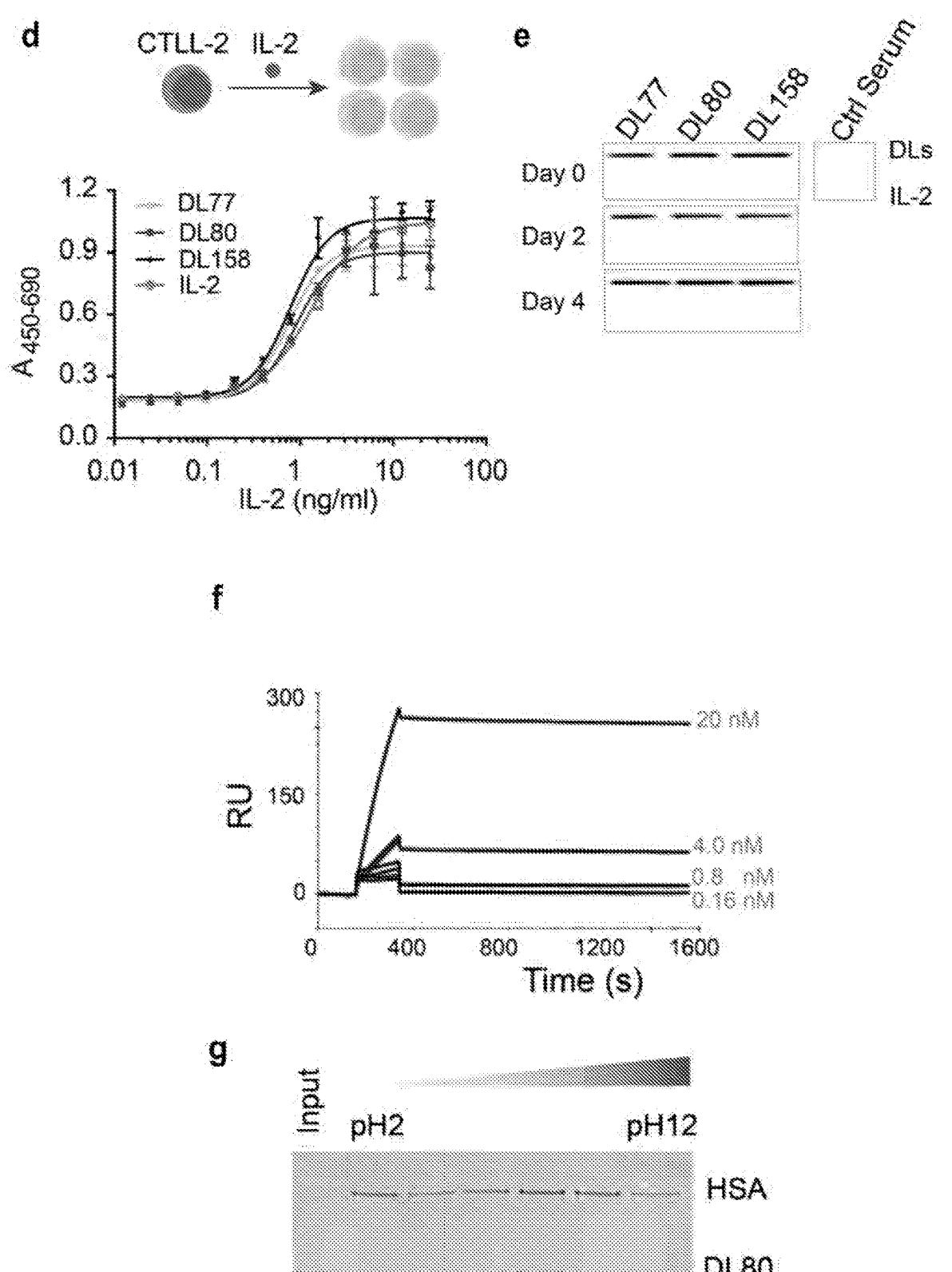
FIG. 5d shows in vitro CTLL-2 cell proliferation assay of Duraleukin and IL-2.
FIG. 5e shows the in vitro stability of Duraluekin in the presence of human serum.
FIG. 5f shows $K_D$ affinity measurement of DL80 for HSA binding. Ka(1/Ms)=1.66e5; Kd(1/s)=2.75e-5; $K_D$=1.66 pM
FIG. 5g shows beads binding assay (pH-dependent) of DL80 for HSA binding. HSA-conjugated agarose resin was used to pull down DL80 in different pH buffers (pH2-pH12). Relatively intensities of the affinity isolated DL80 protein on the SDS PAGE were quantified by Image J.
Figures 7A, 7B, 7C, 7D, 7E, 7F:
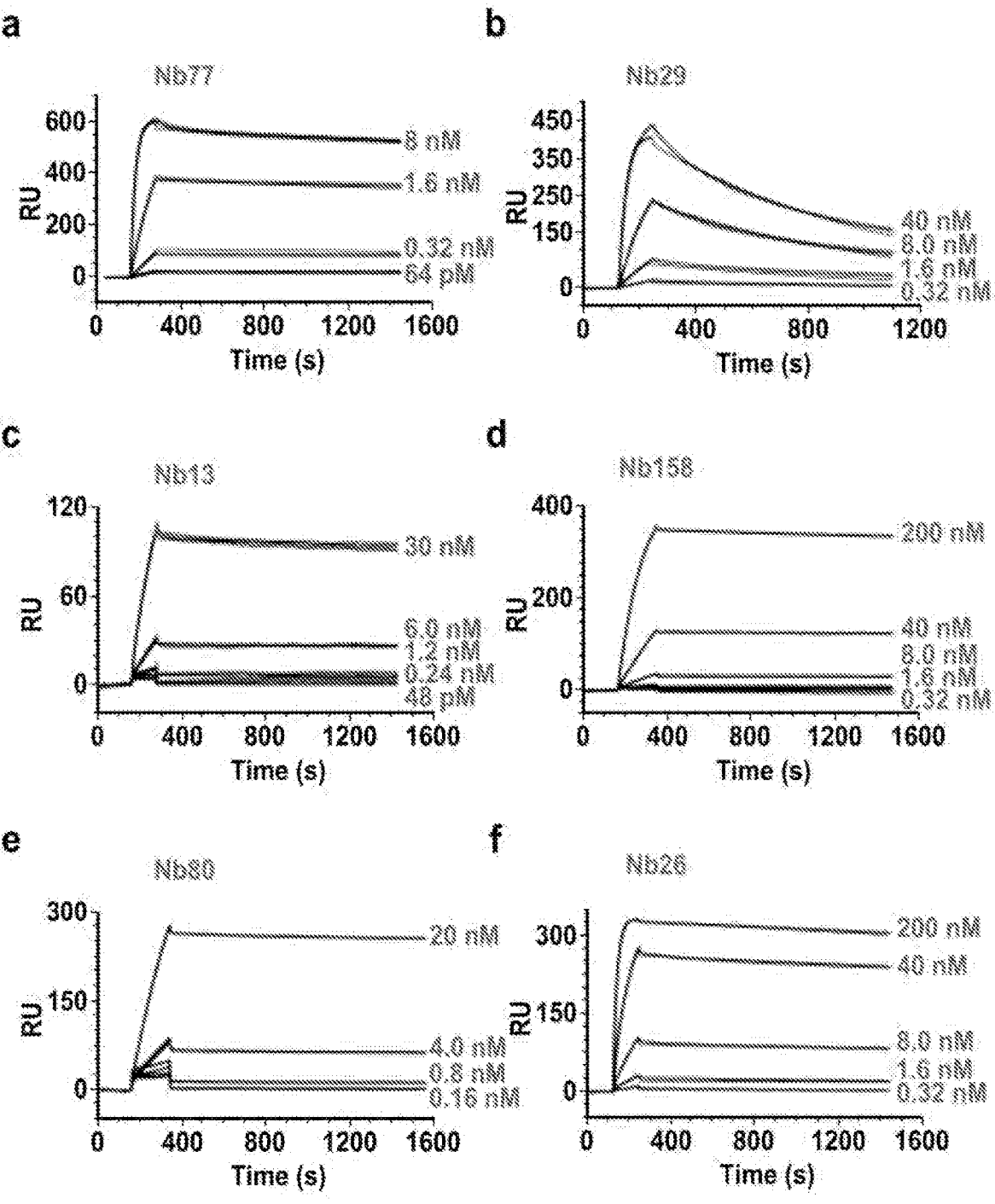
FIG. 7a, Nb77: Ka (1/Ms)=5.68e6; Kd(1/s)=7.68e-5; KD=1.35 pM.
FIG. 7b, Nb29: Ka (1/Ms)=9.73e6; Kd(1/s)=1.9e-3; KD=1.22 nM FIG. 7c, Nb13. Ka (1/Ms)=2.85e5; Kd(1/s)=5.73e-5; KD=201 pM.
FIG. 7d, Nb158: Ka (1/Ms)=1.04e5; Kd(1/s)=3.51e-5; KD=339 pM.
FIG. 7e, Nb80: Ka (1/Ms)=1.66e5; Kd(1/s)=2.75e-5; KD=166 pM.
FIG. 7f, Nb26: Ka (1/Ms)=3.38e5; Kd(1/s)=6.97e-5; KD=206 pM.
Figures 7G, 7H, 7I, 7J, 7K, 7L:
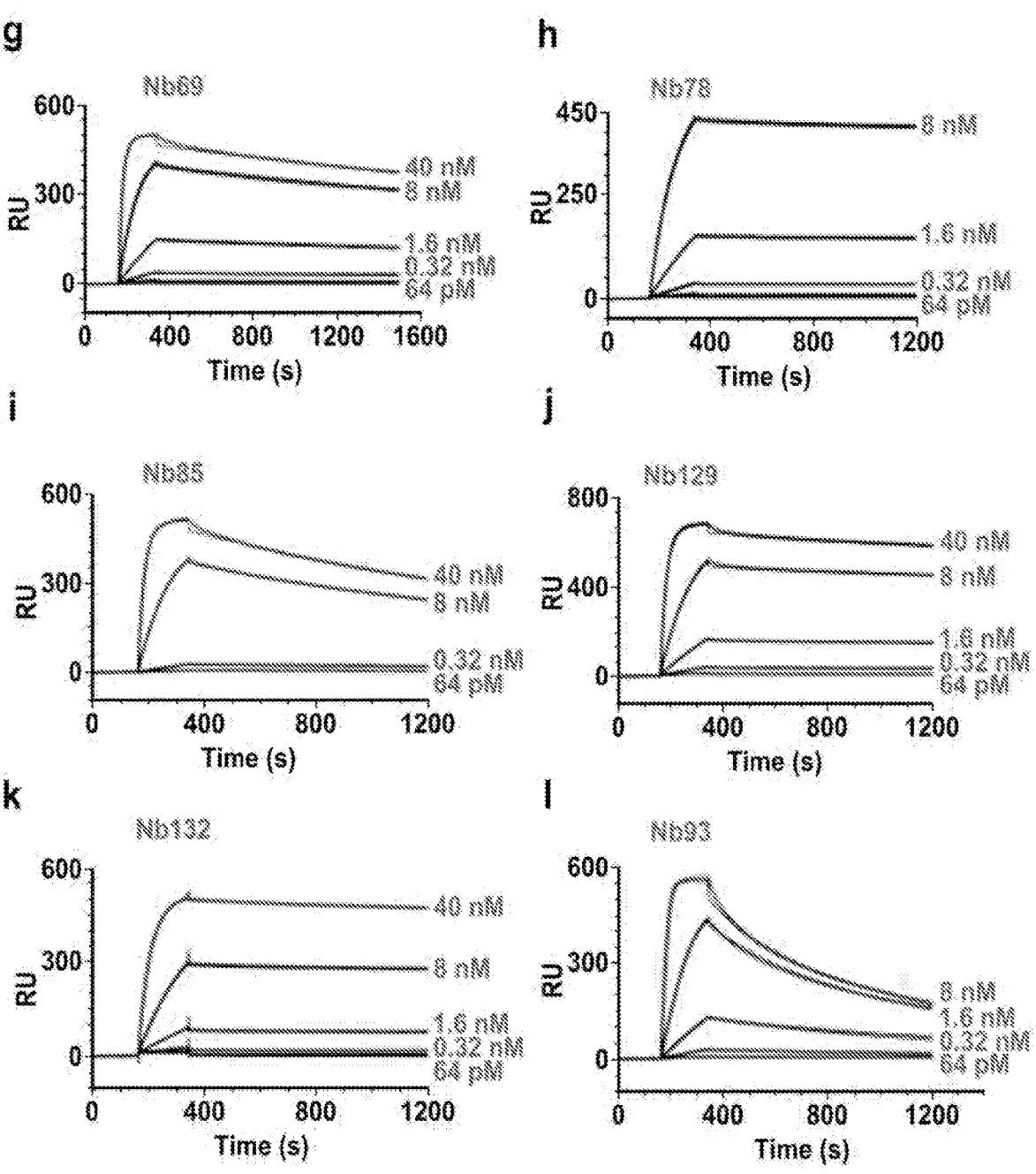
FIG. 7g, Nb69: Ka (1/Ms)=2.7e5; Kd(1/s)=1.97c-4; KD=730 pM.
FIG. 7h, Nb78: Ka (1/Ms)=2.34e5; Kd(1/s)=3.99e-5; KD=170 pM.
FIG. 7i, Nb85: Ka (1/Ms)=1.11e6; Kd(1/s)=5.04e-4; KD=454 pM.
FIG. 7j, Nb129: Ka (1/Ms)=1.03e6; Kd(1/s)=1.14e-4; KD=108 pM.
FIG. 7k, Nb132. Ka (1/Ms)=3.03e5; Kd(1/s)=5.6e-5; KD=185 pM.
FIG. 7l, Nb93. Ka (1/Ms)=1.37e6; Kd(1/s)=1.36e-4; KD=99 pM.
Figures 7M, 7N, 7O, 7P, 7Q, 7R:
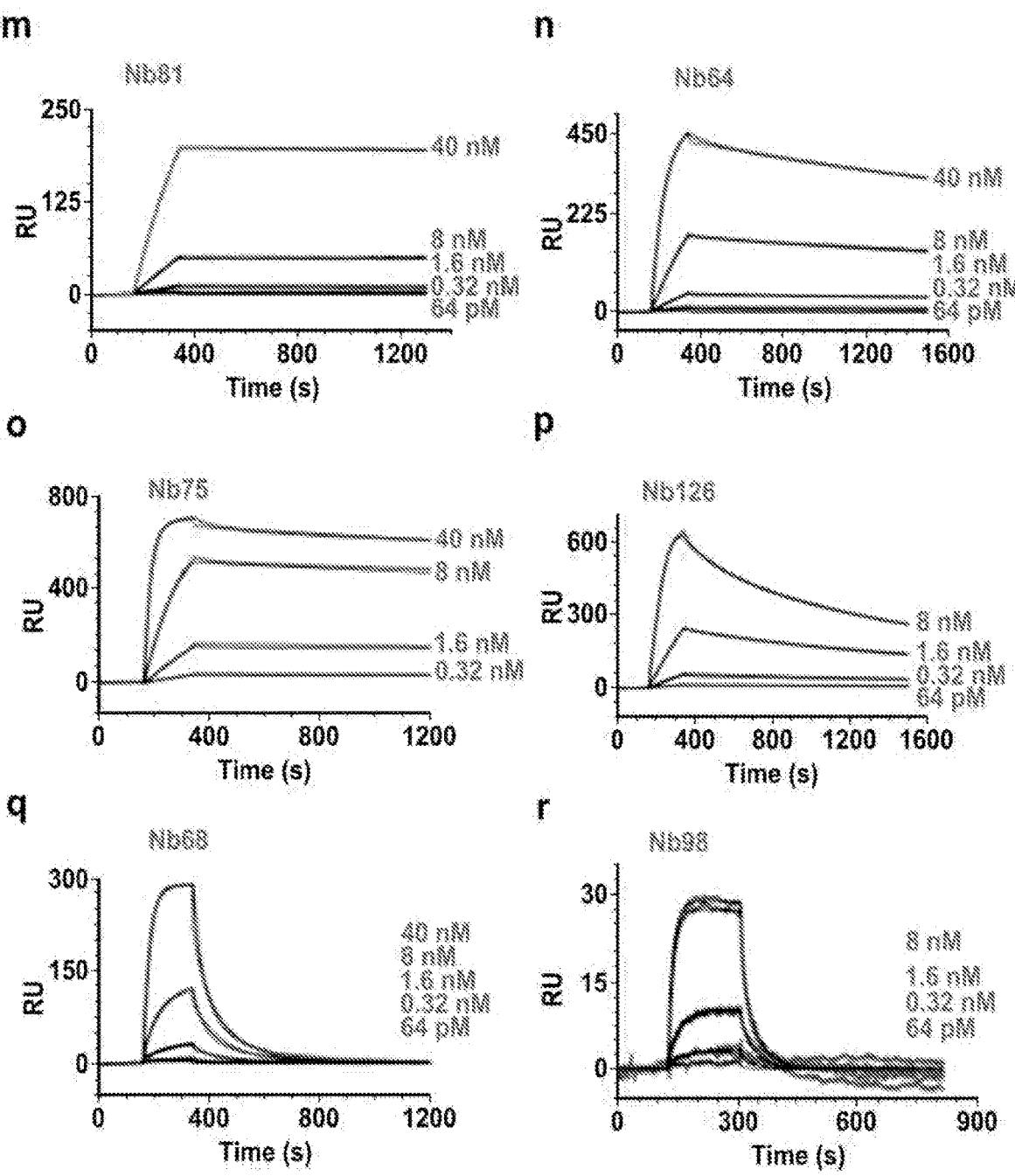
FIG. 7m, Nb81: Ka (1/Ms)=8.82e4; Kd(1/s)=1.42e-5; KD=161 pM.
FIG. 7n, Nb64: Ka (1/Ms)=3.83e5; Kd(1/s)=2.06e-4; KD=538 pM.
FIG. 7o, Nb75: Ka (1/Ms)=1.03e6; Kd(1/s)=1.02e-4; KD=100 pM.
FIG. 7p, Nb126: Ka (1/Ms)=6.92e6, Kd(1/s)=1.74e-3, KD=251 pM.
FIG. 7q, Nb68: Ka (1/Ms)=2.06e6; Kd(1/s)=2.9e-2; KD=14 nM.
FIG. 7r, Nb98: Ka (1/Ms)=1.16e6; Kd(1/s)=2.7e-2; KD=23 nM.

Fusion constructs of various N terminal HSA-Nb followed by bIL-2 was designed to generate novel compositions (these compositions generally referred to as "Duraleukins") (FIG. 5a). Three Duraleukins (DL77, DL80 and DL158) were rapidly produced using Nb77, Nb80 and Nb158 and bulk purified from *E. coli* inclusion bodies (FIG. 5*b*). All constructs demonstrated good thermostability of approximately 60° C. (FIG. 5*c*). They retain comparable bioactivity to hIL-2 as shown in an in vitro CD8+ T cell proliferation assay (FIG. 5*d*), and are very stable when incubated with mouse serum in vitro for days (FIG. 5*e*). Moreover, these Duraleukins (such as DL80) retain high affinity (273 pM) for HSA binding (FIG. 5*f*). While DL80 shows a decrease of affinity at acidic pH (2-8 folds, FIG. 5*g*, it nevertheless possesses one of the highest affinities towards mouse albumin and was selected for in vivo evaluation.

Figure 15:
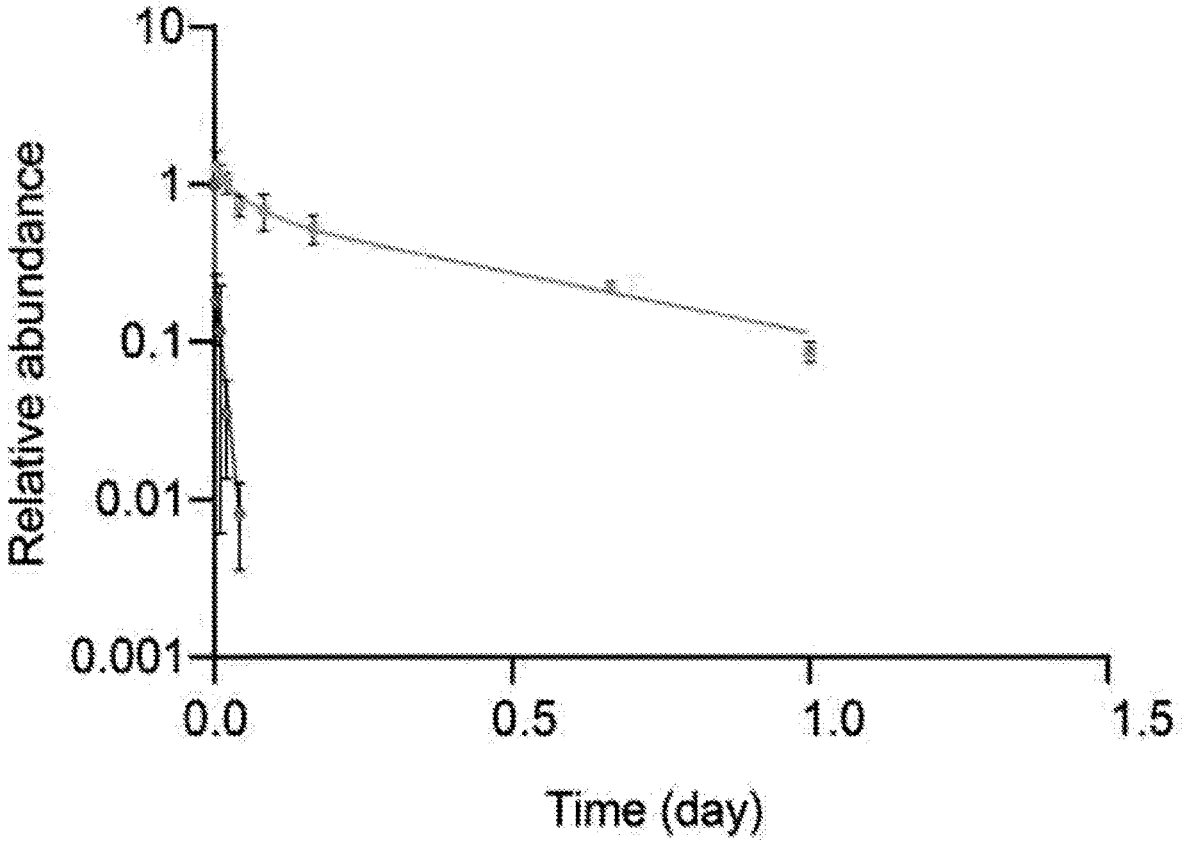
FIG. 15 shows the pharmacokinetic analysis of IL-2 (open circles) and DL80 (filled squares) in the wild-type C57BL/6J mouse model. Half-life (slow) for IL-2 is 0.0086; half-life (fast) for IL-2 is about 2.7 e-0.06. Half-life (slow) for Duraleukin 80 is 0.40; half-life (fast) for Duraleukin 80 is 0.039.

Example 7. Evaluation of Therapeutic Efficacy of DL80 for Melanoma Treatment A wild type B6 mouse model was used to confirm that DL80 had a prolonged stability compared to hIL-2 with approximately 46-fold improvement on blood elimination (FIG. 15). Then the therapeutic efficacy of DL80 was assessed in the B16F10 melanoma mouse model. Tumor-bearing mice were subcutaneously administered with equimolarity of DL80 or hIL-2 at each injection but with different frequencies (DL80 every 6 days; hIL-2 on a daily basis) for a total of 24-day treatment. TA99—a mAb that recognizes tumor marker TRP1, and is well known for its synergistic activity of IL-2, was co-treated for both groups at a dose of 150 μg every 6 days. After treatment, the animals were allowed to recover, and were continuously analyzed for tumor size (FIG. 6*a*) and survival (FIG. 6*b*) for a month. Despite using only 1/% of the therapeutic dose of hIL-2 and the fact that only a moderate improvement of PK for the fusion construct DL80 was observed in the WT B6 mouse model, both DL80 and hIL-2 treated groups exhibited significant reductions in tumor loads and overall survival compared to PBS control. 50% (4 mice) of DL80 treated melanoma animals survived compared with 25% (2 mice) in hIL-2 and 0% in PBS group. A near-complete tumor recession was observed in the DL80 responded animals, whereas a clear rebounding of tumorigenesis in the hIL-2 treated mice was evident (FIG. 6*a*), indicating the superiority of Duraleukin for cancer treatment. To further explore the potential mechanism(s) of its antitumor effect, tumors at different stages post treatment were isolated and their respective immune cells were analyzed by flow cytometry (FIG. 6*c*). While no significant changes were detected at day 1 post treatment, significant increases of both CD8+ T cells and natural killer (NK) cells were observed in the DL80-treated tissues at day 3 post injection, indicating Duraleukin effectively penetrated tumors stimulating these immune cells to exert its antitumor activity.

Example 8. HSA-Binding Nbs Improves the Stability and Therapeutic Effects of Drugs Numerous small biomolecules and therapeutic agents (including Nbs) are limited by their poor stability in vivo. Here, encouraged by the outstanding physicochemical and biophysical properties of camelid Nbs, a robust, generic approach was developed to address this fundamental issue of drug delivery. A large cohort of high-quality HSA-Nbs have been systematically characterized by using cutting-edge multidisciplinary approaches spanning biophysics, proteomics, structural biology and computational modeling. A new proteomics method was developed for accurate, high-throughput measurement of Nb PK. A stable Nb-fusion cytokine Duraleukin was then developed and its antitumor efficacy has been preferentially characterized.

Four dominant epitopes on HSA were discovered (a decorated Xmas tree) supporting the immunodominance hypothesis. A preference of concavity recognition by Nbs was observed, which might be explained by the convexity of Nb architectures. Despite having relatively small paratopes, the majority of our Nos can still achieve outstanding affinity and specificity for antigen engagement comparable to IgGs.

Given the high serum concentration of albumin, one would imagine that high affinity of Nbs is not required for the extended PK. The results described above indicate the opposite: that both affinity and pH-dependent binding are positively correlated, underscoring the importance of the microenvironments for the FcRn-mediate endocytosis and the local concentration of the receptor complex for efficient cargo delivery.

Example 9. Methods

Nb DNA synthesis and cloning. Nb genes were codon-optimized for expression in *Escherichia coli* and the nucleotides were in vitro synthesized (Synbiotech). After verification by Sanger sequencing, the Nb genes were cloned into a pET-21b (+) vector at BamHI and Xhol, or EcoRI and NotI restriction sites.

Purification of recombinant Nbs. Nb DNA constructs were transformed into BL21 (DE3) cells and plated on Agar with 50 μg/ml ampicillin at 37° C. overnight. A single bacterial colony was picked for LB broth media and IPTG Nb protein induction. Briefly, 0.5 mM IPTG was added to the *E. coli* cell culture when O.D. reached approximately 0.4-0.6, and Nb was induced at 16° C. overnight. Cells were then harvested, briefly sonicated and lysed on ice with lysis buffer (1×PBS, 150 mM NaCl, 0.2% TX-100 with protease inhibitor). After lysis, soluble protein extract was collected at 15,000×g for 10 mins and recombinant Nbs were purified by His6-Cobalt resin (Thermo) and eluted by imidazole. The eluted Nbs were subsequently dialyzed in the dialysis buffer (e.g., 1×DPBS, pH 7.4) and stored at −80 before use.

ELISA (Enzyme-linked immimosorbent assay). Indirect ELISA was carried out to evaluate immune responses and nanobody affinity. Antigen was coated onto 96-well ELISA plate (R&D system) at 1-10 ng/well in coating buffer (15 mM sodium carbonate, 35 mM sodium bicarbonate, pH 9.6) overnight at 4° C. and was blocked with blocking buffer (DPBS, 0.05% Tween 20, 5% milk) at room temperature for 2 hrs. The immunized serum or nanobodies were serially diluted in blocking buffer and incubated with the antigen for 2 hrs. HRP conjugated secondary antibodies against llama Fc (Thermo) or his-tag (Genscript) were diluted 1:5,000-10,000 in the blocking buffer and incubated for 1 h at room temperature. Three washes with 1×PBST (DPBS, 0.05% Tween 20) were carried out to remove nonspecific absorbances. After washes, the samples were further incubated under dark with freshly prepared w3,3',5,5'-Tetramethylbenzidine (TMB) substrate for 10 mins at room temperature to develop the signals. After the STOP solution (R&D system), the plates were read at multiple wavelengths (the optical density at 550 nm wavelength subtracted from the density at 450 nm) on a plate reader (Multiskan GO, Thermo Fisher). Raw data was then processed by Prism 7 (GraphPad) to fit into a 4PL curve and to calculate log ICS0 or average value if the result did not fit into a curve.

In vitro beads pull down. Nb Affinity measurement by surface plasmon resonance (SPR) Surface plasmon resonance (SPR, Biacore 3000 system, GE Healthcare) was used to measure Nb affinities. Briefly, a protein antigen such as GST, OMP25 PDZ domain or human serum albumin was immobilized to the flow channels of an activated CM5 sensor-chip. Protein analytes were diluted to 10-30 µg/ml in 10 mM sodium acetate, pH 4.5, and injected into the SPR system at 5 µl/min for 420 s. The surface was then blocked by 1 M ethanolamine-HCl (pH 8.5). For each Nb analyte, a series of dilution spanning approximately 1,000 fold was injected in duplicate, with HBS-EP+ running buffer (GE-Healthcare) containing 2 mM DTT, at a flow rate of 20-30 µl/min for 120-180 s, followed by a dissociation time of 5-20 mins based on dissociation rate. Between each injection, the sensor chip surface was regenerated with low pH buffer containing 10 mM glycine-HCl (pH 1.5-2.5) at a flow rate of 40-50 µl/min for 30 s, or high pH buffer of 20-40 mM NaOH (pH 12-13) at 40-50 µl/min for 30 s. Binding sensorgrams for each Nb were processed and analyzed using BIA evaluation by fitting with 1:1 Langmuir model or 1:1 Langmuir model with mass transfer.

What is claimed is:

1. A recombinant nanobody comprising a human serum albumin (HSA) binding polypeptide and an interleukin-2 (IL-2) polypeptide, wherein the HSA binding polypeptide specifically binds to an HSA epitope selected from the group consisting of epitope 1, epitope 2, epitope 3, and epitope 4, wherein epitope 1 comprises, as determined starting from amino acid residue 25 of SEQ ID NO: 1, the amino acid residues 298-307, 311, 332-341, and 371-386 of SEQ ID NO: 1, wherein epitope 2 comprises, as determined starting from amino acid residue 25 of SEQ ID NO: 1, the amino acid residues 5-13, 62-67, 93-99, and 228-266 of SEQ ID NO: 1, wherein epitope 3 comprises, as determined starting from amino acid residue 25 of SEQ ID NO: 1, the amino acid residues 226-230 and 298-337 of SEQ ID NO: 1, and wherein epitope 4 comprises, as determined starting from amino acid residue 25 of SEQ ID NO: 1, the amino acid residues 33-38 and 111-145 of SEQ ID NO: 1; and wherein the HSA binding polypeptide comprises an amino acid sequence selected from the group consisting of SEQ ID NO: 2, SEQ ID NO: 3, and SEQ ID NO: 4.

2. The recombinant nanobody of claim 1, wherein the HSA binding polypeptide specifically binds to a human HSA and a mouse serum albumin.

3. The recombinant nanobody of claim 1, wherein the IL-2 polypeptide comprises the amino acid sequence of SEQ ID NO: 5, SEQ ID NO: 103, or a functional fragment thereof.

4. The recombinant nanobody of claim 1, wherein the HSA binding polypeptide is linked to the IL-2 polypeptide via a linker.

5. The recombinant nanobody of claim 4, wherein the linker comprises the amino acid sequence of SEQ ID NO: 6.

6. The recombinant nanobody of claim 1, wherein the recombinant nanobody is less than about 50 kDa.

7. The recombinant nanobody of claim 1, wherein the HSA binding polypeptide does not decrease an affinity between the IL-2 polypeptide and an IL-2 receptor thereof.

8. The recombinant nanobody of claim 1, wherein the recombinant nanobody comprises an amino acid sequence selected from the group consisting of SEQ ID NO: 7, SEQ ID NO: 8, and SEQ ID NO: 9.

9. A method of treating a cancer responsive to interleukin-2 (IL-2) in a subject in need thereof, comprising administering a therapeutically effective amount of a recombinant nanobody comprising a human serum albumin (HSA) binding polypeptide and an IL-2 polypeptide, wherein the HSA binding polypeptide specifically binds to an HSA epitope selected from the group consisting of epitope 1, epitope 2, epitope 3, and epitope 4, wherein epitope 1 comprises, as determined starting from amino acid residue 25 of SEQ ID NO: 1, the amino acid residues 298-307, 311, 332-341, and 371-386 of SEQ ID NO: 1, wherein epitope 2 comprises, as determined starting from amino acid residue 25 of SEQ ID NO: 1, the amino acid residues 5-13, 62-67, 93-99, and 228-266 of SEQ ID NO: 1, wherein epitope 3 comprises, as determined starting from amino acid residue 25 of SEQ ID NO: 1, the amino acid residues 226-230 and 298-337 of SEQ ID NO: 1, and wherein epitope 4 comprises, as determined starting from amino acid residue 25 of SEQ ID NO: 1, the amino acid residues 33-38 and 111-145 of SEQ ID NO: 1; and wherein the HSA binding polypeptide comprises an amino acid sequence selected from the group consisting of SEQ ID NO: 2, SEQ ID NO: 3, and SEQ ID NO: 4.

10. The method of claim 9, wherein the HSA binding polypeptide specifically binds to a human HSA and a mouse serum albumin.

11. The method of claim 9, wherein the IL-2 polypeptide comprises the amino acid sequence of SEQ ID NO: 5, SEQ ID NO: 103, or a functional fragment thereof.

12. The method of claim 9, wherein the HSA binding polypeptide is linked to the IL-2 polypeptide via a linker.

13. The method of claim 12, wherein the linker comprises the amino acid sequence of SEQ ID NO: 6.

14. The method of claim 9, wherein the recombinant nanobody is less than about 50 kDa.

15. The method of claim 9, wherein the HSA binding polypeptide does not decrease an affinity between the IL-2 polypeptide and an IL-2 receptor thereof.

16. The method of claim 9, wherein the recombinant nanobody comprises an amino acid sequence selected from the group consisting of SEQ ID NOs: 7, SEQ ID NO: 8, and SEQ ID NO: 9.

17. The method of claim 9, wherein the recombinant nanobody has an in vivo half-life about 100 times higher than a natural IL-2 polypeptide.

18. The method of claim 9, wherein the cancer is selected from the group consisting of melanoma and renal carcinoma.

19. The recombinant nanobody of claim 1, wherein the HSA binding polypeptide comprises the amino acid sequence of SEQ ID NO: 2.

20. The recombinant nanobody of claim 1, wherein the HSA binding polypeptide comprises the amino acid sequence of SEQ ID NO: 3.

21. The recombinant nanobody of claim 1, wherein the HSA binding polypeptide comprises the amino acid sequence of SEQ ID NO: 4.

22. The recombinant nanobody of claim 1, wherein the recombinant nanobody comprises the amino acid sequence of SEQ ID NO: 7.

23. The recombinant nanobody of claim 1, wherein the recombinant nanobody comprises the amino acid sequence of SEQ ID NO: 8.

24. The recombinant nanobody of claim 1, wherein the recombinant nanobody comprises the amino acid sequence of SEQ ID NO: 9.

* * * * *

```
                          SEQUENCE LISTING

<160> NUMBER OF SEQ ID NOS: 103

<210> SEQ ID NO 1
<211> LENGTH: 609
<212> TYPE: PRT
<213> ORGANISM: Homo sapiens

<400> SEQUENCE: 1

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
```

-continued

```
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
                355                 360                 365

Leu Leu Leu Arg Leu Ala Lys Thr Tyr Glu Thr Thr Leu Glu Lys Cys
            370                 375                 380

Cys Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
                435                 440                 445

Glu Val Ser Arg Asn Leu Gly Lys Val Gly Ser Lys Cys Cys Lys His
            450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
                530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
            595                 600                 605

Leu

<210> SEQ ID NO 2
<211> LENGTH: 124
<212> TYPE: PRT
<213> ORGANISM: Artificial Sequence
<220> FEATURE:
<223> OTHER INFORMATION: Synthetic construct

<400> SEQUENCE: 2

Ala Gln Val Gln Leu Val Glu Ser Gly Gly Gly Leu Val Gln Ala Gly
1               5                   10                  15

Gly Ser Leu Arg Leu Ser Cys Thr Ala Ser Gly Arg Thr Tyr Glu Pro
            20                  25                  30

Leu Val Met Gly Trp Phe Arg Gln Ala Pro Gly Lys Glu Arg Glu Phe
            35                  40                  45

Val Ala Thr Ile Thr Pro Ser Gly Gly Ser Leu Ser Tyr Ala Asp Ser
        50                  55                  60
```

-continued

```
Val Lys Gly Arg Phe Thr Val Ser Arg Asp Asn Ala Lys Lys Thr Val
65                  70                  75                  80

Tyr Leu Gln Met Asn Arg Leu Gln Pro Glu Asp Thr Ala Val Tyr Tyr
                85                  90                  95

Cys Ala Ala Pro Gly Val Gly Asn Tyr Arg Tyr Thr Arg Gln Tyr
            100                 105                 110

Asp Tyr Trp Gly Gln Gly Thr Gln Val Thr Val Ser
        115                 120

<210> SEQ ID NO 3
<211> LENGTH: 124
<212> TYPE: PRT
<213> ORGANISM: Artificial Sequence
<220> FEATURE:
<223> OTHER INFORMATION: Synthetic construct

<400> SEQUENCE: 3

Ala Glu Val Gln Leu Val Glu Ser Gly Gly Gly Leu Val Gln Ala Gly
1               5                   10                  15

Gly Ser Leu Arg Leu Ser Cys Thr Ala Ser Gly Arg Thr Phe Thr Pro
            20                  25                  30

Tyr Thr Met Gly Trp Phe Arg Gln Ala Pro Gly Lys Glu Arg Glu Phe
        35                  40                  45

Val Ala Ser Ile Leu Trp Ser Gly Asn Asn Arg Asp Tyr Ala Asp Ser
    50                  55                  60

Val Lys Gly Arg Phe Ala Ile Ser Arg Asp Asn Ala Lys Asn Thr Ala
65                  70                  75                  80

Tyr Leu Gln Met Thr Ser Leu Lys Pro Glu Asp Thr Ala Val Tyr Tyr
                85                  90                  95

Cys Ala Ala Gly Asp Gly Leu Gly Phe Tyr Arg Ser Val Asn Gln Tyr
            100                 105                 110

Asp Tyr Trp Gly Gln Gly Thr Gln Val Thr Val Ser
        115                 120

<210> SEQ ID NO 4
<211> LENGTH: 122
<212> TYPE: PRT
<213> ORGANISM: Artificial Sequence
<220> FEATURE:
<223> OTHER INFORMATION: Synthetic construct

<400> SEQUENCE: 4

Ala Asp Val Gln Leu Val Glu Ser Gly Gly Gly Leu Val Gln Ala Gly
1               5                   10                  15

Gly Ser Leu Arg Leu Ser Cys Ala Ala Ser Gly Gly Thr Ile Ser Asn
            20                  25                  30

Tyr Gly Met Gly Trp Leu Arg Gln Gly Pro Gly Lys Glu Arg Glu Phe
        35                  40                  45

Val Gly Ser Ile Asn Trp Asn Gly Ala Thr Thr His Tyr Ala Asp Ser
    50                  55                  60

Val Lys Gly Arg Phe Ile Ile Ser Arg Asp Asn Ala Lys Asn Thr Val
65                  70                  75                  80

Tyr Leu Gln Met Asn Ser Leu Lys Pro Glu Asp Thr Gly Val Tyr Tyr
                85                  90                  95

Cys Val Ala Gln Phe Ser Val Gln Pro Thr Leu Gln Thr Tyr Asp Tyr
            100                 105                 110

Arg Gly Gln Gly Thr Gln Val Thr Val Ser
```

```
                  115                    120

<210> SEQ ID NO 5
<211> LENGTH: 133
<212> TYPE: PRT
<213> ORGANISM: Homo sapiens

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
            115                 120                 125

Ile Ser Thr Leu Thr
        130

<210> SEQ ID NO 6
<211> LENGTH: 9
<212> TYPE: PRT
<213> ORGANISM: Artificial Sequence
<220> FEATURE:
<223> OTHER INFORMATION: Synthetic construct

<400> SEQUENCE: 6

Arg Asp Pro Glu Asn Leu Tyr Phe Gln
1               5

<210> SEQ ID NO 7
<211> LENGTH: 305
<212> TYPE: PRT
<213> ORGANISM: Artificial Sequence
<220> FEATURE:
<223> OTHER INFORMATION: Synthetic construct

<400> SEQUENCE: 7

Met Ala Ser Met Thr Gly Gly Gln Gln Met Gly Arg Asp Pro Glu Asn
1               5                   10                  15

Leu Tyr Phe Gln Gly Ala Gln Val Gln Leu Val Glu Ser Gly Gly Gly
            20                  25                  30

Leu Val Gln Ala Gly Gly Ser Leu Arg Leu Ser Cys Thr Ala Ser Gly
        35                  40                  45

Arg Thr Tyr Glu Pro Leu Val Met Gly Trp Phe Arg Gln Ala Pro Gly
    50                  55                  60

Lys Glu Arg Glu Phe Val Ala Thr Ile Thr Pro Ser Gly Gly Ser Leu
65                  70                  75                  80

Ser Tyr Ala Asp Ser Val Lys Gly Arg Phe Thr Val Ser Arg Asp Asn
                85                  90                  95

Ala Lys Lys Thr Val Tyr Leu Gln Met Asn Arg Leu Gln Pro Glu Asp
```

```
                100                 105                 110

Thr Ala Val Tyr Tyr Cys Ala Ala Ala Pro Gly Val Gly Asn Tyr Arg
        115                 120                 125

Tyr Thr Arg Gln Tyr Asp Tyr Trp Gly Gln Gly Thr Gln Val Thr Val
        130                 135                 140

Ser Glu Pro Lys Thr Pro Lys Gly Glu Phe Gly Gly Gly Gly Ser Gly
145                 150                 155                 160

Gly Gly Gly Ser Ala Pro Thr Ser Ser Ser Thr Lys Lys Thr Gln Leu
                165                 170                 175

Gln Leu Glu His Leu Leu Leu Asp Leu Gln Met Ile Leu Asn Gly Ile
                180                 185                 190

Asn Asn Tyr Lys Asn Pro Lys Leu Thr Arg Met Leu Thr Phe Lys Phe
                195                 200                 205

Tyr Met Pro Lys Lys Ala Thr Glu Leu Lys His Leu Gln Cys Leu Glu
        210                 215                 220

Glu Glu Leu Lys Pro Leu Glu Glu Val Leu Asn Leu Ala Gln Ser Lys
225                 230                 235                 240

Asn Phe His Leu Arg Pro Arg Asp Leu Ile Ser Asn Ile Asn Val Ile
                245                 250                 255

Val Leu Glu Leu Lys Gly Ser Glu Thr Thr Phe Met Cys Glu Tyr Ala
                260                 265                 270

Asp Glu Thr Ala Thr Ile Val Glu Phe Leu Asn Arg Trp Ile Thr Phe
        275                 280                 285

Ala Gln Ser Ile Ile Ser Thr Leu Thr Leu Glu His His His His His
    290                 295                 300

His
305

<210> SEQ ID NO 8
<211> LENGTH: 305
<212> TYPE: PRT
<213> ORGANISM: Artificial Sequence
<220> FEATURE:
<223> OTHER INFORMATION: Synthetic construct

<400> SEQUENCE: 8

Met Ala Ser Met Thr Gly Gly Gln Gln Met Gly Arg Asp Pro Glu Asn
1               5                   10                  15

Leu Tyr Phe Gln Gly Ala Glu Val Gln Leu Val Glu Ser Gly Gly Gly
                20                  25                  30

Leu Val Gln Ala Gly Gly Ser Leu Arg Leu Ser Cys Thr Ala Ser Gly
        35                  40                  45

Arg Thr Phe Thr Pro Tyr Thr Met Gly Trp Phe Arg Gln Ala Pro Gly
        50                  55                  60

Lys Glu Arg Glu Phe Val Ala Ser Ile Leu Trp Ser Gly Asn Asn Arg
65                  70                  75                  80

Asp Tyr Ala Asp Ser Val Lys Gly Arg Phe Ala Ile Ser Arg Asp Asn
                85                  90                  95

Ala Lys Asn Thr Ala Tyr Leu Gln Met Thr Ser Leu Lys Pro Glu Asp
            100                 105                 110

Thr Ala Val Tyr Tyr Cys Ala Ala Gly Asp Gly Leu Gly Phe Tyr Arg
        115                 120                 125

Ser Val Asn Gln Tyr Asp Tyr Trp Gly Gln Gly Thr Gln Val Thr Val
        130                 135                 140

Ser Glu Pro Lys Thr Pro Lys Gly Glu Phe Gly Gly Gly Gly Ser Gly
```

-continued

```
145                150                155                160

Gly Gly Gly Ser Ala Pro Thr Ser Ser Ser Thr Lys Lys Thr Gln Leu
            165                170                175

Gln Leu Glu His Leu Leu Leu Asp Leu Gln Met Ile Leu Asn Gly Ile
            180                185                190

Asn Asn Tyr Lys Asn Pro Lys Leu Thr Arg Met Leu Thr Phe Lys Phe
            195                200                205

Tyr Met Pro Lys Lys Ala Thr Glu Leu Lys His Leu Gln Cys Leu Glu
    210                215                220

Glu Glu Leu Lys Pro Leu Glu Glu Val Leu Asn Leu Ala Gln Ser Lys
225                230                235                240

Asn Phe His Leu Arg Pro Arg Asp Leu Ile Ser Asn Ile Asn Val Ile
            245                250                255

Val Leu Glu Leu Lys Gly Ser Glu Thr Thr Phe Met Cys Glu Tyr Ala
            260                265                270

Asp Glu Thr Ala Thr Ile Val Glu Phe Leu Asn Arg Trp Ile Thr Phe
            275                280                285

Ala Gln Ser Ile Ile Ser Thr Leu Thr Leu Glu His His His His
    290                295                300

His
305

<210> SEQ ID NO 9
<211> LENGTH: 303
<212> TYPE: PRT
<213> ORGANISM: Artificial Sequence
<220> FEATURE:
<223> OTHER INFORMATION: Synthetic construct

<400> SEQUENCE: 9

Met Ala Ser Met Thr Gly Gly Gln Gln Met Gly Arg Asp Pro Glu Asn
1               5                   10                  15

Leu Tyr Phe Gln Gly Ala Asp Val Gln Leu Val Glu Ser Gly Gly Gly
            20                  25                  30

Leu Val Gln Ala Gly Gly Ser Leu Arg Leu Ser Cys Ala Ala Ser Gly
        35                  40                  45

Gly Thr Ile Ser Asn Tyr Gly Met Gly Trp Leu Arg Gln Gly Pro Gly
    50                  55                  60

Lys Glu Arg Glu Phe Val Gly Ser Ile Asn Trp Asn Gly Ala Thr Thr
65                  70                  75                  80

His Tyr Ala Asp Ser Val Lys Gly Arg Phe Ile Ile Ser Arg Asp Asn
                85                  90                  95

Ala Lys Asn Thr Val Tyr Leu Gln Met Asn Ser Leu Lys Pro Glu Asp
            100                 105                 110

Thr Gly Val Tyr Tyr Cys Val Ala Gln Phe Ser Val Gln Pro Thr Leu
            115                 120                 125

Gln Thr Tyr Asp Tyr Arg Gly Gln Gly Thr Gln Val Thr Val Ser Glu
        130                 135                 140

Pro Lys Thr Pro Lys Gly Glu Phe Gly Gly Gly Ser Gly Gly Gly
145                 150                 155                 160

Gly Ser Ala Pro Thr Ser Ser Ser Thr Lys Lys Thr Gln Leu Gln Leu
            165                 170                 175

Glu His Leu Leu Leu Asp Leu Gln Met Ile Leu Asn Gly Ile Asn Asn
            180                 185                 190

Tyr Lys Asn Pro Lys Leu Thr Arg Met Leu Thr Phe Lys Phe Tyr Met
```

```
            195                 200                 205

Pro Lys Lys Ala Thr Glu Leu Lys His Leu Gln Cys Leu Glu Glu Glu
    210                 215                 220

Leu Lys Pro Leu Glu Glu Val Leu Asn Leu Ala Gln Ser Lys Asn Phe
225                 230                 235                 240

His Leu Arg Pro Arg Asp Leu Ile Ser Asn Ile Asn Val Ile Val Leu
                245                 250                 255

Glu Leu Lys Gly Ser Glu Thr Thr Phe Met Cys Glu Tyr Ala Asp Glu
                260                 265                 270

Thr Ala Thr Ile Val Glu Phe Leu Asn Arg Trp Ile Thr Phe Ala Gln
                275                 280                 285

Ser Ile Ile Ser Thr Leu Thr Leu Glu His His His His His
    290                 295                 300

<210> SEQ ID NO 10
<211> LENGTH: 15
<212> TYPE: PRT
<213> ORGANISM: Artificial Sequence
<220> FEATURE:
<223> OTHER INFORMATION: Synthetic construct

<400> SEQUENCE: 10

Gly Ser Gly Val Gly Arg Tyr Ile His Ala His Gln Tyr Glu Tyr
1               5                   10                  15

<210> SEQ ID NO 11
<211> LENGTH: 18
<212> TYPE: PRT
<213> ORGANISM: Artificial Sequence
<220> FEATURE:
<223> OTHER INFORMATION: Synthetic construct

<400> SEQUENCE: 11

Ser Leu Ile Glu Asp Tyr Ser Asp Tyr Val Asp Arg Thr Thr Glu Tyr
1               5                   10                  15

Asp Tyr

<210> SEQ ID NO 12
<211> LENGTH: 20
<212> TYPE: PRT
<213> ORGANISM: Artificial Sequence
<220> FEATURE:
<223> OTHER INFORMATION: Synthetic construct

<400> SEQUENCE: 12

Ser Ala Pro Glu Tyr Tyr Ser Gly Ser Tyr Tyr Leu Asn Arg Pro Asp
1               5                   10                  15

Asp Tyr Asp Tyr
            20

<210> SEQ ID NO 13
<211> LENGTH: 15
<212> TYPE: PRT
<213> ORGANISM: Artificial Sequence
<220> FEATURE:
<223> OTHER INFORMATION: Synthetic construct

<400> SEQUENCE: 13

Gly Ser Gly Gly Gly Gln Tyr Arg Tyr Gly Ile Gln Tyr Asp Tyr
1               5                   10                  15

<210> SEQ ID NO 14
```

```
<211> LENGTH: 11
<212> TYPE: PRT
<213> ORGANISM: Artificial Sequence
<220> FEATURE:
<223> OTHER INFORMATION: Synthetic construct

<400> SEQUENCE: 14

Arg Lys Met Ser Thr Val Ala Thr Glu Ala Thr
1               5                   10

<210> SEQ ID NO 15
<211> LENGTH: 17
<212> TYPE: PRT
<213> ORGANISM: Artificial Sequence
<220> FEATURE:
<223> OTHER INFORMATION: Synthetic construct

<400> SEQUENCE: 15

Arg Leu Glu Asn Gly Tyr Thr Thr Tyr Ser Arg Ile Asn Glu Tyr Asp
1               5                   10                  15

Tyr

<210> SEQ ID NO 16
<211> LENGTH: 15
<212> TYPE: PRT
<213> ORGANISM: Artificial Sequence
<220> FEATURE:
<223> OTHER INFORMATION: Synthetic construct

<400> SEQUENCE: 16

Gly Ile Ser Asp Tyr Gly Cys Tyr Arg Thr Ser Gly Tyr Asn Tyr
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic construct

<400> SEQUENCE: 17

Gly Asp Gly Leu Gly Phe Tyr Arg Ser Val Asn Gln Tyr Asp Tyr
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Synthetic construct

<400> SEQUENCE: 18

Gly Ala Gly Gly Gly Gln Tyr Arg Tyr Trp Ser Gln Tyr Asp Tyr
1               5                   10                  15

<210> SEQ ID NO 19
<211> LENGTH: 22
<212> TYPE: PRT
<213> ORGANISM: Artificial Sequence
<220> FEATURE:
<223> OTHER INFORMATION: Synthetic construct

<400> SEQUENCE: 19

Ala Glu Gly Leu Ala Ser Gly Ser Tyr Asp Tyr Val Pro Pro Leu Lys
1               5                   10                  15

Ser Ser Trp Tyr Asp Tyr
```

-continued

20

<210> SEQ ID NO 20
<211> LENGTH: 15
<212> TYPE: PRT
<213> ORGANISM: Artificial Sequence
<220> FEATURE:
<223> OTHER INFORMATION: Synthetic construct

<400> SEQUENCE: 20

Asp Ser Gly Gly Gly Gln Tyr Arg Tyr Leu Ser Gln Phe Asp Trp
1               5                   10                  15

<210> SEQ ID NO 21
<211> LENGTH: 18
<212> TYPE: PRT
<213> ORGANISM: Artificial Sequence
<220> FEATURE:
<223> OTHER INFORMATION: Synthetic construct

<400> SEQUENCE: 21

Ala Phe Thr Thr Asp His Thr Leu Val Ile Val Thr Ala Arg Arg Tyr
1               5                   10                  15

Glu Phe

<210> SEQ ID NO 22
<211> LENGTH: 15
<212> TYPE: PRT
<213> ORGANISM: Artificial Sequence
<220> FEATURE:
<223> OTHER INFORMATION: Synthetic construct

<400> SEQUENCE: 22

Asp Tyr Arg Gly Leu Gly Ser Ser Arg Ala His Asp Tyr Asp Tyr
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: Synthetic construct

<400> SEQUENCE: 23

Ala Tyr Gly Ala Gly Leu Tyr Asn Ile Ala Arg Gln Tyr Asp Tyr
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic construct

<400> SEQUENCE: 24

Ala Pro Gly Val Gly Tyr Tyr Arg His Thr Phe Gln Tyr Asp Asp
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic construct

<400> SEQUENCE: 25

Asn Ser Ala Phe Phe Gly Arg Ile Tyr Phe Gly Asn Glu Asn Tyr Tyr
1               5                   10                  15

<210> SEQ ID NO 26
<211> LENGTH: 18
<212> TYPE: PRT
<213> ORGANISM: Artificial Sequence
<220> FEATURE:
<223> OTHER INFORMATION: Synthetic construct

<400> SEQUENCE: 26

Arg Leu Asp Pro Ile Phe Ala Ser Asn Ala Asp Tyr Ala Ser Leu Tyr
1               5                   10                  15

Asp Tyr

<210> SEQ ID NO 27
<211> LENGTH: 15
<212> TYPE: PRT
<213> ORGANISM: Artificial Sequence
<220> FEATURE:
<223> OTHER INFORMATION: Synthetic construct

<400> SEQUENCE: 27

Gly Ser Gly Gly Gly Gln Tyr Arg Tyr Trp Ser Gln Phe Asp Tyr
1               5                   10                  15

<210> SEQ ID NO 28
<211> LENGTH: 19
<212> TYPE: PRT
<213> ORGANISM: Artificial Sequence
<220> FEATURE:
<223> OTHER INFORMATION: Synthetic construct

<400> SEQUENCE: 28

Gly Pro Ser Thr Ala Gln Ala Val Gly Val Pro Phe Phe Gly Tyr Pro
1               5                   10                  15

Asp Asp Tyr

<210> SEQ ID NO 29
<211> LENGTH: 16
<212> TYPE: PRT
<213> ORGANISM: Artificial Sequence
<220> FEATURE:
<223> OTHER INFORMATION: Synthetic construct

<400> SEQUENCE: 29

Arg Glu Trp Gly Ser Gly Gly Tyr Ser Ser Ile Ala Ser Tyr Ala Tyr
1               5                   10                  15

<210> SEQ ID NO 30
<211> LENGTH: 19
<212> TYPE: PRT
<213> ORGANISM: Artificial Sequence
<220> FEATURE:
<223> OTHER INFORMATION: Synthetic construct

<400> SEQUENCE: 30

Val Phe Asp Arg Leu Ser Asp Ser Leu Leu Pro Glu Glu Arg Ser Thr
1               5                   10                  15

Tyr Asp Tyr

<210> SEQ ID NO 31
<211> LENGTH: 15
<212> TYPE: PRT
<213> ORGANISM: Artificial Sequence -continued

```
<220> FEATURE:
<223> OTHER INFORMATION: Synthetic construct

<400> SEQUENCE: 31

Cys Tyr Gly Leu Gly Phe Tyr Arg Ser Val Ser Gln Tyr Asp Tyr
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic construct

<400> SEQUENCE: 32

Gly Tyr Ala Gly Leu Gly Asp Ser Arg Ala His Glu Tyr Asp Tyr
1               5                   10                  15

<210> SEQ ID NO 33
<211> LENGTH: 18
<212> TYPE: PRT
<213> ORGANISM: Artificial Sequence
<220> FEATURE:
<223> OTHER INFORMATION: Synthetic construct

<400> SEQUENCE: 33

Arg Leu Asp Pro Ile Phe Ala Ser Asn Ser Glu Tyr Ala Pro Leu Tyr
1               5                   10                  15

Glu Tyr

<210> SEQ ID NO 34
<211> LENGTH: 21
<212> TYPE: PRT
<213> ORGANISM: Artificial Sequence
<220> FEATURE:
<223> OTHER INFORMATION: Synthetic construct

<400> SEQUENCE: 34

Ala Gly Pro Gln Glu Ala Phe Trp Phe Pro Ser Asp Tyr Ala Gln Arg
1               5                   10                  15

Val Leu Tyr Asp Tyr
            20

<210> SEQ ID NO 35
<211> LENGTH: 15
<212> TYPE: PRT
<213> ORGANISM: Artificial Sequence
<220> FEATURE:
<223> OTHER INFORMATION: Synthetic construct

<400> SEQUENCE: 35

Gly Ser Gly Gly Gly Gln Tyr Arg Tyr Ser Gly Gln Tyr Asp Asp
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic construct

<400> SEQUENCE: 36

Asp Val Ile Arg His Leu Tyr Gly Ser Gly Cys Pro Val Gly Leu Tyr
1               5                   10                  15
```

-continued

```
<210> SEQ ID NO 37
<211> LENGTH: 18
<212> TYPE: PRT
<213> ORGANISM: Artificial Sequence
<220> FEATURE:
<223> OTHER INFORMATION: Synthetic construct

<400> SEQUENCE: 37

His Thr Val Leu Glu Tyr Ser Asp Tyr Val Glu Ser Asp Ala Thr Tyr
1               5                   10                  15

Ala Tyr

<210> SEQ ID NO 38
<211> LENGTH: 11
<212> TYPE: PRT
<213> ORGANISM: Artificial Sequence
<220> FEATURE:
<223> OTHER INFORMATION: Synthetic construct

<400> SEQUENCE: 38

Asp Val Ile Arg His Leu Tyr Gly Ser Asp Cys
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic construct

<400> SEQUENCE: 39

Tyr Ser Asp Tyr Asp Leu Val Arg Ala Asp Gln Tyr Asn Tyr
1               5                   10

<210> SEQ ID NO 40
<211> LENGTH: 16
<212> TYPE: PRT
<213> ORGANISM: Artificial Sequence
<220> FEATURE:
<223> OTHER INFORMATION: Synthetic construct

<400> SEQUENCE: 40

Gly Leu Ile Ala Arg Leu Tyr Gly Ser Asn Cys Pro Ala Gly Leu Tyr
1               5                   10                  15

<210> SEQ ID NO 41
<211> LENGTH: 25
<212> TYPE: PRT
<213> ORGANISM: Artificial Sequence
<220> FEATURE:
<223> OTHER INFORMATION: Synthetic construct

<400> SEQUENCE: 41

Ala Asp Pro Met Gly Leu Gly Tyr Val Leu Gly Pro Arg Pro Val Asp
1               5                   10                  15

Arg Leu Leu Ser Ala Glu Cys Asp Tyr
            20                  25

<210> SEQ ID NO 42
<211> LENGTH: 15
<212> TYPE: PRT
<213> ORGANISM: Artificial Sequence
<220> FEATURE:
<223> OTHER INFORMATION: Synthetic construct

<400> SEQUENCE: 42
```

```
Gly Ala Ser Asp Tyr Gly Cys Tyr Asn Thr Ser Gly Ile Lys Tyr
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: Synthetic construct

<400> SEQUENCE: 43

Asp Tyr Ala Gly Leu Gly Tyr Ser Gln Ala His Glu Tyr Glu Tyr
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Synthetic construct

<400> SEQUENCE: 44

Gly Ser Gly Val Gly Arg Tyr Leu Tyr Pro His Gln Tyr Asp Asn
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Synthetic construct

<400> SEQUENCE: 45

Ala Pro Gly Ala Gly Asn Tyr Arg Tyr Ser Arg Gln Tyr Asp Tyr
1               5                   10                  15

<210> SEQ ID NO 46
<211> LENGTH: 15
<212> TYPE: PRT
<213> ORGANISM: Artificial Sequence
<220> FEATURE:
<223> OTHER INFORMATION: Synthetic construct

<400> SEQUENCE: 46

Gly Ser Gly Thr Gly Ile Tyr Ser Tyr Pro His Gln Tyr Asp Tyr
1               5                   10                  15

<210> SEQ ID NO 47
<211> LENGTH: 15
<212> TYPE: PRT
<213> ORGANISM: Artificial Sequence
<220> FEATURE:
<223> OTHER INFORMATION: Synthetic construct

<400> SEQUENCE: 47

Ala Ser Gly Val Gly Met Tyr Ala Tyr Pro His Gln Tyr Asp Tyr
1               5                   10                  15

<210> SEQ ID NO 48
<211> LENGTH: 18
<212> TYPE: PRT
<213> ORGANISM: Artificial Sequence
<220> FEATURE:
<223> OTHER INFORMATION: Synthetic construct

<400> SEQUENCE: 48

Arg Leu Asp Pro Ile Phe Ala Ser Asn Ile Asp Tyr Ala Pro Leu Tyr
```

-continued

```
1               5               10              15

Asp Tyr

<210> SEQ ID NO 49
<211> LENGTH: 16
<212> TYPE: PRT
<213> ORGANISM: Artificial Sequence
<220> FEATURE:
<223> OTHER INFORMATION: Synthetic construct

<400> SEQUENCE: 49

Asp Asp Arg Ala Val Pro Met Leu Gly Asp Phe Glu Asp Tyr Ile Asp
1               5               10              15

<210> SEQ ID NO 50
<211> LENGTH: 18
<212> TYPE: PRT
<213> ORGANISM: Artificial Sequence
<220> FEATURE:
<223> OTHER INFORMATION: Synthetic construct

<400> SEQUENCE: 50

Asp Ala Arg Ser Gly Ser Ala His Leu Ala Tyr His Leu Arg Asp Tyr
1               5               10              15

Asp Tyr

<210> SEQ ID NO 51
<211> LENGTH: 14
<212> TYPE: PRT
<213> ORGANISM: Artificial Sequence
<220> FEATURE:
<223> OTHER INFORMATION: Synthetic construct

<400> SEQUENCE: 51

Asp Gln Tyr Ala Ser Thr Val Leu Arg Val Ala Gly Glu Tyr
1               5               10

<210> SEQ ID NO 52
<211> LENGTH: 12
<212> TYPE: PRT
<213> ORGANISM: Artificial Sequence
<220> FEATURE:
<223> OTHER INFORMATION: Synthetic construct

<400> SEQUENCE: 52

Gly Val Val Gly Gly Trp Ala Tyr Glu Tyr Asp Tyr
1               5               10

<210> SEQ ID NO 53
<211> LENGTH: 15
<212> TYPE: PRT
<213> ORGANISM: Artificial Sequence
<220> FEATURE:
<223> OTHER INFORMATION: Synthetic construct

<400> SEQUENCE: 53

Asp Tyr Arg Gly Leu Gly Tyr Ser Gly Ala His Glu Tyr Asp Tyr
1               5               10              15

<210> SEQ ID NO 54
<211> LENGTH: 13
<212> TYPE: PRT
<213> ORGANISM: Artificial Sequence
<220> FEATURE:
<223> OTHER INFORMATION: Synthetic construct
```

<400> SEQUENCE: 54

Gln Phe Ser Val Gln Pro Thr Leu Gln Ala Tyr Ser Tyr
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Synthetic construct

<400> SEQUENCE: 55

Lys Asn Pro Ser Ile Thr Asp Gly Glu Tyr Glu Tyr
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Synthetic construct

<400> SEQUENCE: 56

Asp Tyr Tyr Gly Leu Gly Ser Gly Leu Lys Asn Glu Tyr Glu Tyr
1               5                   10                  15

<210> SEQ ID NO 57
<211> LENGTH: 18
<212> TYPE: PRT
<213> ORGANISM: Artificial Sequence
<220> FEATURE:
<223> OTHER INFORMATION: Synthetic construct

<400> SEQUENCE: 57

Ala Phe Thr Thr Asp His Thr Leu Val Val Val Thr Thr Arg Gln Tyr
1               5                   10                  15

Asp Tyr

<210> SEQ ID NO 58
<211> LENGTH: 14
<212> TYPE: PRT
<213> ORGANISM: Artificial Sequence
<220> FEATURE:
<223> OTHER INFORMATION: Synthetic construct

<400> SEQUENCE: 58

Ser Tyr Leu Gly Trp Gly Thr Ala Arg Ser Ala Tyr Glu Tyr
1               5                   10

<210> SEQ ID NO 59
<211> LENGTH: 16
<212> TYPE: PRT
<213> ORGANISM: Artificial Sequence
<220> FEATURE:
<223> OTHER INFORMATION: Synthetic construct

<400> SEQUENCE: 59

Asp Asp Arg Ala Val Pro Met Leu Gly Asp Phe Met Asp Tyr Ile Tyr
1               5                   10                  15

<210> SEQ ID NO 60
<211> LENGTH: 22
<212> TYPE: PRT
<213> ORGANISM: Artificial Sequence
<220> FEATURE:
<223> OTHER INFORMATION: Synthetic construct

<400> SEQUENCE: 60

Ser His Tyr Leu Pro Val Arg Thr Ala Ser Gly Gly Tyr His Leu Asp
1               5                   10                  15

Thr Asp Arg Pro Gln Tyr
            20

<210> SEQ ID NO 61
<211> LENGTH: 15
<212> TYPE: PRT
<213> ORGANISM: Artificial Sequence
<220> FEATURE:
<223> OTHER INFORMATION: Synthetic construct

<400> SEQUENCE: 61

Gly Val Ser Asp Tyr Trp Cys Tyr Arg Thr Ser Gly Ile Asn Tyr
1               5                   10                  15

<210> SEQ ID NO 62
<211> LENGTH: 12
<212> TYPE: PRT
<213> ORGANISM: Artificial Sequence
<220> FEATURE:
<223> OTHER INFORMATION: Synthetic construct

<400> SEQUENCE: 62

Glu Val Met Glu Cys Arg Gly Leu Gln Tyr Asn Asp
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic construct

<400> SEQUENCE: 63

Val Pro Ser Asp Asn Leu Cys Gly Tyr Leu His
1               5                   10

<210> SEQ ID NO 64
<211> LENGTH: 15
<212> TYPE: PRT
<213> ORGANISM: Artificial Sequence
<220> FEATURE:
<223> OTHER INFORMATION: Synthetic construct

<400> SEQUENCE: 64

Glu Thr Ser Gly Trp Gly Ser Lys Val Val Pro Asn Tyr Asp Tyr
1               5                   10                  15

<210> SEQ ID NO 65
<211> LENGTH: 11
<212> TYPE: PRT
<213> ORGANISM: Artificial Sequence
<220> FEATURE:
<223> OTHER INFORMATION: Synthetic construct

<400> SEQUENCE: 65

Asp Thr Val Pro Glu Tyr Ser Asp Tyr Asp Tyr
1               5                   10

<210> SEQ ID NO 66
<211> LENGTH: 15
<212> TYPE: PRT
<213> ORGANISM: Artificial Sequence

```
<220> FEATURE:
<223> OTHER INFORMATION: Synthetic construct

<400> SEQUENCE: 66

Gly Tyr Asp Gly Gly Leu Tyr Lys Ile Ala Thr Gln Tyr Asp Tyr
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Synthetic construct

<400> SEQUENCE: 67

Ser Ala Ala Tyr Ile Gly Arg Val Tyr Phe Gly Asn Glu Asn Tyr Ser
1               5                   10                  15

<210> SEQ ID NO 68
<211> LENGTH: 19
<212> TYPE: PRT
<213> ORGANISM: Artificial Sequence
<220> FEATURE:
<223> OTHER INFORMATION: Synthetic construct

<400> SEQUENCE: 68

Asp Ser Val Asp Ala Tyr Ser Lys Gly Ser Val Tyr Ser Ala Asp Arg
1               5                   10                  15

Tyr Asp Tyr

<210> SEQ ID NO 69
<211> LENGTH: 15
<212> TYPE: PRT
<213> ORGANISM: Artificial Sequence
<220> FEATURE:
<223> OTHER INFORMATION: Synthetic construct

<400> SEQUENCE: 69

Arg Lys Thr Ser Thr Thr Thr Asn Glu Ala Thr Met Tyr Ala Tyr
1               5                   10                  15

<210> SEQ ID NO 70
<211> LENGTH: 18
<212> TYPE: PRT
<213> ORGANISM: Artificial Sequence
<220> FEATURE:
<223> OTHER INFORMATION: Synthetic construct

<400> SEQUENCE: 70

His Phe Thr Thr Asp His Thr Ile Val Val Val Thr Thr Arg Arg Tyr
1               5                   10                  15

Glu Tyr

<210> SEQ ID NO 71
<211> LENGTH: 11
<212> TYPE: PRT
<213> ORGANISM: Artificial Sequence
<220> FEATURE:
<223> OTHER INFORMATION: Synthetic construct

<400> SEQUENCE: 71

Ser Ala Ala Leu Ile Gly Arg Val Tyr Phe Gly
1               5                   10

<210> SEQ ID NO 72
```

```
<211> LENGTH: 14
<212> TYPE: PRT
<213> ORGANISM: Artificial Sequence
<220> FEATURE:
<223> OTHER INFORMATION: Synthetic construct

<400> SEQUENCE: 72

Asn Leu Arg Ser Gly Val Tyr His Leu Ser Asp Tyr Asn Tyr
1               5                   10

<210> SEQ ID NO 73
<211> LENGTH: 18
<212> TYPE: PRT
<213> ORGANISM: Artificial Sequence
<220> FEATURE:
<223> OTHER INFORMATION: Synthetic construct

<400> SEQUENCE: 73

Asp Ala Ser Ser Thr Trp Arg Gly Val Arg Ser Arg Trp Asp Glu Tyr
1               5                   10                  15

Thr Tyr

<210> SEQ ID NO 74
<211> LENGTH: 17
<212> TYPE: PRT
<213> ORGANISM: Artificial Sequence
<220> FEATURE:
<223> OTHER INFORMATION: Synthetic construct

<400> SEQUENCE: 74

Ile Arg Pro Gly Ser Pro Ile Thr Tyr Val Thr Pro Asn His Ile Asp
1               5                   10                  15

Tyr

<210> SEQ ID NO 75
<211> LENGTH: 15
<212> TYPE: PRT
<213> ORGANISM: Artificial Sequence
<220> FEATURE:
<223> OTHER INFORMATION: Synthetic construct

<400> SEQUENCE: 75

Gly Val Ser Asp Tyr Gly Cys Tyr His Pro Ser Gly Tyr Asn Tyr
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic construct

<400> SEQUENCE: 76

Gly Tyr Leu Asp Gly Leu Ala Tyr Tyr Ser Asn Asp Tyr Lys Tyr
1               5                   10                  15

<210> SEQ ID NO 77
<211> LENGTH: 10
<212> TYPE: PRT
<213> ORGANISM: Artificial Sequence
<220> FEATURE:
<223> OTHER INFORMATION: Synthetic construct

<400> SEQUENCE: 77

Leu Arg Gly Glu Asp Pro Glu Tyr Asp Tyr
1               5                   10
```

-continued

```
<210> SEQ ID NO 78
<211> LENGTH: 17
<212> TYPE: PRT
<213> ORGANISM: Artificial Sequence
<220> FEATURE:
<223> OTHER INFORMATION: Synthetic construct

<400> SEQUENCE: 78

Lys Arg Val Val Asp Val Thr Thr Ser Asn Tyr Glu Phe Arg Tyr Glu
1               5                   10                  15

Asn

<210> SEQ ID NO 79
<211> LENGTH: 16
<212> TYPE: PRT
<213> ORGANISM: Artificial Sequence
<220> FEATURE:
<223> OTHER INFORMATION: Synthetic construct

<400> SEQUENCE: 79

Val Arg Asp Asn Leu Cys Ser Asn Trp Cys Tyr Gly Leu Tyr Asp Tyr
1               5                   10                  15

<210> SEQ ID NO 80
<211> LENGTH: 11
<212> TYPE: PRT
<213> ORGANISM: Artificial Sequence
<220> FEATURE:
<223> OTHER INFORMATION: Synthetic construct

<400> SEQUENCE: 80

Leu Tyr Gly Ser Asn Cys Pro Ala Gly Leu Tyr
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Synthetic construct

<400> SEQUENCE: 81

Gly Pro Arg Asp Ser Gly Tyr Tyr Asp Phe
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Synthetic construct

<400> SEQUENCE: 82

Gly Arg Val Pro Ile Thr Ser Met Arg Arg Asn Phe Asp Val
1               5                   10

<210> SEQ ID NO 83
<211> LENGTH: 15
<212> TYPE: PRT
<213> ORGANISM: Artificial Sequence
<220> FEATURE:
<223> OTHER INFORMATION: Synthetic construct

<400> SEQUENCE: 83

Pro Val Pro Gly Ser Ser Trp Tyr Gly Ser Leu Ala Tyr Asp Tyr
```

-continued

```
1               5                10               15

<210> SEQ ID NO 84
<211> LENGTH: 12
<212> TYPE: PRT
<213> ORGANISM: Artificial Sequence
<220> FEATURE:
<223> OTHER INFORMATION: Synthetic construct

<400> SEQUENCE: 84

Gly Tyr Gly Asp Tyr Tyr Tyr Ala Val Leu Asp Ser
1               5                10

<210> SEQ ID NO 85
<211> LENGTH: 15
<212> TYPE: PRT
<213> ORGANISM: Artificial Sequence
<220> FEATURE:
<223> OTHER INFORMATION: Synthetic construct

<400> SEQUENCE: 85

Asp Tyr Ala Gly Leu Gly Asp Ser Arg Ala His Val Tyr Glu Tyr
1               5                10               15

<210> SEQ ID NO 86
<211> LENGTH: 16
<212> TYPE: PRT
<213> ORGANISM: Artificial Sequence
<220> FEATURE:
<223> OTHER INFORMATION: Synthetic construct

<400> SEQUENCE: 86

Gly Arg Tyr Ser Thr Leu Phe Thr Thr Ser Glu Ala Asp Tyr Asp Tyr
1               5                10               15

<210> SEQ ID NO 87
<211> LENGTH: 14
<212> TYPE: PRT
<213> ORGANISM: Artificial Sequence
<220> FEATURE:
<223> OTHER INFORMATION: Synthetic construct

<400> SEQUENCE: 87

Asp Gln Tyr Ala Ser Thr Val Leu Ser Ala Met Gly Glu Tyr
1               5                10

<210> SEQ ID NO 88
<211> LENGTH: 8
<212> TYPE: PRT
<213> ORGANISM: Artificial Sequence
<220> FEATURE:
<223> OTHER INFORMATION: Synthetic construct

<400> SEQUENCE: 88

Gly Gly Gly Ser Gln Tyr Glu Tyr
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic construct

<400> SEQUENCE: 89

Ser Arg Trp Leu Thr Ser Asp Ala Tyr
1               5
```

-continued

```
<210> SEQ ID NO 90
<211> LENGTH: 18
<212> TYPE: PRT
<213> ORGANISM: Artificial Sequence
<220> FEATURE:
<223> OTHER INFORMATION: Synthetic construct

<400> SEQUENCE: 90

Leu Ser Tyr Gly Ser Met Trp Leu Asp Ala Ser Glu Arg Asn Glu Tyr
1               5                   10                  15

Asp Ser

<210> SEQ ID NO 91
<211> LENGTH: 9
<212> TYPE: PRT
<213> ORGANISM: Artificial Sequence
<220> FEATURE:
<223> OTHER INFORMATION: Synthetic construct

<400> SEQUENCE: 91

Glu Ile Leu Gly Gly Gly Pro Asn Tyr
1               5

<210> SEQ ID NO 92
<211> LENGTH: 13
<212> TYPE: PRT
<213> ORGANISM: Artificial Sequence
<220> FEATURE:
<223> OTHER INFORMATION: Synthetic construct

<400> SEQUENCE: 92

Gly Ser Thr Ser Ser Trp Lys Glu Glu Trp Tyr Asp Asn
1               5                   10

<210> SEQ ID NO 93
<211> LENGTH: 20
<212> TYPE: PRT
<213> ORGANISM: Artificial Sequence
<220> FEATURE:
<223> OTHER INFORMATION: Synthetic construct

<400> SEQUENCE: 93

Asp Leu Ser Asp Phe Ile Asp Arg Tyr Cys Ile Pro Arg Ser Pro Ile
1               5                   10                  15

Gly Tyr Asp Tyr
            20

<210> SEQ ID NO 94
<211> LENGTH: 7
<212> TYPE: PRT
<213> ORGANISM: Artificial Sequence
<220> FEATURE:
<223> OTHER INFORMATION: Synthetic construct

<400> SEQUENCE: 94

Thr Ile Gly Pro Arg Leu Tyr
1               5

<210> SEQ ID NO 95
<211> LENGTH: 13
<212> TYPE: PRT
<213> ORGANISM: Artificial Sequence
<220> FEATURE:
<223> OTHER INFORMATION: Synthetic construct
```

-continued

```
<400> SEQUENCE: 95

Gly Asp Ser Ser Ser Trp Lys Asp Val Gln Tyr Asp Tyr
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthetic construct

<400> SEQUENCE: 96

Lys Ser Pro Ser Ser Ser Glu Phe Glu Phe
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Synthetic construct

<400> SEQUENCE: 97

Ser Arg Tyr Met Ile Val His Gly Thr Lys Asn Leu Asp Asp
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic construct

<400> SEQUENCE: 98

Ala Pro Leu Asp Gly Leu Glu Cys Val Arg Gln
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic construct

<400> SEQUENCE: 99

Gly Asp Ser Ser Ser Trp Leu Glu Asp Arg Tyr Asp Tyr
1               5                   10

<210> SEQ ID NO 100
<211> LENGTH: 15
<212> TYPE: PRT
<213> ORGANISM: Artificial Sequence
<220> FEATURE:
<223> OTHER INFORMATION: Synthetic construct

<400> SEQUENCE: 100

Arg Gly Gly Ile Ala Val Ala Met Ser Ser Arg Asp Tyr Asp Tyr
1               5                   10                  15

<210> SEQ ID NO 101
<211> LENGTH: 25
<212> TYPE: PRT
<213> ORGANISM: Artificial Sequence
<220> FEATURE:
<223> OTHER INFORMATION: Synthetic construct

<400> SEQUENCE: 101
```

-continued

```
Tyr Glu Thr Thr Leu Glu Lys Cys Cys Ala Ala Ala Asp Pro His Glu
1               5                   10                  15

Cys Tyr Ala Lys Val Phe Asp Glu Phe
            20                  25

<210> SEQ ID NO 102
<211> LENGTH: 25
<212> TYPE: PRT
<213> ORGANISM: Artificial Sequence
<220> FEATURE:
<223> OTHER INFORMATION: Synthetic construct

<400> SEQUENCE: 102

Tyr Glu Ala Thr Leu Glu Asp Cys Cys Ala Lys Asp Asp Pro His Ala
1               5                   10                  15

Cys Tyr Ala Thr Val Phe Asp Lys Leu
            20                  25

<210> SEQ ID NO 103
<211> LENGTH: 134
<212> TYPE: PRT
<213> ORGANISM: Artificial Sequence
<220> FEATURE:
<223> OTHER INFORMATION: Synthetic construct

<400> SEQUENCE: 103

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
            85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
        130
```